United States Patent
Meerpoel et al.

(10) Patent No.: US 6,384,030 B1
(45) Date of Patent: May 7, 2002

(54) WATER SOLUBLE AZOLES AS BROAD-SPECTRUM ANTIFUNGALS

(76) Inventors: Lieven Meerpoel; Leo Jacobus Jozef Backx; Louis Jozef Elisabeth Van der Veken; Jan Heeres, all of Janssen Pharmaceutica N.V., Turnhoutseweg 30, Beerse B-2340 (BE); Frank Christopher Odds, North Coldstream, Drumoak AB31 5EP (GB)

(*) Notice: Subject to any disclaimer, the term of this patent is extended or adjusted under 35 U.S.C. 154(b) by 0 days.

(21) Appl. No.: 09/700,251

(22) PCT Filed: May 6, 1999

(86) PCT No.: PCT/EP99/03243

§ 371 Date: Nov. 9, 2000

§ 102(e) Date: Nov. 9, 2000

(87) PCT Pub. No.: WO99/58530

PCT Pub. Date: Nov. 18, 1999

(30) Foreign Application Priority Data

May 14, 1998 (EP) .............................................. 98201588

(51) Int. Cl.[7] ..................... C07D 405/14; C07D 249/12; A61K 31/495
(52) U.S. Cl. ..................... 514/232.2; 544/367; 544/371; 544/357; 544/121; 544/364; 514/252.11; 514/253.1
(58) Field of Search ................................. 544/367, 371, 544/357, 121, 364, 252.11, 253.1, 232.2

(56) References Cited

FOREIGN PATENT DOCUMENTS

| | | |
|---|---|---|
| WO | WO 95/17407 | 6/1995 |
| WO | WO 95/19983 | 7/1995 |
| WO | WO 96/38443 | 12/1996 |
| WO | WO 97/00255 | 1/1997 |
| WO | WO 98/34934 | 8/1998 |

OTHER PUBLICATIONS

Anil K. Saksena, SCH 51048, A Novel Broad–Spectrum Orally Active Antifungal Agent: Synthesis and Preliminary Structure–Activity Profile, *Bioorganic & Medicinal Chemistry Letters*, 1995 vol. 5 No. 2 pp. 127–132.

Primary Examiner—Richard L. Raymond
Assistant Examiner—Hong Liu

(57) ABSTRACT

The present invention concerns novel compounds of formula (I)

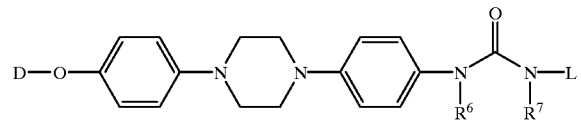

the N-oxide forms, the pharmaceutically acceptable addition salts and stereochemically isomeric forms thereof, wherein L represent a radical of formula (a)

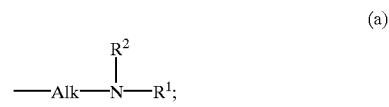

(b)

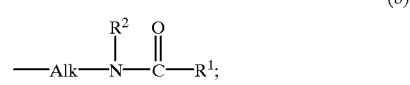

(c)

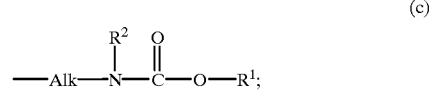

(d)

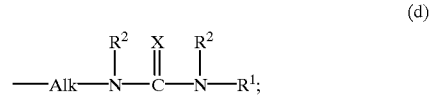

(e)

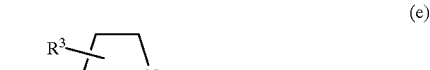

; or (f)

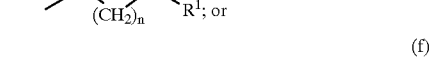

wherein each Alk independently represents an optionally substituted $C_{1-6}$alkanediyl; is 1, 2 or 3; Y is O, S or $NR^2$; $R^1$ represents hydrogen, aryl, $Het^1$, or an optionally substituted $C_{1-6}$alkyl; each $R^2$ independently represents hydrogen or $C_{1-6}$alkyl; or in case $R^1$ and $R^2$ are attached to the same nitrogen atom, they may be taken together to form a heterocyclic radical; or they may be taken together to form an azido radical; each $R^3$ independently represents hydrogen, hydroxy or $C_{1-4}$alkyloxy; aryl represents phenyl, naphthalenyl, 1,2,3,4-tetrahydro-naphthalenyl, indenyl or indanyl; each of said aryl groups may optionally be substituted; $Het^1$ represents an optionally substituted monocyclic or bicyclic heterocyclic radical; $Het^2$ is the same as $Het^1$ and may also be piperazinyl, homopiperazinyl, 1,4-dioxanyl, morpholinyl, thiomorpholinyl; $R^6$ represents hydrogen or $C_{1-4}$alkyl; $R^7$ represents hydrogen or $C_{1-4}$alkyl; or $R^6$ and $R^7$ taken together form a bivalent radical of formula —N=CH— (i), —CH=N— (ii), —CH=CH— (iii), —$CH_2$—$CH_2$— (iv), wherein one hydrogen atom in the radicals (i) and (ii) may be replaced with a $C_{1-4}$alkyl radical and one or more hydrogen atoms in radicals (iii) and (iv) may be replaced by a $C_{1-4}$alkyl radical; D represents a trisubstituted 1,3-dioxolane derivative; as antifungals; their processes for preparation, compositions containing them and their use as a medicine.

12 Claims, No Drawings

WATER SOLUBLE AZOLES AS BROAD-SPECTRUM ANTIFUNGALS

CROSS REFERENCE TO RELATED APPLICATIONS

This application is a National Stage application under 35 U.S.C. §371 of PCT/EP99/03243 filed May 6, 1999, which claims priority from EP 98.201.588.5, filed May 14, 1998.

The present invention is concerned with water soluble azoles as broad-spectrum antifungals and their preparation; it further relates to compositions comprising them, as well as their use as a medicine.

Systemic fungal infections in man are relatively rare in temperate countries and many of the fungi that can become pathogenic normally live commensally in the body or are common in the environment. The past few decades have witnessed an increasing incidence of numerous life-threatening systemic fungal infections world-wide and these now represent a major threat to many susceptible patients, particularly those already hospitalized. Most of the increase can be attributed to improved survival of immunocompromised patients and the chronic use of antimicrobial agents. Moreover, the flora typical of many common fungal infections is also changing and this is presenting an epidemiological challenge of increasing importance. Patients at greatest risk include those with impaired immune functioning, either directly as a result of immunosuppression from cytotoxic drugs or HIV infection, or secondary to other debilitating diseases such as cancer, acute leukaemia, invasive surgical techniques or prolonged exposure to antimicrobial agents. The most common systemic fungal infections in man are candidosis, aspergillosis, histoplasmosis, coccidioidomycosis, paracoccidioidomycosis, blastomycosis and cryptococcosis.

Antifungals such as ketoconazole, itraconazole and fluconazole are employed for the treatment and prophylaxis of systemic fungal infections in immunocompromised patients. However, concern is growing about fungal resistance to some of these agents, especially these with a relatively narrow spectrum, e.g. fluconazole. Worse still, it is recognized in the medical world that about 40% of the people suffering from severe systemic fungal infections are hardly, or not at all, able to receive medication via oral administration. This inability is due to the fact that such patients are in coma or suffer from severe gastroparesis. Hence, the use of insoluble or sparingly soluble antifungals such as itraconazole, that are difficult to administer intravenously, is heavily impeded in this group of patients.

Also the treatment of onychomycosis may well be served by potent water soluble antifungals. It is long desired to treat onychomycosis via the transungual route. The problem that then arises is to ensure that the antifungal agents will penetrate into and beneath the nail. Mertin and Lippold (J. Pharm. Pharmacol. (1997), 49, 30–34) stated that in order to screen for drugs for topical application to the nail plate, attention has to be paid mainly to the water solubility of the compound. The maximum flux through the nail is beneficially influenced by increasing the water solubility of the antifungal. Of course, efficacy in treating onychomycosis via the transungual route is also dependent on the potency of the antifungal.

Consequently, there is a need for new antifungals, preferably broad-spectrum antifungals, against which there is no existing resistance and which can be administered intravenously or transungually. Preferably the antifungal should also be available in a pharmaceutical composition suitable for oral administration. This enables the physician to continue treatment with the same drug after the patient has recovered from the condition which required intravenous or transungual administration of said drug.

U.S. Pat. No. 4,267,179 discloses heterocyclic derivatives of (4-phenylpiperazin-1-yl-aryloxymethyl-1,3-dioxolan-2-yl)-methyl-1H-imidazoles and 1H-1,2,4-triazoles useful as antifungal agents. Said patent encompasses itraconazole, which is available as a broad-spectrum antifungal on a world-wide basis.

WO 93/19061 discloses the [2R-[2α,4α,4(R*)]], [2R-[2α,4α,4(S*)]], [2S-[2α,4α,4(S*)]] and [2S-[2α,4α,4(R*)]] stereospecific isomers of itraconazole, which are taught to have greater water solubility than the respective diastereomeric mixtures thereof.

WO 95/19983 discloses derivatives of [[4-[4-(4-phenyl-1-piperazinyl)phenoxymethyl]-1,3-dioxolan-2-yl]methyl]-1H-imidazoles and 1H-1,2,4-triazoles, structurally related to some of the compounds of the present invention, which are taught to be water-soluble antimicrobial agents.

WO 95/17407 discloses tetrahydrofuran antifungals as well as WO 96/38443 and WO 97/00255. The latter two publications disclose tetrahydrofuran antifungals, which are taught to be soluble and/or suspensible in an aqueous medium suitable for intravenous administration, containing substitution groups readily convertible in vivo into hydroxy groups.

Saksena et al. in Bioorganic & Medicinal Chemistry Letters (1995), 5(2), 127–132, discloses some tetrahydrofuran based azole antifungals such as (3R-cis)-4-[4-[4-[4-[[5-(2,4-difluorophenyl)tetrahydro-5-(1H-1,2,4-triazol-1-ylmethyl)-3-furanyl]methoxy]phenyl]-1-piperazinyl]phenyl]-2-[2-(dimethylamino)ethyl]-2,4-dihydro-3H-1,2,4-triazol-3-one. Saksena et al. reported of said azole that, when compared to SCH 51048, it was profoundly less active as antifungal.

Unexpectedly, the compounds of the present invention are potent broad-spectrum antifungals with good water solubility.

The present invention concerns compounds of formula

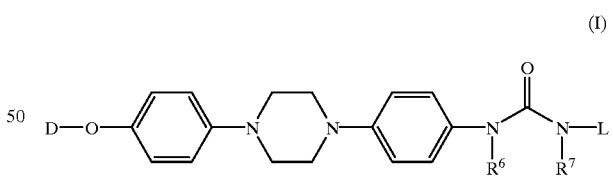

(I)

the N-oxide forms, the pharmaceutically acceptable addition salts and stereochemically isomeric forms thereof, wherein L represents a radical of formula

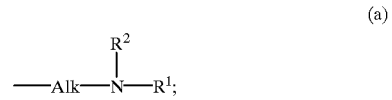

(a)

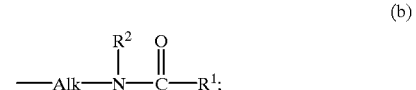

(b)

-continued (c)
$$-Alk-N(R^2)-C(=O)-O-R^1;$$

(d)
$$-Alk-N(R^2)-C(=Y)-N(R^2)-R^1;$$

(e)

[structure with R³, (CH₂)ₙ, N—R¹; ring]

(f)

[structure with R³, (CH₂)ₙ, N(R¹)(R²); ring]

wherein
each Alk independently represents $C_{1-6}$alkanediyl optionally substituted with hydroxy or $C_{1-4}$alkyloxy;
each n independently is 1, 2 or 3;
Y represents O, S or $NR^2$;
each $R^1$ independently represents hydrogen, aryl, $Het^1$, or $C_{1-6}$alkyl optionally substituted with one, two or three substituents each independently selected from halo, hydroxy, mercapto, $C_{1-4}$alkyloxy, $C_{1-4}$alkylthio, aryloxy, arylthio, aryl$C_{1-4}$alkyloxy, aryl$C_{1-4}$alkylthio, cyano, amino, mono- or di($C_{1-4}$alkyl)amino, mono- or di(aryl)amino, mono- or di(aryl$C_{1-4}$alkyl)amino, $C_{1-4}$alkyloxycarbonylamino, benzyloxycarbonylamino, aminocarbonyl, carboxyl, $C_{1-4}$alkyloxycarbonyl, guanidinyl, aryl or $Het^2$;
each $R^2$ independently represents hydrogen or $C_{1-6}$alkyl; or
in case $R^1$ and $R^2$ are attached to the same nitrogen atom, they may be taken together to form a heterocyclic radical selected from morpholinyl, pyrrolidinyl, piperidinyl, homopiperidinyl or piperazinyl; said heterocyclic radical may optionally be substituted with $C_{1-4}$alkyl, aryl, $Het^2$, aryl$C_{1-4}$alkyl, $Het^2C_{1-4}$alkyl, hydroxy$C_{1-4}$alkyl, amino, mono- or di($C_{1-4}$alkyl)amino, amino$C_{1-4}$alkyl, mono- or di($C_{1-4}$alkyl)amino$C_{1-4}$alkyl, carboxyl, aminocarbonyl, $C_{1-4}$alkyloxycarbonyl, $C_{1-4}$alkyloxycarbonylamino or mono- or di($C_{1-4}$alkyl)aminocarbonyl; or they may be taken together to form an azido radical;
each $R^3$ independently represents hydrogen, hydroxy or $C_{1-4}$alkyloxy;
aryl represents phenyl, naphthalenyl, 1,2,3,4-tetrahydronaphthalenyl, indenyl or indanyl; each of said aryl groups may optionally be substituted with one or more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy$C_{1-4}$alkyl, amino$C_{1-4}$alkyl, mono- or di($C_{1-4}$alkyl)amino$C_{1-4}$alkyl;
$Het^1$ represents a monocyclic or bicyclic heterocyclic radical; said monocyclic heterocyclic radical being selected from the group pyridinyl, piperidinyl, homopiperidinyl, pyrazinyl, pyrimidinyl, pyridazinyl, triazinyl, triazolyl, pyranyl, tetrahydropyranyl, imidazolyl, imidazolinyl, imidazolidinyl, pyrazolyl, pyrazolinyl, pyrazolidinyl, thiazolyl, thiazolidinyl, isothiazolyl, oxazolyl, oxazolidinyl, isoxazolyl, pyrrolyl, pyrrolinyl, pyrrolidinyl, furanyl, tetrahydrofuranyl, thienyl, thiolanyl, dioxolanyl; said bicyclic heterocyclic radical being selected from the group quinolinyl, 1,2,3,4-tetra-hydro-quinolinyl, isoquinolinyl, quinoxalinyl, quinazolinyl, phtalazinyl, cinnolinyl, chromanyl, thiochromanyl, 2H-chromenyl, 1,4-benzodioxanyl, indolyl, isoindolyl, indolinyl, indazolyl, purinyl, pyrrolopyridinyl, furanopyridinyl, thienopyridinyl, benzothiazolyl, benzoxazolyl, benzisothiazolyl, benzisoxazolyl, benzimidazolyl, benzofuranyl, benzothienyl; whereby each of said mono- or bicyclic heterocycle may optionally be substituted with one or where possible more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy-$C_{1-4}$alkyl, amino$C_{1-4}$alkyl, mono- or di($C_{1-4}$alkyl)amino$C_{1-4}$alkyl, aryl or aryl$C_{1-4}$alkyl;

$Het^2$ is the same as $Het^1$ and may also be a monocyclic heterocycle selected from piperazinyl, homopiperazinyl, 1,4-dioxanyl, morpholinyl, thiomorpholinyl; whereby each of said monocyclic heterocycle may optionally be substituted with one or where possible more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy$C_{1-4}$alkyl, amino$C_{1-4}$alkyl, mono- or di-($C_{1-4}$alkyl)amino$C_{1-4}$alkyl, aryl or aryl$C_{1-4}$alkyl;

$R^6$ represents hydrogen or $C_{1-4}$alkyl;

$R^7$ represents hydrogen or $C_{1-4}$alkyl; or $R^6$ and $R^7$ taken together form a bivalent radical of formula $—R^6—R^7—$ wherein $—R^6—R^7—$ is:

| | |
|---|---|
| —N=CH— | (i), |
| —CH=N— | (ii); |
| —CH=CH— | (iii), |
| —CH₂—CH₂ | (iv), | wherein one hydrogen atom in the radicals (i) and (ii) may be replaced with a $C_{1-4}$alkyl radical and one or more hydrogen atoms in radicals (iii) and (iv) may be replaced by a $C_{1-4}$alkyl radical;

D represents a radical of formula (D₁)

[chemical structure showing imidazole ring connected via CH₂ to a dioxolane ring bearing R⁴ substituted phenyl with R⁵, and a CH₂—X group]

-continued

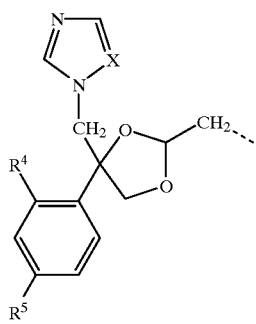

(D₂)

wherein
X is N or CH;
R is hydrogen or halo;
R⁵ is halo.

As used in the foregoing definitions and hereinafter halo defines fluoro, chloro, bromo and iodo; $C_{1-4}$alkyl encompasses the straight and branched chained saturated hydrocarbon radicals having from 1 to 4 carbon atoms such as, for example, methyl, ethyl, propyl, butyl and the like; $C_{1-6}$alkyl encompasses the straight and branched chained saturated hydrocarbon radicals as defined in $C_{1-4}$alkyl as well as the higher homologues thereof containing 5 or 6 carbon atoms such as, for example, pentyl or hexyl; $C_{1-6}$alkanediyl encompasses the straight and branched chained saturated bivalent hydrocarbon radicals having from 1 to 6 carbon atoms such as, for example, methylene, 1,2thanediyl, 1,3-propanediyl, 1,4-butanediyl, 1,5-pentanediyl, 1,6-hexanediyl, 1,2-propanediyl, 1,2-butanediyl, 2,3-butanediyl and the like.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible stereoisomeric forms in which the compounds of formula (I) exist, thus, also including all enantiomers, enantiomeric mixtures and diastereomeric mixtures. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' being equivalent to 'chirally pure' concerns compounds or intermediates having a stereoisomeric excess of at least 80% (ie. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

The terms cis and trans are used herein in accordance with Chemical Abstracts nomenclature and refer to the position of the substituents on a ring moiety, more in particular on the dioxolane ring in the compounds of formula (I). For instance, when establishing the cis or trans configuration of the dioxolane ring in a radical of formula (D₁), the substituent with the highest priority on the carbon atom in the 2 position of the dioxolane ring, and the substituent with the highest priority on the carbon atom in the 4 position of the dioxolane ring are considered (the priority of a substituent being determined according to the Cahn-Ingold-Prelog sequence rules). When said two substituents with highest priority are at the same side of the ring then the configuration is designated cis, if not, the configuration is designated trans.

The compounds of formula (I) all contain at least 2 asymmetric centers which may have the R- or S-configuration. As used herein, the stereochemical descriptors denoting the stereochemical configuration of each of the 2 or more asymmetric centers are also in accordance with Chemical Abstracts nomenclature. For instance, the absolute configuration of the asymmetric carbon atoms of compound 86, i.e. [2S-[2α,4α[(R*,S*)(S*)]]]-4-[4-[4-[4-[[2-(2,4-difluoropheny)-2-(1H-1,2,4-triazol-1-yl-methyl)-1,3-dioxolan-4-yl]methoxy]phenyl]-1-piperazinyl]phenyl]-2,4-dihydro-2-[2-[(1-phenylethyl)amino]-1-methylpropyl]-3H-1,2,4-triazol-3-one, is as depicted hereinbelow. The dioxolane ring in this compound has the cis configuration.

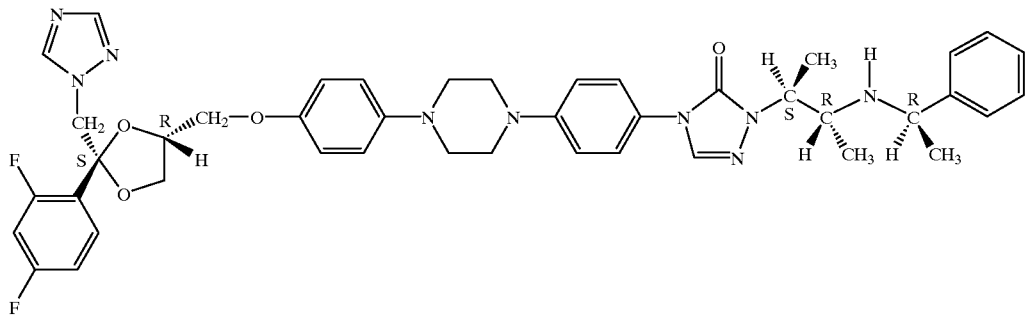

Ring numbering on the dioxolane ring according to the Chemical Abstracts nomenclature is given for radicals $D_1$ and $D_2$ just below.

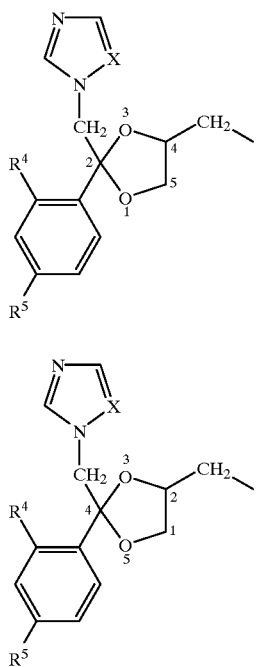

Of some compounds of formula (I) and of intermediates used in their preparation, the absolute stereochemical configuration was not experimentally determined. In those cases the stereoisomeric form which was first isolated is designated as "A", the second as "B" and if more stereogenic forms are present the third "C", the fourth "D" and so on, without further reference to the actual stereochemical configuration. However, stereogenic forms denominated "A", "B", "C", "D" and so on can be unambiguously characterized. For instance, in case "A" and "B" have an enantiomeric relationship, they can be unambiguously characterized by their optical rotation. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

The N-oxide forms of the present compounds are meant to comprise the compounds of formula (I) wherein one or several nitrogen atoms are oxidized to the so-called N-oxide.

Whenever used hereinafter, the term "compounds of formula (I)" is meant to also include their N-oxide forms, their pharmaceutically acceptable addition salts, and their stereochemically isomeric forms.

Within the scope of the present invention, $R^6$ and $R^7$ each independently are suitably hydrogen or methyl; or taken together form $-R^6-R^7-$ which suitably is a radical of formula (i) to (iv) optionally substituted with $C_{1-4}$alkyl.

D is suitably a radical of formula $D_1$.

X is suitably N.

$R^2$ is suitably hydrogen, methyl or ethyl.

$R^4$ and $R^5$ suitably are identical, preferably chloro or fluoro. In particular, both $R^4$ and $R^5$ are fluoro.

Aryl is suitably phenyl, 1,2,3,4-tetrahydro-naphtalenyl, naphtalenyl or indanyl, said aryl optionally substituted with one or more substituents selected from halo, $C_{1-4}$alkyloxy, hydroxy$C_{1-4}$alkyl, $C_{1-4}$alkyloxy$C_{1-4}$alkyl, hydroxy, amino$C_{1-4}$alkyl and mono- or di($C_{1-4}$alkyl)amino$C_{1-4}$alkyl.

$Het^1$ is suitably a monocyclic heterocyclic radical; preferably, pyridinyl, piperidinyl, pyrazinyl, pyrimidinyl, pyridazinyl, imidazolyl, pyrazolyl, thiazolyl, isothiazolyl, oxazolyl, isoxazolyl, pyrrolyl, furanyl, tetrahydrofuranyl or thienyl, each of said monocyclic heterocycles may optionally be substituted with one or where possible more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy-$C_{1-4}$alkyl, amino$C_{1-4}$alkyl, mono- or di($C_{1-4}$alkyl)amino-$C_{1-4}$alkyl; more preferably pyridinyl, piperidinyl or tetrahydrofuranyl.

$Het^1$ may also be suitably chromanyl.

An interesting group of compounds within the present invention are those compounds of formula (I) wherein L represents a radical of formula (a), (b) or (c), especially a radical of formula (a).

Another interesting group are those compounds of formula (I) wherein Alk is $C_{1-6}$alkanediyl; particularly, 1,2-ethanediyl, 1,2-propanediyl, 2,3-propanediyl, 1,2-butanediyl, 3,4-butanediyl, 2,3-butanediyl, 2,3-pentanediyl and 3,4-pentanediyl; especially 2,3-butanediyl.

Yet another interesting group contains those compounds of formula (I) wherein $R^1$ represents hydrogen, aryl, $Het^1$, or $C_{1-6}$alkyl optionally substituted with one, two or three substituents each independently selected from halo, hydroxy, $C_{1-4}$alkyloxy, aryloxy, aryl$C_{1-4}$alkyloxy, cyano, amino, mono- or di($C_{1-4}$alkyl)amino, mono- or di(aryl$C_{1-4}$alkyl)amino, $C_{1-4}$alkyloxycarbonylamino, $C_{1-4}$alkyloxycarbonyl, aminocarbonyl, aryl or $Het^2$;

$R^2$ represents hydrogen or $C_{1-6}$alkyl; or in case $R^1$ and $R^2$ are attached to the same nitrogen atom, they may also be taken together to form a heterocyclic radical selected from morpholinyl, pyrrolidinyl, piperidinyl or piperazinyl; said heterocyclic radical may optionally be substituted with $C_{1-4}$alkyl, aryl, aryl$C_{1-4}$alkyl, hydroxy$C_{1-4}$alkyl, amino, mono- or di($C_{1-4}$alkyl)amino, mono- or di($C_{1-4}$alkyl)amino$C_{1-4}$alkyl or $C_{1-4}$alkyloxycarbonylamino; or they may also be taken together to form an azido radical.

Particular compounds are those compounds of formula (I) wherein $R^6$ and $R^7$ are taken together to form —$R^6$—$R^7$— which is a radical of formula (ii) or (iii) and D is a radical of formula $D_1$ or $D_2$ wherein $R^4$ and $R^5$ both are chloro or fluoro and X is N; more in particular, a radical of formula $D_1$ or $D_2$ wherein the dioxolane ring has a cis configuration.

Other particular compounds are those compounds of formula (I) wherein L represents a radical of formula (a) wherein $R^2$ is hydrogen, methyl or ethyl; and $R^1$ represents hydrogen, aryl, Het$^1$ or $C_{1-6}$alkyl optionally substituted with one, two or three substituents each independently selected from hydroxy, $C_{1-4}$alkyloxy, aryloxy, aryl$C_{1-4}$alkyloxy, cyano, amino, mono- or di($C_{1-4}$alkyl)amino, mono- or di(aryl$C_{1-4}$alkyl)amino, aminocarbonyl, $C_{1-4}$alkyloxycarbonyl, $C_{1-4}$alkyloxycarbonylamino, aryl or Het$^2$; or $R^1$ and $R^2$ taken together with the nitrogen atom to which they are attached form a morpholinyl, pyrrolidinyl, piperidinyl or piperazinyl; said heterocyclic radical may optionally be substituted with $C_{1-4}$alkyl, aryl, aryl$C_{1-4}$alkyl, hydroxy$C_{1-4}$alkyl, amino, mono- or di($C_{1-4}$alkyl)amino, mono- or di($C_{1-4}$alkyl)amino$C_{1-4}$alkyl or $C_{1-4}$alkyloxycarbonylamino; or $R^1$ and $R^2$ taken together with the nitrogen atom to which they are attached form an azido radical.

Yet other particular compounds are those compounds of formula (I) wherein L represents a radical of formula (a), (e) or (f), especially a radical of formula (a), wherein $R^1$ represents aryl, Het$^1$, or $C_{1-6}$alkyl substituted with at least one of the substituents selected from aryloxy, arylthio, aryl$C_{1-4}$alkyloxy, aryl$C_{1-4}$alkylthio, mono- or di(aryl)amino, mono- or di(aryl$C_{1-4}$alkyl)amino, benzyloxycarbonylamino, aryl or Het$^2$; more in particular, wherein $R^1$ represents aryl or $C_{1-6}$alkyl substituted with at least one of the substituents selected from aryloxy, aryl$C_{1-4}$alkyloxy, mono- or di(aryl$C_{1-4}$ alkyl)amino, aryl or Het$^2$.

A preferred group of compounds contains those compounds of formula (I) wherein $R^6$ and $R^7$ are taken together to form —$R^6$—$R^7$— which is a radical of formula (ii) or (iii); D is a radical of formula $D_1$ or $D_2$ wherein $R^4$ and $R^5$ both are fluoro and X is N; and L represents a radical of formula (a) wherein $R^2$ is hydrogen or methyl and $R^1$ represents hydrogen, aryl, Het$^1$ or $C_{1-6}$alkyl optionally substituted with one, two or three substituents each independently selected from hydroxy, $C_{1-4}$alkyloxy, aryloxy, aryl$C_{1-4}$alkyloxy, cyano, amino, mono- or di($C_{1-4}$alkyl)amino, mono- or di(aryl$C_{1-4}$alkyl)amino, aminocarbonyl, $C_{1-4}$alkyloxycarbonyl, $C_{1-4}$alkyloxycarbonylamino, aryl or Het$^2$; or $R^1$ and $R^2$ taken together with the nitrogen atom to which they are attached form a morpholinyl, pyrrolidinyl, piperidinyl or piperazinyl; said heterocyclic radical may optionally be substituted with $C_{1-4}$alkyl, aryl, aryl$C_{1-4}$alkyl, hydroxy$C_{1-4}$alkyl, amino, mono- or di($C_{1-4}$alkyl)amino, mono- or di($C_{1-4}$alkyl)amino$C_{1-4}$alkyl or $C_{1-4}$alkyloxycarbonylamino.

Another preferred group of compounds are those compounds of formula (I) wherein $R^6$ and $R^7$ are other than hydrogen, said group is represented by compounds of formula (I').

A particularly preferred group of compounds comprises those compounds of formula (I) wherein L is a radical of formula

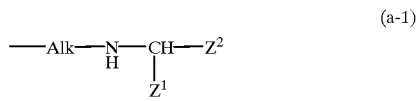

(a-1)

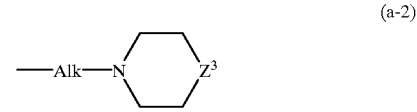

(a-2)

wherein

Alk is as defined above but preferably is 1,2-ethanediyl, 1,2-propanediyl, 2,3-propanediyl, 1,2-butanediyl, 3,4-butanediyl, 2,3-butanediyl, 2,3-pentanediyl or 3,4-pentanediyl;

$Z^1$ is aryl, arylmethyl, arylethyl, Het$^1$ or $C_{1-4}$alkyl but preferably is optionally substituted phenyl or optionally substituted phenylmethyl, isopropyl or tert-butyl;

$Z^2$ is hydrogen, carboxyl, $C_{1-4}$alkyloxycarbonyl, aminocarbonyl or methyl optionally substituted with hydroxy, methoxy, amino or mono- or di(methyl)amino but preferably is hydrogen, methyl or hydroxymethyl;

or $Z^1$ and $Z^2$ taken together with the carbon atom to which they are attached form a piperidinyl ring substituted with arylmethyl, arylethyl or $C_{1-4}$alkyl;

$Z^3$ is O, N—$C_{1-4}$alkyl or N-aryl.

Most preferred are the compounds:

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[(1-phenylethyl)amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxlan-4-yl]-methoxy]phenyl]-1-piperazinyl]phenyl]-2,4-dihydro-2-[2-[(2-phenylethyl)amino]1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-(4-phenyl-1-piperazinyl)methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[(3-phenylpropyl)amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2-[2-[[(2-fluorophenyl)methyl]amino]-1-methylpropyl]-2,4-dihydro-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[(phenylmethyl)amino]-1-methylpropyl]-3H-1,2,4,-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[[(2-methoxyphenyl)-methyl]amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[(2-phenoxyethyl)amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1- piperazinyl]phenyl]-2,4-dihydro-2-[2-[(2,3-dihydro-1H-inden-2-yl)amino]-1-methylpropyl]-3H-1,2,4,-triazol-3-one;

4-[4-[4-[4-[[2-(2,4-difluorophenyl)-2-(1-H-1,2,4-triazol-1-ylmethyl)-1,3-dioxolan-4-yl]-methoxy]phenyl]-1-piperazinyl]phenyl]-2-[2-[[1-(4-fluorophenyl)ethyl]amino]-1-methylpropyl]-2,4-dihydro-3H-1,2,4-triazol-3-one;

4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[[1-(phenylmethyl)-4-piperidinyl]amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-(4-morpholinyl)-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[[1-(hydroxymethyl)-2-phenylethyl]amino]-1-methylpropyl]-3H-1,2,4-triazol-3-one;

4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(2-hydroxy-1-phenylethyl)amino]-1-methylpropyl]-3H-1,2,4-triazol-3-one;

4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[2-(2-hydroxy-2-phenylethyl)amino]-1-methylpropyl]-3H-1,2,4-triazol-3-one;

4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[[1-(hydroxymethyl)-2-methylpropyl]amino]-1-methylpropyl]-3H-1,2,4-triazol-3-one;

4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(1-phenylethyl)amino]-1-methylpropyl]-3H-1,2,4-triazol-3-one;

4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[1-(1-phenylethyl)-4-piperidinyl]-3H-1,2,4-triazol-3-one;

4-[4-[4-[[2-(2,4-dichlorophenyl)-2-(1H-1,2,4-triazol-1-ylmethyl)-1,3-dioxolan-4-yl]-methoxy]phenyl]-1-piperazinyl]phenyl]-2,4-dihydro-2-[2-[[1-(hydroxymethyl)-2-methylpropyl]amino]-1-methylpropyl]-3H-1,2,4-triazol-3-one;

2-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-4-[2-[(phenylmethyl)amino]-1-methylpropyl]-3H-1,2,4,-triazol-3-one;

4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[4-[(phenylmethyl)amino]-cyclohexyl]-3H-1,2,4-triazol-3-one; the N-oxide forms, the pharmaceutically acceptable addition salts and stereochemically isomeric forms thereof.

Most preferred stereochemically pure compounds are

[2S-[2α,4α[(R*,S*)(S*)]]]-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[2-[(1-phenylethyl)amino]-1-methylpropyl]-3H-1,2,4-triazol-3-one;

[2S-[2α,4α(S*,R*)]]4-[4-[4-[4-[[2,4-diflourophenyl)-2-(1H-1,2,4-triazol-1-yl-methyl)-1,3-dioxolan-4-yl] methoxy]phenyl]-1-piperazinyl]phenyl]-2,4-dihydro-2-[2-[(phenylmethyl)amino]-1-methylpropyl]-3H-1,2,4,-triazol-3-one; and

[2S-[2α,4α[(R*,S*)(R*)]]]-4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[2-[[1-(hydroxymethyl)-2-methylpropyl]amino]-1-methylpropyl]-3H-1,2,4-triazol-3-one.

The compounds of the present invention wherein $R^6$ and $R^7$ are other than hydrogen, said $R^6$ and $R^7$ being represented by $R^{6'}$ and $R^{7'}$ and said compounds being represented by formula (I'), can be prepared by reacting an intermediate of formula (II) wherein $W^1$ is a suitable leaving group such as, for example, a halogen, e.g. iodo, an arylsulfonyloxy or an alkanesulfonyloxy group, e.g. p-toluenesulfonyloxy, naphtylsulfonyloxy or methanesulfonyloxy, with an intermediate of formula (III) in a reaction-inert solvent such as, for example, N,N-dimethylformamide, N,N-dimethylacetamide, 1-methyl-2-pyrrolidinone, 1,3-dimethyl-2-imidazolidinone, sulfolane or the like, and in the presence of a suitable base such as, for example, sodiumhydroxide or sodiumhydride.

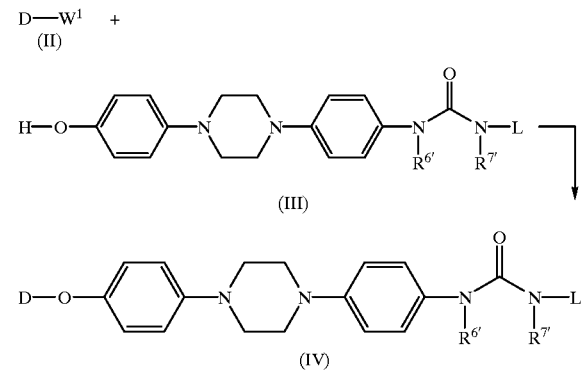

In this and the following preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak AD (amylose 3,5 dimethylphenyl carbamate) or Chiralpak AS, both purchased from Daicel Chemical Industries, Ltd, in Japan.

Compounds of formula (I') may also be prepared by N-alkylating an intermediate of formula (IV) with an intermediate of formula (V) wherein $W^2$ is a suitable leaving group such as, for example, a halogen, and wherein reactive amino groups in L such as primary and secondary amines, in case they are present, are protected with a protective group P such as, for example, a $C_{1-4}$alkyloxycarbonyl group, in a reaction-inert solvent such as, for example, dimethylsulfoxide, in the presence of a base such as, for example, potassium hydroxide. In case L was protected, art-known deprotection techniques can be employed to arrive at compounds of formula (I') after the N-alkylation reation.

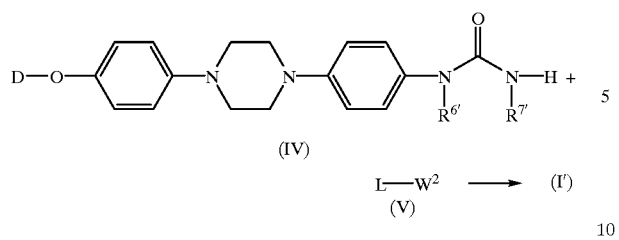

(IV)

L—W² → (I')
(V)

Compounds of formula (I') wherein L is a radical of formula (a), said compounds being represented by formula (I'-a), may be prepared by reacting an intermediate of formula (VI) wherein W³ is a suitable leaving group such as, for example, a halogen, an arylsulfonyloxy or an alkanesulfonyloxy group, e.g. p-toluenesulfonyloxy, naphtylsulfonyloxy or methanesulfonyloxy, with an intermediate of formula (VII) optionally in the presence of a suitable base such as, for example, sodium- or potassium carbonate, triethylamine or the like, and optionally in a reaction-inert solvent such as, for example, N,N-dimethylformamide, N,N-dimethyl-acetamide, 1-methyl-2-pyrrolidinone, 1,3-dimethyl-2-imidazolidinone, sulfolane or the like. In case $R^1$ and $R^2$ form together with the nitrogen atom to which they are attached an azido radical, $NaN_3$ may be used as intermediate of formula (VII).

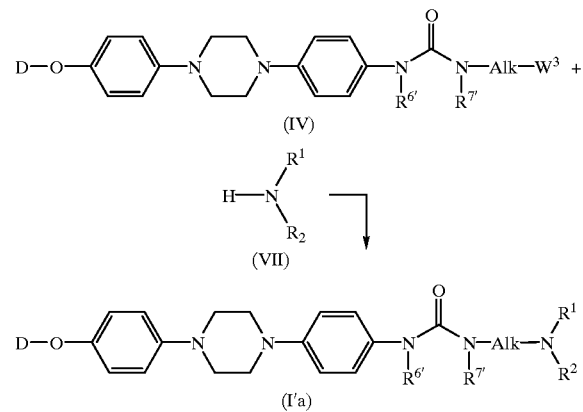

The compounds of formula (I) wherein at least one of $R^6$ or $R^7$ is hydrogen, said $R^6$ and $R^7$ being represented by $R^{6''}$ and $R^{7''}$ and said compounds being represented by formula (I''), can be prepared following the reaction procedure in scheme 1.

Scheme 1

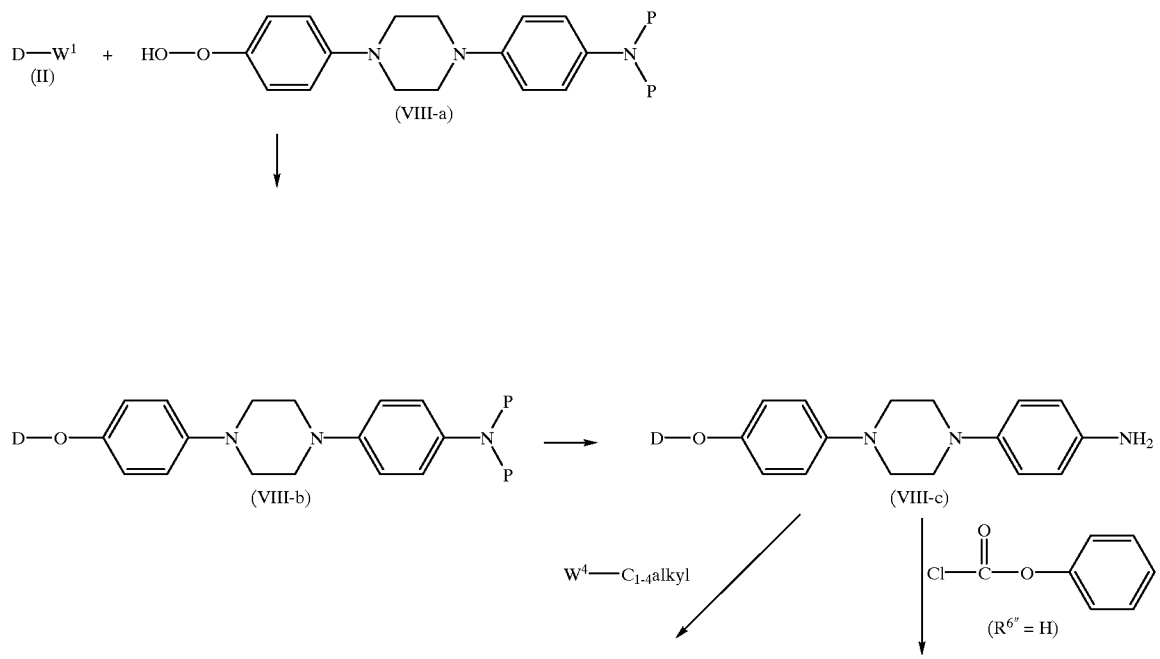

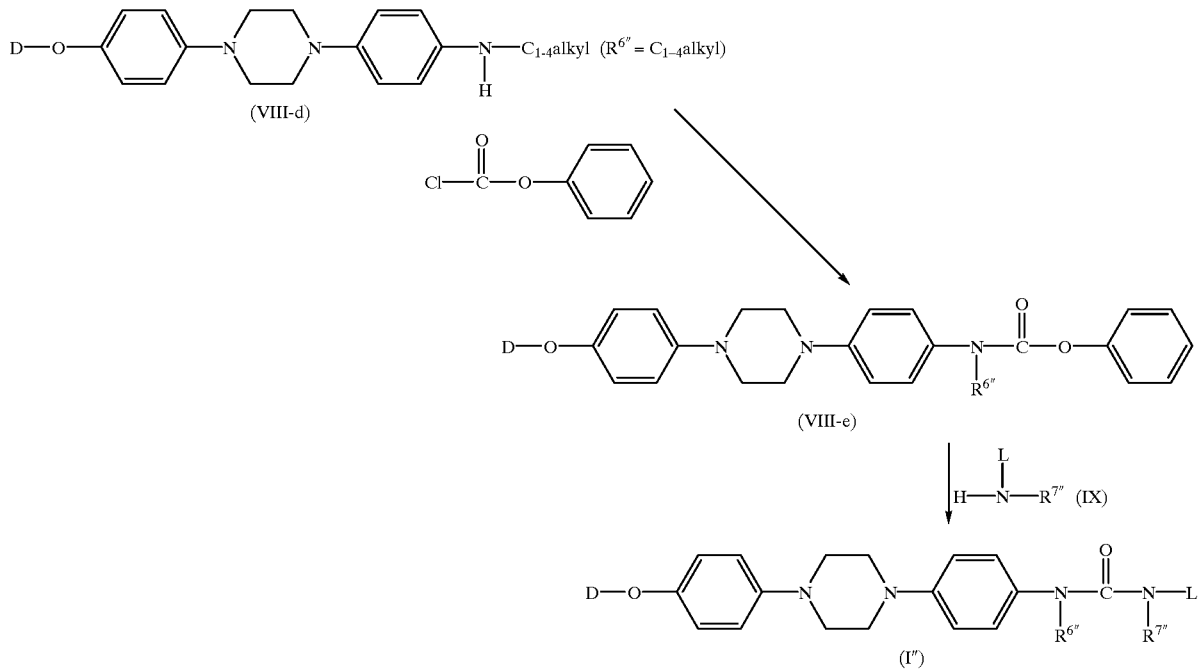

In scheme 1, the intermediates of formula (VIII-a) wherein $NP_2$ is a protected amino group wherein P is for example a $C_1$alkyloxycarbonyl group, or a functional derivative of $NP_2$ such as, for example, a nitro group, are reacted with an intermediate of formula (II) according to the procedure described for the preparation of compounds of formula (I'). The thus obtained intermediates of formula (VIII-b) may be deprotected according to art-known deprotection techniques, thus obtaining an amine derivative of formula (VIII-c). In case $NP_2$ is a nitro group, art-known reduction techniques may be used to obtain amines of formula (VIII-c). The amine derivatives of formula (VIII-c) can then be reacted with phenyl chloroformate or a functional derivative thereof. In order to obtain compounds of formula (I") wherein $R^{6''}$ is $C_{1-4}$alkyl, amine derivatives of formula (VII-c) may first be reacted with $C_{1-4}$alkyl-$W^4$ wherein $W^4$ is a suitable leaving group such as, for example, a halogen, and then reacted with phenyl chloroformate.

The thus obtained intermediates of formula (VIII-e) may be reacted with an intermediate of formula (IX) wherein reactive amino groups in L such as primary and secondary amines, in case they are present, are protected with a protective group P such as, for example, a $C_{1-4}$alkyloxycarbonyl group. Suitably, the reactive amino group may then be deprotected using art-known deprotection techniques to arrive at the desired compound of formula (I").

The compounds of formula (I) may also be converted into each other following art-known transformations.

For instance, compounds of formula (I') wherein L is a radical of formula (b), said compounds being represented by formula (I'-b), may be prepared using art-known acylation methods e.g., those described in "Principles of Peptide Synthesis", M. Bodanszky, Springer-Verlag Berlin Heidelberg, 1984.

A particular acylation procedure involves the acylation of a compound of formula (I'-a) wherein $R^1$ is hydrogen, said compounds being represented by formula (I'-a-1), with an intermediate of formula (X-b) wherein $W^5$ is a suitable leaving group such as, for example, a halogen or a hydroxy group, in the presence of a suitable base such as, for example, sodiumbicarbonate or N,N-dimethylaminopyridine or a functional derivative thereof, and in a reaction-inert solvent such as, for example, dichloromethane, dichloroethane, tetrahydrofuran or the like.

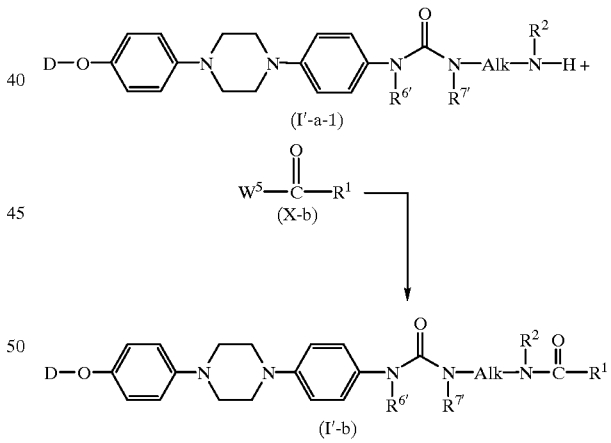

In case $W^5$ is hydroxy, it may be convenient to activate the carboxylic acid of formula (X-b) by adding a diimide such as, for example, N,N'dicyclohexylcarbodiimide; 1-(3-dimethylaminopropyl)-3-ethylcarbodiimide or a functional derivative thereof. Alternatively, the carboxylic acid of formula (X-b) may be activated by adding carbonyldiimidazole or a functional derivative thereof.

In case an chirally pure intermediate of formula (X-b) is used, fast and enantiomerization-free couplings may be performed by adding hydroxybenzotriazole, benzotriazolyloxytris(dimethylamino) phosphonium hexafluorophosphate, tetrapyrrolidinophosphonium hexafluorophosphate, bromotripyrrolidinophosphonium hexafluorophosphate or a functional derivative thereof (D. Hudson, J. Org. Chem., 1988, 53, p617 & 1999 Novabiochem catalogue & peptide Synthesis Handbook).

An analogous acylation procedure as for the preparation of compounds of formula (I'-b) may be used for the preparation of compounds of formula (I') wherein L is a radical of formula (c), said compounds being represented by formula (I'-c). In said analogous reaction procedure, the intermediate of formula (X-b) is replaced by a carbonate of formula $C_{1-4}$alkyl—O—C(=O)—O—$R^1$ (X-c-1), a chloroformate of formula Cl—C(=O)—O—$R^1$ (X-c-2) or $C_{1-4}$alkyl-O—C(=O)—O—C(=O)—O—$C_{1-4}$alkyl (X-c-3).

An analogous acylation procedure as for the preparation of compounds of formula (I'-b) may be used for the preparation of compounds of formula (I') wherein L is a radical of formula (d), said compounds being represented by formula (I'-d). In said analogous reaction procedure, the intermediate of formula (X-b) is replaced by an isocyanate of formula O=C=N—$R^1$ (X-d-1), an isothiocyanate of formula S=C=N—$R^1$ (X-d-2), a phenylcarbamate of formula phenyl-O—C(=O)—$NR^1R^2$ (X-d-3), a phenylthiocarbamate of formula phenyl-O—C(=S)—$NR^1R^2$ (X-d4), or an intermediate of formula $C_{1-4}$alkyl-S—C(=$NR^2$)—$NR^1R^2$ (X-d-5).

Compounds of formula (I'-a-1) may also be reductively N-alkylated with an aldehyde or keton of formula $R^{1a}C(=O)R^{1b}$ (XI) wherein $R^{1a}$ and $R^{1b}$ are so defined that the radical —$CHR^{1a}R^{1b}$ is encompassed by the definition of $R^1$, thus forming compounds of formula (I'-a-2). Said reductive N-alkylation may be performed in a reaction-inert solvent such as, for example, toluene, methanol, tetrahydrofuran or a mixture thereof, and in the presence of a reducing agent such as, for example, a borohydride, e.g. sodium borohydride, zinc borohydride, lithium borohydride, sodium reactants and the reaction products. Stirring and optionally elevated temperatures and/or pressure may enhance the rate of the reaction.

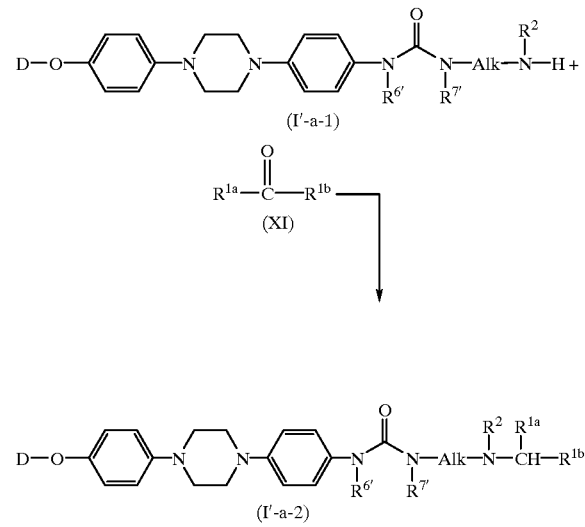

Compounds of formula (I') wherein L is a radical of formula (a) and $R^1$ is —$CH_2$—CH(OH)substituent wherein the substituent belongs to the group of substituents of $C_{1-4}$alkyl in the definition of $R^1$, said compounds being represented by formula (I'-a-3), may be prepared by reacting an intermediate of formula (I'-a-1) with an epoxide of formula (XII) in a reaction-inert solvent such as, for example, 2-propanol.

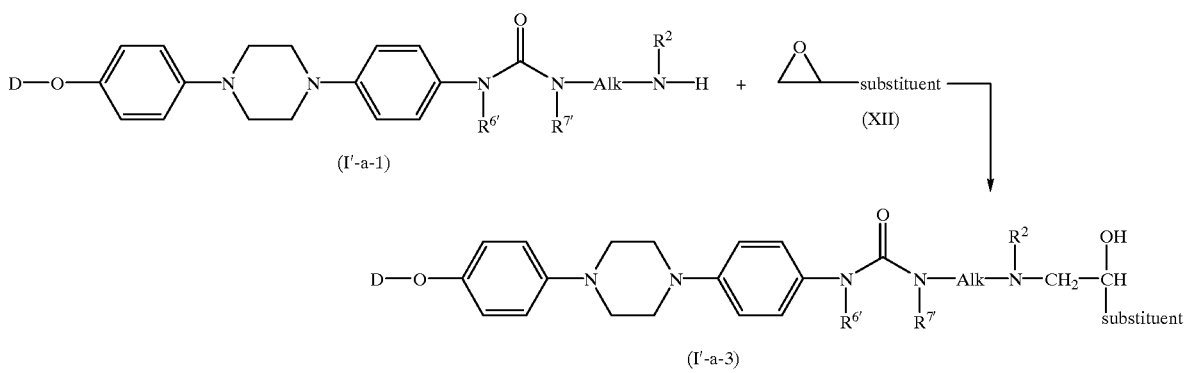

cyanoborohydride or triacetoxy borohydride. In case a borohydride is used as a reducing agent, it may be convenient to use a catalyst such as, for example, titanium(IV) isopropoxide as described in J. Org. Chem, 1990, 55, 2552–2554. It may also be convenient to use hydrogen as a reducing agent in combination with a suitable catalyst such as, for example, palladium-on-charcoal or platinum-on-charcoal. The formation of a Schiff base in the first step of the reductive N-alkylation can be enhanced by the addition of a suitable reagent to the reaction mixture such as, for example, aluminium tert-butoxide, calcium oxide, calcium hydride or a titanium(IV)alkoxide, e.g. titanium(IV)isopropoxide or titanium(IV)-n-butoxide. An appropriate catalyst-poison, e.g., thiophene, butanethiol or quinoline-sulphur, may also be added to the reaction mixture to prevent the undesired further hydrogenation of certain functional groups in the Compounds of formula (I) containing a $C_{1-4}$alkyloxycarbonylamino moiety may be converted to compounds of formula (I) containing the corresponding amino moiety using art-known techniques such as, for example, reaction in dichloromethane and in the presence of trifluoroacetic acid.

Compounds of formula (I') containing a primary amine may be mono-methylated by first protecting the primary amine with a suitable protecting group such as, for example, an arylalkyl group, e.g. benzyl, and subsequently methylating the secondary amine using art-known methylation techniques such as, for example, reaction with paraformaldehyde. The thus obtained tertiary amine may be deprotected using art-known deprotection techniques such as, for example, reaction with hydrogen in tetrahydrofuran or methanol and in the presence of a catalyst such as, for example palladium-on-charcoal, thus obtaining the desired methylated secondary amine.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the intermediates and starting materials used in the above reaction procedures are commercially available, or may be synthesized according to procedures described elsewhere, e.g. U.S. Pat. Nos. 4,791,111, 4,931,444 and 4,267,179. Some methods of preparing the intermediates of the present invention are described hereinbelow.

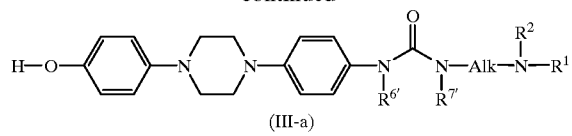

(III-a)

The above reaction procedure may be performed with chirally pure starting materials, employing stereoselective reaction procedures, thus obtaining chirally pure intermediates of formula (III-a). For instance, an stereoselective reductive amination of a chirally pure form of an intermediate of formula (XIII) with a chirally pure form of formula (VII) may be a reaction using hydrogen on palladium-on-charcoal as reducing agent in the presence of a thiophene solution and titanium(IV) isopropoxide. The resulting stereoisomeric forms may be separated using chromatographic or other art-known techniques.

It may also be convenient to perform the above reaction on the alkylphenoxy derivatives of the intermediates of formula (XIII).

Intermediates of formula (III-a) wherein $R^1$ is an aryl$C_{1-6}$alkyl group may be reduced using art-known reduction techniques such as, for example, a reduction with hydrogen in the presence of palladium on activated charcoal, thus obtaining intermediates of formula (III-a) wherein $R^1$ is hydrogen, said intermediates being represented by formula (III-a-1).

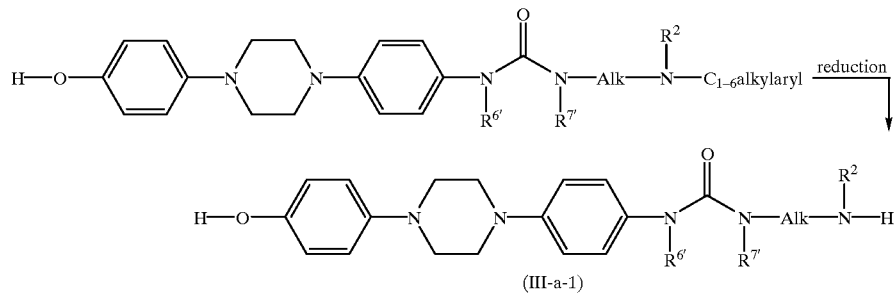

(III-a-1)

For instance, intermediates of formula (III) wherein L is a radical of formula (a), said intermediates being represented by formula (III-a), can be prepared by reductively aminating a carbonyl containing intermediate of formula (XIII) wherein Alk=O is the same as Alk substituted with an oxo group, with an intermediate of formula (VII) following the same reaction procedures as described for the reductive N-alkylation of compounds of formula (I'-a-1) with intermediates of formula (XI).

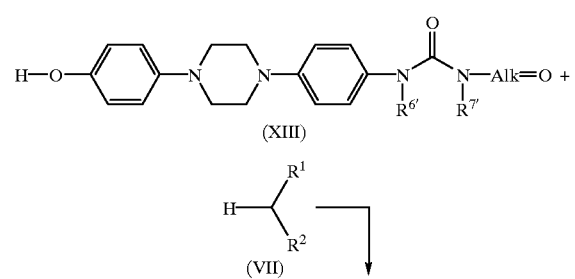

Said intermediates of formula (III-a-1) may be converted to intermediates of formula (III) wherein L is a radical of formula (b), (c) or (d), being represented by formula (III-b), (III-c) and (III-d) respectively, using art-known acylation methods e.g., those described in "Principles of Peptide Synthesis", M. Bodanszky, Springer-Verlag Berlin Heidelberg, 1984 and 1999 Novabiochem Catalogue & Peptide Synthesis Handbook.

Also, amides of formula (III-b) may be hydrolysed using a suitable acid such as, for example hydrochloric acid, thus obtaining intermediates of formula (III-a-1).

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromato-graphic techniques using chiral stationary phases. Said pure stereoisomeric forms may also be derived from the corresponding pure stereoisomeric forms of the appropriate starting materials, provided that the reaction occurs stereoselectively or stereospecifically. Preferably if a specific stereoisomer is desired, said compound will be synthesized by stereoselective or stereospecific methods of preparation. These methods will advantageously employ chirally pure starting materials. Stereoisomeric forms of the compounds of formula (I) are obviously intended to be included within the scope of the invention.

The chirally pure forms of the compounds of formula (I) form a preferred group of compounds. It is therefore that the chirally pure forms of the intermediates of formula (II), (III) and (VI), their N-oxide forms and their addition salt forms are particularly useful in the preparation of chirally pure compounds of formula (I). Also enantiomeric mixtures and diastereomeric mixtures of intermediates of formula (II), (III) and (VI) are useful in the preparation of compounds of formula (I) with the corresponding configuration. Said chirally pure forms and also the enantiomeric and diastereomeric mixtures of the intermediates of formula (III) are deemed novel.

A specific way to stereoselectively prepare intermediates of formula (III-a) wherein $R^1$ and $R^2$ are hydrogen and Alk is —CH(CH$_3$)—CH(CH$_3$)— wherein both asymmetric carbon atoms have the S-configuration, being represented by formula (SS)(III-a-2), or the alkoxyphenyl analogues thereof, is as depicted in scheme 2a.

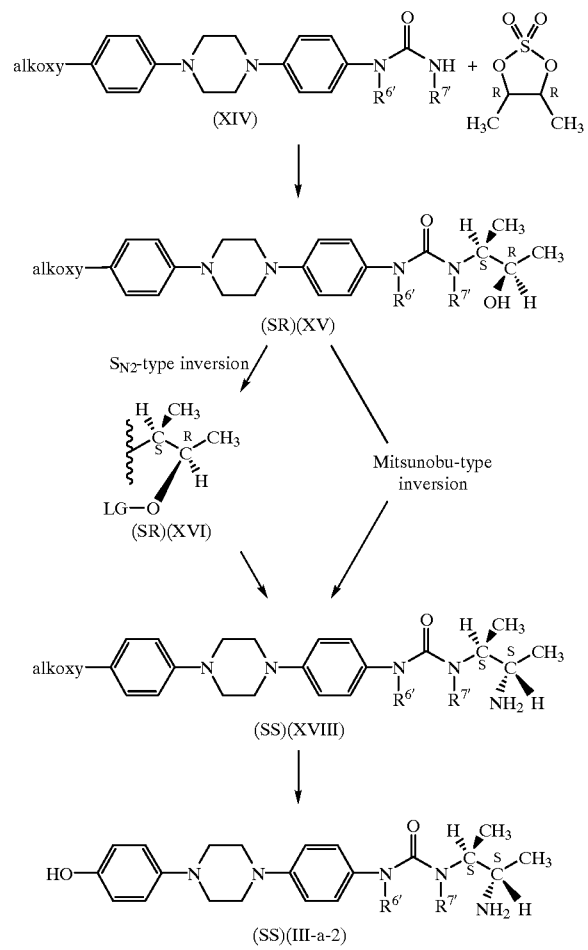

The reaction of an intermediate of formula (XIV) with (4R-trans)-4,5-dimethyl-2,2-dioxide-1,3,2-dioxathiolane may be performed in a suitable solvent, preferably a polar aprotic solvent such as, for example, dimethylacetamide or N,N-dimethylformamide, and in the presence of a base such as, for example, potassium tert-butanolate, potassium hydroxide or potassium hydride. Subsequently, an acid such as, sulfuric acid, may be added to the reaction mixture, thus obtaining an intermediate of formula (SR)(XV) whereby the 2-hydroxy-1-methylpropyl moiety has the erythro form. Then, the carbon atom bearing the alcohol function of said 2-hydroxy-1-methylpropyl moiety is epimerized, preferably 100% inverted, thus obtaining intermediate (SS)(XVII) whereby the 2-amino-1-methylpropyl moiety has the threo form. Two pathways are convenient.

A first pathway involves the transformation of the alcohol function into a suitable leaving group O-LG by, for instance, derivatizing the hydroxy group with an organic acid such as, for example, a sulfonic acid, e.g. p-toluenesulfonic acid or methane-sulfonic acid; thus obtaining an intermediate of formula (SR)(XVI). The carbon atom bearing the leaving group in said intermediate (SR)(XVI) may subsequently be epimerized, preferably 100% inverted, by a $S_{N2}$-type reaction with a suitable nucleophilic reagent such as, for example, NaN$_3$, which may subsequently be reduced to the primary amine of formula (SS)(XVII). Alternatively, the Gabriel synthesis, its Ing-Manske modification or another functional modification thereof may be employed to prepare a primary amine of formula (SS)(XVII).

An alternative pathway for inverting the stereochemistry of the carbon atom bearing the alcohol function is the use of the Mitsunobu reaction. The alcohol function of an intermediate of formula (SR)(XV) is activated with diisopropyl azodicarboxylate or a functional derivative thereof such as diethyl azodicarboxylate, in the presence of triphenylphosphine, and in a polar aprotic solvent such as, for example, dimethyl-acetamide or dimethylformamide. The thus obtained activated alcohol is subsequently reacted with an amide such as, for example, 2,2,2-trifluoroacetamide or a functional derivative thereof. The thus obtained amide whereby the 2-hydroxy-1-methylpropyl moiety has been transformed to the threo form may subsequently be hydrolysed using art-known hydrolysis techniques, thus obtaining an intermediate of formula (SS)(XVII).

In order to obtain intermediates of formula (SR)(XVII), an additional inversion step can be introduced as is depicted in scheme 2b.

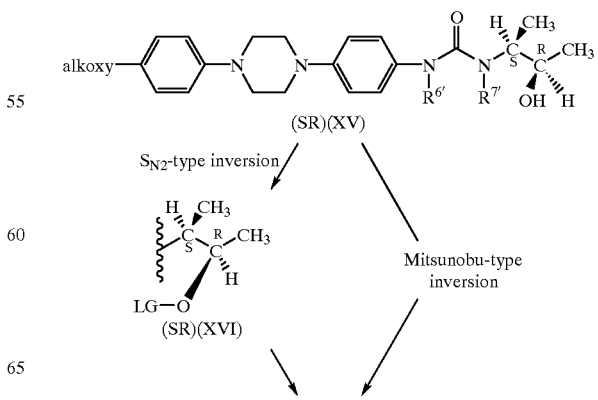

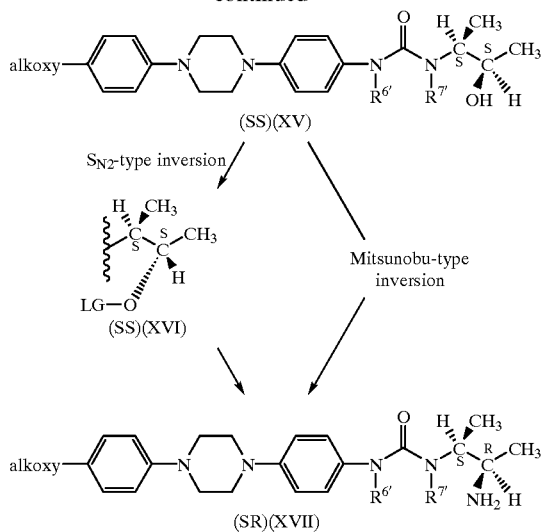

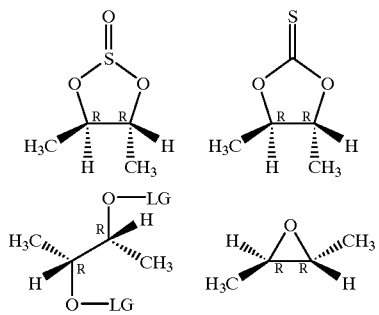

The intermediates of formula (SR)(XV) is converted to an intermediate of formula (SS)(XV) using two possible pathways. A first one involves the transformation of the alcohol function into a suitable leaving group O-LG as described hereinabove; thus obtaining an intermediate of formula (SR)(XVI). The carbon atom bearing the leaving group in said intermediate (SR)(XVI) may subsequently be epimerized, preferably 100% inverted, by a $S_{N2}$-type reaction with a suitable nucleophilic reagent such as, for example, a benzyloxy group; an hydroxy salt of an alkali metal, e.g. sodiumhydroxide or potassium hydroxide; an acetate, e.g. sodium acetate. Said reaction is performed in a suitable solvent, preferably a polar aprotic solvent such as, for example, dimethylacetamide, N-methylpyrrolidinone, dimethylimidazolidinone or sulfolane. In case an alcoholate or an acetate is used in the $S_{N2}$ reaction, the thus obtained intermediate may be deprotected using art-known deprotection techniques, thus obtaining an alcohol intermediate of formula (SS)(XV).

Another pathway involves the Mitsunobu reaction. The alcohol function of an intermediate of formula (SR)(XV) is activated as described hereinabove. The thus obtained activated alcohol is subsequently reacted with a carboxylic acid such as, for example, 4-nitrobenzoic acid, acetic acid, monochloroacetic acid. The thus obtained ester may subsequently be hydrolysed using art-known hydrolysis techniques, thus obtaining an intermediate of formula (SS)(XV).

The intermediates of formula (SS)(XV) may then be reacted to obtain intermediates of formula (SR)(XVII) using the same reaction pathways as described for the preparation of intermediates (SS)(XVII) starting from (SR)(XV).

Finally, the alkoxyphenyl moiety of the intermediates of formula (SS)(XVII) or (SR)(XVII) may be transformed to the phenol moiety using for instance, hydrobromic acid, or a mixture of hydrobromic acid and hydrobromic acid in acetic acid, in the presence of $NaHSO_3$, thus obtaining an intermediate of formula (SS)(III-a-2) or (SR)(III-a-2).

Suitable alternatives for (4R-trans)-4,5-dimethyl-2,2-dioxide-1,3,2-dioxathiolane include the following chirally pure intermediates:

wherein LG is a leaving group such as, for example, p-toluenesulfonyl.

The intermediates of formula (III-a-2), whereby the 2-hydroxy-1-methylpropyl moiety has the [R—(R*,R*)] form, said intermediates being represented by (RR)(III-a-2), may be prepared using the same reaction pathways as depicted in scheme 2 but replacing (4R-trans)-4,5-dimethyl-2,2-dioxide-1,3,2-dioxathiolane with its enantiomer (4S-trans)-4,5-dimethyl-2,2-dioxide-1,3,2-dioxathiolane.

Intermediates of formula (VI) can be prepared by reducing an intermediate of formula (XIII) and subsequently introducing a leaving group $W^3$. In particular, intermediates of formula (VI) wherein Alk is —CH(CH₃)—CH(CH₃)—, said intermediates being represented by formula (VI-a), may be prepared according to the reaction scheme as depicted in scheme 3. Optionally, the chirally pure intermediates of formula (VI-a), represented by (SS)(VI-a), (SR)(VI-a), (RS)(VI-a) and (RR)(VI-a), can be prepared using this procedure.

Scheme 3

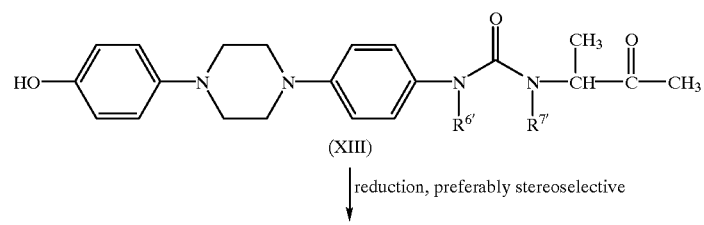

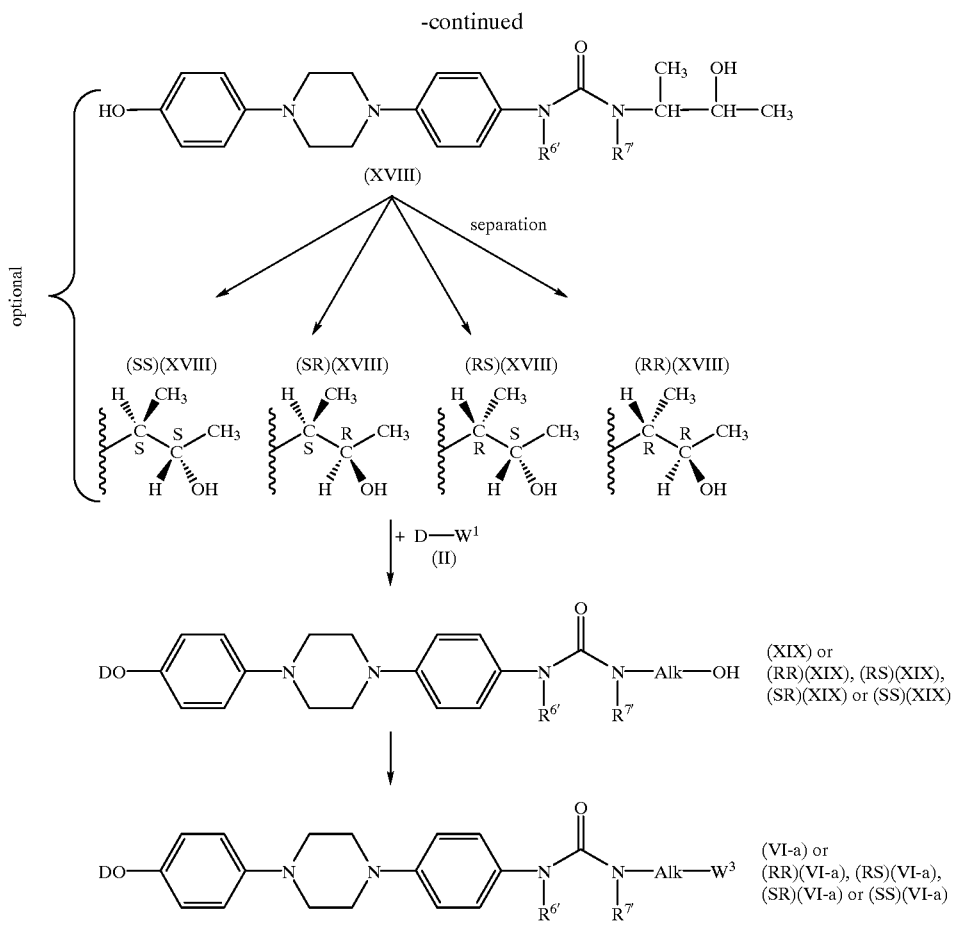

Suitable stereoselective reduction conditions include the use of K-selectride in a suitable solvent such as, for example, dimethylacetamide or tetrahydrofuran; the use of sodium-borohydride optionally in combination with $CeCl_3 \cdot 7H_2O$, $ZnCl_2$ or $CaCl_2 \cdot 2H_2O$ in a suitable solvent such as, for example, dimethylacetamide, dimethylformamide, methanol or tetrahydrofuran. Said reduction conditions favour the threo form of the 2-hydroxy-1-methylpropyl moiety, i.e. the form where the two asymmetric carbon atoms have identical absolute configuration. Recrystallisation of the obtained intermediate of formula (XVIII) after stereoselective reduction may even further improve the ratio threo/erythro in favor of the threo form. The desired stereoisomeric forms of the intermediates of formula (XVIII), being (RR)(XVIII), (SS)(XVIII), (RS)(XVIII) and (SR)(XVIII), can then optionally be isolated chromatographically using a chiral stationary phase such as, for example, Chiralpak AD (amylose 3,5-dimethylphenyl carbamate) purchased from Daicel Chemical Industries, Ltd, in Japan. The intermediate of formula (XVIII) or one or more of its stereoisomeric forms, may then be further reacted with an intermediate of formula (II) as described hereinabove for the general preparation of compounds of formula (I'). Finally, the hydroxy group of the thus obtained intermediates of formula (XIX) or a chirally pure form thereof, may be transformed into a suitable leaving group $W^3$ by, for instance, derivatizing the hydroxy group with an organic acid such as, for example, a sulfonic acid, e.g. p-toluenesulfonic acid or methanesulfonic acid; thus obtaining an intermediate of formula (VI-a) or a chirally pure form thereof.

The compounds of formula (I), the pharmaceutically acceptable addition salts and the stereochemically isomeric forms thereof are useful agents for combating fungi in vivo. The present compounds are broad-spectrum antifungals. They are active against a wide variety of fungi, such as Candida spp., e.g. *Candida albicans, Candida glabrata, Candida krusei, Candida parapsilosis, Candida kefyr, Candida tropicalis;* Aspergillus spp., e.g. *Aspergillus fumigatus, Aspergillus niger, Aspergillus flavus; Cryptococcus neoformans; Sporothrix schenckii*; Fonsecaea spp.; *Epidermophyton floccosum; Microsporum canis*; Trichophyton spp.; Fusarium spp.; and several dematiaceous hyphomycetes. Of particular interest is the improved activity of some of the present compounds against Fusarium spp.

In vitro experiments, including the determination of the fungal susceptibility of the present compounds as described in the pharmacological example hereinafter, indicate that the compounds of formula (I) have a favourable intrinsic inhibitory capacity on fungal growth in for instance *Candida albicans*. Other in vitro experiments such as the determination of the effects of the present compounds on the sterol synthesis in, for instance, *Candida albicans*, also demonstrate their antifungal potency. Also in vivo experiments in several mouse, guinea-pig and rat models show that, after both oral and intravenous administration, the present compounds are potent antifungals.

An additional advantage of some of the present compounds is that they are not only fungistatic, as most of the known azole antifungals, but are also fungicidal at acceptable therapeutic doses against many fungal isolates.

The compounds of the present invention are chemically stable and have a good oral availability.

The solubility profile in aqueous solutions of the compounds of formula (I) makes them suitable for intravenous administration. Particularly interesting compounds are those compounds of formula (I) having a water-solubility of at least 0.1 mg/ml at a pH of at least 4, preferably, a water-solubility of at least 1 mg/ml at a pH of at least 4, and more preferred a water-solubility of 5 mg/ml at a pH of at least 4.

In view of the utility of the compounds of formula (I), there is provided a method of treating warm-blooded animals, including humans, suffering from fungal infections. Said method comprises the systemic or topical administration of an effective amount of a compound of formula (I), a N-oxide form, a pharmaceutically acceptable addition salt or a possible stereoisomeric form thereof, to warm-blooded animals, including humans. Hence, compounds of formula (I) are provided for use as a medicine, in particular, the use of a compound of formula (I) in the manufacture of a medicament useful in treating fungal infections is provided.

The present invention also provides compositions for treating or preventing fungal infections comprising a therapeutically effective amount of a compound of formula (I) and a pharmaceutically acceptable carrier or diluent.

In view of their useful pharmacological properties, the subject compounds may be formulated into various pharmaceutical forms for administration purposes. To prepare the pharmaceutical compositions of this invention, a therapeutically effective amount of a particular compound, in base or addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, topically, percutaneously, transungually or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. As appropriate compositions for topical application there may be cited all compositions usually employed for topically administering drugs e.g. creams, gel, dressings, shampoos, tinctures, pastes, ointments, salves, powders and the like. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

Transungual compositions are in the form of a solution and the carrier optionally comprises a penetration enhancing agent which favours the penetration of the antifungal into and through the keratinized ungual layer of the nail. The solvent medium comprises water mixed with a co-solvent such as an alcohol having from 2 to 6 carbon atoms, e.g. ethanol.

For parenteral compositions, the carrier will usually comprise sterile water, at least in large part. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. For parenteral compositions, other ingredients, to aid solubility for example, e.g. cyclodextrins, may be included.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy) propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles obtainable by melt-extruding a mixture comprising a compound of formula (I) and an appropriate water-soluble polymer and subsequently milling said melt-extruded mixture. Said particles can then be formulated by conventional techniques into pharmaceutical dosage forms such as tablets and capsules.

Said particles consist of a solid dispersion comprising a compound of formula (I) and one or more pharmaceutically acceptable water-soluble polymers. The preferred technique for preparing solid dispersions is the melt-extrusion process comprises the following steps:

a) mixing a compound of formula (I) and an appropriate water-soluble polymer, b) optionally blending additives with the thus obtained mixture, c) heating the thus obtained blend until one obtains a homogenous melt, d) forcing the thus obtained melt through one or more nozzles; and e) cooling the melt till it solidifies.

The solid dispersion product is milled or ground to particles having a particle size of less than 600 μm, preferably less than 400 μm and most preferably less than 125 μm.

The water-soluble polymers in the particles are polymers that have an apparent viscosity of 1 to 100 mPa.s when dissolved in a 2% aqueous solution at 20° C. solution. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, polysaccharides, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

A more novel type of substituted cyclodextrins is sulfobutylcyclodextrines.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1.

It may further be convenient to formulate the present azole antifungals in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and an antifungal agent and a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The pharmaceutical compositions mentioned above may also contain a fungicidally effective amount of other antifungal compounds such as cell wall active compounds. The term "cell wall active compound", as used herein, means any compound which interferes with the fungal cell wall and includes, but is not limited to, compounds such as papulacandins, echinocandins, and aculeacins as well as fungal cell wall inhibitors such as nikkomycins, e.g. nikkomycin K and others which are described in U.S. Pat. No. 5,006,513.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in treating warm-blooded animals suffering from diseases caused by fungi could easily determine the therapeutically effective daily amount from the test results given herein. In general, it is contemplated that a therapeutically effective daily amount would be from 0.05 mg/kg to 20 mg/kg body weight.

EXPERIMENTAL PART

Hereinafter, "DMF" is defined as N,N-dimethylformamide, "THF" is defined as tetrahydrofuran and "DIPE" is defined as diisopropylether.

A. PREPARATION OF THE INTERMEDIATES

EXAMPLE A1 a) A mixture of (±)-2,4-dihydro-4-[4-[4-(4-hydroxyphenyl)-1-piperazinyl]phenyl]-2-(1-methyl-2-oxopropyl)-3H-1,2,4-triazol-3-one (0.05 mol) and (+)-(R)-α-methyl-benzenemethanamine (0.1 mol) in THF (500 ml) was hydrogenated at 50° C. for 48 hours with Pd/C 10% (10 g) as a catalyst in the presence of titanium(IV) n-butoxide (28.4 g) and thiophene solution (10 ml). The catalyst was filtered off. Pd/C 10% (10 g) was added again. Hydrogenation was continued at 50° C. for 48 hours. After uptake of $H_2$, the mixture was cooled, then the catalyst was filtered off and the filtrate was evaporated. The residue was stirred in $CH_2Cl_2$ (500 ml) and $H_2O$ (50 ml) was added. The mixture was acidified with a concentrated HCl solution, alkalized with a concentrated $NH_4OH$ solution and filtered over dicalite. The organic layer was separated, dried, filtered and the solvent was evaporated. The residue was triturated in DIPE, filtered off and dried, yielding 23.5 g (91%) of

[(R*,R*)(R)+(R*,S*)(R)]-2,4-dihydro-4-[4-[4-(4-hydroxyphenyl)-1-piperazinyl]phenyl]-2-[2-[(1-phenylethyl)amino]-1-methylpropyl]-3H-1,2,4-triazol-3-one (interm. 1).

b) A mixture of (±)-2,4-dihydro-4-[4-[4-(4-hydroxyphenyl)-1-piperazinyl]phenyl]-2-(1-methyl-2-oxopropyl)-3H-1,2,4-triazol-3-one (0.05 mol) and (−)-(S)-α-methyl-benzenemethanamine (0.1 mol) in THF (500 ml) was hydrogenated at 50° C. for 48 hours with Pd/C 10% (3 g) as a catalyst in the presence of titanium(VI) n-butoxide (28.4 g) and thiophene solution (3 ml). The catalyst was filtered off. Pd/C 10% (10 g) and thiophene solution (10 ml) were added again. Hydrogenation was continued at 50° C. for 48 hours. After uptake of $H_2$, the catalyst was filtered off and the filtrate was evaporated. The residue was stirred in $CH_2Cl_2$, $CH_3OH$ and $H_2O$. The mixture was alkalized with NaOH and filtered over dicalite. The organic layer was separated, dried, filtered and the solvent was evaporated. The residue was triturated in DIPE, filtered off and dried, yielding 19 g (74%) of [(R*,R*)(S)+(R*,S*)(S)]-2,4-dihydro-4-[4-[4-(4-hydroxyphenyl)-1-piperazinyl]phenyl]-2-[2-[(1-phenylethyl)amino]-1-methylpropyl]-3H-1,2,4-triazol-3-one (interm. 2).

c) A mixture of (±)-2,4-dihydro-4-[4-[4-(4-hydroxyphenyl)-1-piperazinyl]phenyl]-2-(1-methyl-2-oxopropyl)-3H-1,2,4-triazol-3-one (0.018 mol), (S)-α-methyl-1-naphthalenemethanamine (0.0187 mol) and sodium tris(acetato-O)hydroborate (I-) (0.028 mol) in $CH_2Cl_2$ (150 ml) was stirred at room temperature overnight. A diluted $NH_4OH$ solution was added. The mixture was stirred for 1 hour. The precipitate was filtered off, washed with $H_2O$ and with $CH_2Cl_2$ (20 ml) and dried. The residue was crystallized from $CH_3CN$. The precipitate was filtered off and dried, yielding 3.3 g (32%) of [R-(R*,S*)(S*)]-2,4-dihydro-4-[4-[4-(4-hydroxyphenyl)-1-piperazinyl]phenyl]-2-[1-metyl-2-[[1-(1-naphthalenyl)ethyl]amino]propyl]-3H-1,2,4-triazol-3-one (interm. 108).

d) A mixture of intermediate 5 (0.0049 mol), 3-pyridinecarboxaldehyde (0.0054 mol) and sodium tris (acetato-O)hydroborate (I-) (0.0049 mol) in $CH_2Cl_2$ (150 ml) was stirred at room temperature for the weekend. Sodium tris(acetato-O)hydroborate (I-) (0.0022 mol) was added again. The mixture was stirred at room temperature for 2 nights, extracted with $CH_2Cl_2$ and washed with $H_2O$. The organic layer was separated, dried, filtered and the solvent was evaporated. The residue was purified by flash column chromatography over silica gel (eluent: $CH_2Cl_2$/$CH_3OH$ 97/3). The pure fractions were collected and the solvent was evaporated, yielding 0.8 g of [R-(R*,S*)]-2,4-dihydro-4-[4-[4-(4-hydroxyphenyl)-1-piperazinyl]phenyl]-2-[1-methyl-2-[(3-pyridinylmethyl)amino]propyl]-3H-1,2,4-triazol-3-one (interm. 123).

e) A mixture of intermediate 5 (0.042 mol) and benzaldehyde (0.042 mol) in tetrahydrofuran (50 ml) was hydrogenated at 50° C. with palladium on activated carbon 10% (2 g) as a catalyst in the presence of a 4% thiophene solution (1 ml). After uptake of hydrogen (1 equiv), the catalyst was filtered off and the filtrate was evaporated. The residue was purified by column chromatography over silica gel (eluent 1: $CH_2Cl_2$/$CH_3OH$ 98/2, eluent 2: $CH_2Cl_2$/($CH_3OH/NH_3$) 95/5). The desired fraction was collected and the solvent was evaporated. The residue was triturated in 2-propanol, filtered off and dried, yielding 15 g (71%) of [R-(R*,S*)]-2,4-dihydro-4-[4-[4-(4-hydroxyphenyl)-1-piperazinyl]phenyl] 2-[1-methyl-2-[(phenylmethyl)amino]propyl]-3H-1,2,4-triazin-3-one (. 107).

Table 1a lists intermediates which are made according to the above example A1a.

TABLE 1a

| Int. No. | —NR¹R² | $R_a$ | $R_b$ | stereochemistry if not racemic; optical rotation as $[\alpha]_{20}^D$ @ concentration (in mg/5 ml DMF); salts and melting point (in ° C.) |
|---|---|---|---|---|
| 1 | —NH—CH(CH₃)-phenyl | CH₃ | H | [(R*,R*)(R) + (R*,S*)(R)] |
| 21 | —N(CH₃)₂ | CH₃ | H | (R*,S*) |
| 22 | —NH—CH₃ | CH₃ | H | [(R*,R*) + (R*,S*)] |
| 23 | —NH—(CH₂)₂-phenyl | CH₃ | H | [(R*,R*) + (R*,S*)] |
| 24 | —N(piperazinyl)-phenyl | CH₃ | H | — |
| 25 | —NH—CH₂-phenyl | CH₃ | H | (R*,R*) |
| 26 | —NH—CH₂-phenyl | CH₃ | H | (R*,S*) |
| 27 | —NH—CH₂-(tetrahydrofuranyl) | CH₃ | H | — |
| 28 | —N(CH₃)—(CH₂)₂—OH | CH₃ | H | — |
| 29 | —NH—(CH₂)₃-phenyl | CH₃ | H | — |
| 30 | —NH—CH₂-(2-fluorophenyl) | CH₃ | H | — |
| 31 | —NH—CH(CH₃)₂ | CH₃ | H | — |

TABLE 1a-continued

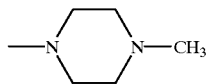

| Int. No. | —NR¹R² | $R_a$ | $R_b$ | stereochemistry if not racemic; optical rotation as $[\alpha]_{20}^D$ @ concentration (in mg/5 ml DMF); salts and melting point (in ° C.) |
|---|---|---|---|---|
| 32 | —NH—(CH$_2$)$_2$—O-phenyl | CH$_3$ | H | — |
| 33 | —NH—CH$_2$-(2-methoxyphenyl) | CH$_3$ | H | — |
| 34 | —NH—CH$_2$-(2-pyridinyl) | CH$_3$ | H | — |
| 35 | —NH—CH(i.propyl)-CH$_2$OH | CH$_3$ | H | [(R*,R*)(S)] + [(R*,S*)(S)] |
| 36 | 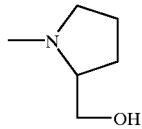 | CH$_3$ | H | (A) |
| 37 | —NH—CH(CH$_3$)-(4-fluorophenyl) | CH$_3$ | H | — |
| 38 | —NH—(CH$_2$)$_2$—OH | CH$_3$ | H | — |
| 39 | —NH—CH(CH$_3$)-(4-fluorophenyl) | CH$_3$ | H | [A,(S)]; −87.26° @ 25.90 |
| 40 | —NH—CH(CH$_3$)-(4-fluorophenyl) | CH$_3$ | H | [B,(S)]; −9.72° @ 25.20 |
| 41 | —NH—CH(CH$_2$OH)(phenyl) | CH$_3$ | H | [A,(S)]; +3.18° @ 25.15 |
| 42 | —NH—CH(CH$_2$OH)(phenyl) | CH$_3$ | H | [B,(S)]; +86.5° @ 24.97 |
| 43 | —NH—CH(CH$_2$OH)(phenyl) | CH$_3$ | H | [A,(R)]; −85.80° @ 24.71 |
| 44 | —NH—CH(CH$_2$OH)(phenyl) | CH$_3$ | H | [B,(R)]; −1.65° @ 24.27 |
| 45 | 1-morpholinyl | CH$_3$ | H | — |
| 46 | 4-(2-hydroxyethyl)-1-piperazinyl | CH$_3$ | H | — |
| 47 | —NH—CH(CH$_2$OH)(CH$_2$-phenyl) | CH$_3$ | H | [A,(S)] |
| 48 | —NH—CH(CH$_2$OH)(CH$_2$-phenyl) | CH$_3$ | H | [A,(R)]; +51.75° @ 25.41 |
| 49 | —NH—(CH$_2$)$_3$—N(CH$_3$)$_2$ | CH$_3$ | H | — |
| 50 | 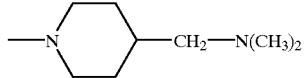 | CH$_3$ | H | [(A + B)(S)] |
| 51 | 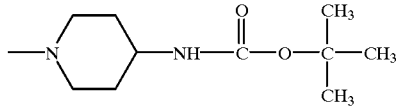 | CH$_3$ | H | — |
| 52 | 1-pyrrolidinyl | CH$_3$ | H | (A) |
| 53 | —NH—(CH$_2$)$_3$—NH—CH$_2$-phenyl | CH$_3$ | H | — |
| 54 | —N(CH$_3$)—(CH$_2$)$_3$—N(CH$_3$)$_2$ | CH$_3$ | H | — |
| 55 | 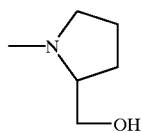 | CH$_3$ | H | — |
| 56 | 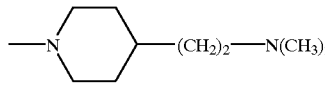 | CH$_3$ | H | [(A + B)(R)] |
| 57 | 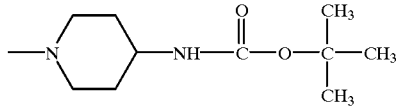 | CH$_3$ | H | — |
| 58 | —NH—(CH$_2$)$_2$—N(CH$_3$)$_2$ | CH$_3$ | H | — |

TABLE 1a-continued

[Structure: R_bO-phenyl-N(piperazine)N-phenyl-N(triazolone)-N-CH(R_a)-CH(CH_3)-N(R^1)-R^2]

| Int. No. | —NR¹R² | R_a | R_b | stereochemistry if not racemic; optical rotation as $[\alpha]_{20}^D$ @ concentration (in mg/5 ml DMF); salts and melting point (in °C.) |
|---|---|---|---|---|
| 59 | [1-methyl-4-(N,N-dimethylamino)piperidine] | CH₃ | H | (A) |
| 60 | —NH—(CH₂)₂—O—CH₂-phenyl | CH₃ | H | — |
| 61 | —NH—CH₂-[2-(HO—CH₂)phenyl] | CH₃ | H | — |
| 62 | —NH—CH(CH₃)-[4-F-phenyl] | CH₃ | H | [A(R)]; +87.91 @ 24.06; mp 215.4 |
| 63 | —NH—CH(CH₃)-[4-F-phenyl] | CH₃ | H | [B(R)]; +7.62 @ 24.27; mp 171.8 |
| 64a | —NH—CH[CH(CH₃)₂]—CH₂—OH | CH₃ | H | [R-(R*,R*)(S*)]; +8.93 @ 23.52 |
| 64b | —NH—CH[CH(CH₃)₂]—CH₂—OH | CH₃ | H | [S-(R*,R*)(S*)] −10.81 @ 10.18 |
| 65a | —NH—CH[CH(CH₃)₂]—CH₂—OH | CH₃ | H | [S-(R*,S*)(R*)]; −46.42 @ 24.56 |
| 65b | —NH—CH[CH(CH₃)₂]—CH₂—OH | CH₃ | H | [R-(R*,S*)(R*)] +45.42 @ 24.33 |
| 66a | —NH—CH[CH(CH₃)₂]—CH₂—OH | CH₃ | H | [R-(R*,S*)(S*)]; +47.33 @ 23.98 |
| 66b | —NH—CH[CH(CH₃)₂]—CH₂—OH | CH₃ | H | [S-(R*,S*)(S*)]; −49.06 @ 24.36 |
| 67a | —NH—CH[CH(CH₃)₂]—CH₂—OH | CH₃ | H | [S-(R*,R*)(R*)]; −14.03 @ 9.98 |
| 67b | —NH—CH[CH(CH₃)₂]—CH₂—OH | CH₃ | H | [R-(R*,R*)(R*)]; +11.95 @ 24.26 |
| 68 | —NH—CH₂-phenyl | CH₃ | H | (R*,R*) |
| 69 | —NH—CH₂-phenyl | CH₃ | H | (R*,S*) |
| 70 | [N-methyl-1,2,3,4-tetrahydronaphthalen-1-ylamine] | CH₃ | H | (B) |
| 71 | [N-methyl-1,2,3,4-tetrahydronaphthalen-1-ylamine] | CH₃ | H | (A) |
| 72 | [2-((dimethylamino)methyl)-N-methylbenzylamine] | CH₃ | H | — |
| 73 | —NH—CH(CH₃)(phenyl) | H | CH₃ | [2A(S)]; −46.60° @ 24.68; mp 160.3 |
| 74 | —NH—CH(CH₃)(phenyl) | H | CH₃ | [2B(R)]; +47.48° @ 22.85; mp 161.4 |
| 75 | [N-methyl-indan-1-ylamine] | CH₃ | CH₃ | — |

TABLE 1a-continued

[Structure: $R_b O$—phenyl—N(piperazine)N—phenyl—N(triazolone with C=O)—N—CH($R_a$)—CH($CH_3$)—N($R^1$)—$R^2$]

| Int. No. | —NR¹R² | $R_a$ | $R_b$ | stereochemistry if not racemic; optical rotation as $[\alpha]_{20}^D$ @ concentration (in mg/5 ml DMF); salts and melting point (in °C.) |
|---|---|---|---|---|
| 77 | (1-NH-2-OH-indane) | CH₃ | CH₃ | [1S-(1R*,2S*)] |
| 78 | (1-NH-2-OH-indane) | CH₃ | CH₃ | [1R-(1R*,2S*)] |
| 79 | —NH—CH₂-phenyl | CH₃ | H | [(R*,R*) + (R*,S*)] |
| 80 | —NH—CH₂-phenyl | CH₃ | H | (R*,R*) |
| 81 | —NH—CH₂-phenyl | CH₃ | H | (R*,S*) |
| 82 | —HN-(2-indanyl) | CH₃ | H | — |
| 83 | —NH—CH(CH₂OH)₂ | CH₃ | H | — |
| 84 | —NH—CH₂-phenyl | C₂H₅ | H | (B) |

EXAMPLE A2 a) A mixture of intermediate (1) (0.0457 mol) in THF (400 ml) was hydrogenated at 50° C. with Pd/C 10% (5 g) as a catalyst. After uptake of H₂, H₂O and CH₂Cl₂ were added, then the catalyst was filtered off and the filtrate was evaporated. The residue was triturated in CH₂Cl₂, filtered off and dried, yielding 14 g (75%) of (±)-[(R*,R*)+(R*,S*)]-2-(2-amino-1-methylpropyl)-2,4-dihydro-4-[4-[4-(4-hydroxyphenyl)-1-piperazinyl]phenyl]-3H-1,2,4-triazol-3-one (interm. 3).

b) A mixture of intermediate (3) (0.025 mol) and acetic anhydride (0.03 mol) in CH₂Cl₂ (300 ml) was stirred at room temperature. A mixture of NaHCO₃ (5 g) in H₂O (100 ml) was added. The mixture was stirred for 2 hours and CH₃OH was added. The organic layer was separated, dried, filtered and the solvent was evaporated. The residue was purified by HPLC over silica gel (eluent: CH₂Cl₂/CH₃OH 97/3 to 90/10). Two pure fractions were collected and their solvents were evaporated.

A first fraction was separated into its enantiomers by column chromatography (eluent: ethanol/2-propanol 50/50; column: CHIRALPAK AS). Two pure fractions were collected and their solvents were evaporated. The residue was triturated in 2-propanol, filtered off and dried, yielding 0.37 g (3.2%) of [R(R*,R*)]-N-[2-[4,5-dihydro-4-[4-[4-(4-hydroxyphenyl)-1-piperazinyl]phenyl]-5-oxo-1H-1,2,4-triazol-1-yl]-1-methylpropyl]acetamide (interm. 4a) and 2.81 g (25%) [S(R*,R*)]-N-[2-[4,5-dihydro-4-[4-[4-(4-hydroxyphenyl)-1-piperazinyl]phenyl]-5-oxo-1H-1,2,4-triazol-1-yl]-1-methylpropyl]acetamide (interm. 4b).

The second fraction was separated into its enantiomers by column chromatography (eluent:hexane/2-propanol/CH₃OH 30/55/15; column: CHIRALPAK AD). Two pure fractions were collected and their solvents were evaporated. The residue was triturated in 2-propanol, filtered off and dried, yielding 0.47 g (4%) of [S(R*,S*)]-N-[2-[4,5-dihydro-4-[4-[4-(4-hydroxyphenyl)-1-piperazinyl]phenyl]-5-oxo-1H-1,2,4-triazol-1-yl]-1-methylpropyl]acetamide (interm. 4c) and 3.21 g (28%) of [R(R*,S*)]-N-[2-[4,5-dihydro-4-[4-[4-(4-hydroxyphenyl)-1-piperazinyl]phenyl]-5-oxo-1H-1,2,4-triazol-1-yl]-1-methylpropyl]acetamide (interm. 4; mp. 264.3° C.); $[\alpha]_{20}^D$=+10.96° @ 20.07 mg/2 ml in DMF.

c) A mixture of intermediate (4) (0.0069 mol) in HCl conc. (50 ml) was stirred and refluxed for 48 hours. The solvent was evaporated and the residue was dissolved in H₂O (50 ml). The mixture was alkalized with NH₄OH and extracted with CH₂Cl₂/CH₃OH 80/20 (500 ml). The organic layer was separated, dried, filtered and the solvent was evaporated. The residue was triturated in 2-propanol, filtered off and dried, yielding 2.6 g (92%) of [R(R*,S*)]-2-(2-amino-1-methylpropyl)-2,4-dihydro-4-[4-[4-(4-hydroxyphenyl)-1-piperazinyl]phenyl]-3H-1,2,4-triazol-3-one (interm. 5; mp. 237.2° C.; $[\alpha]_{20}^D$=+1.01° @ 19.79 mg/2 ml in DMF).

d) A mixture of intermediate (5) (0.0061 mol) and bis(1,1-dimethylethyl) dicarbonate (0.008 mol) in CH₂Cl₂ (500 ml) was stirred and refluxed for 2 hours. Bis(1,1-dimethylethyl) dicarbonate (0.008 mol) was added again. The mixture was stirred and refluxed for 2 hours. The solvent was evaporated and the residue was triturated in DIPE, filtered off and dried, yielding 3.1 g (100%) of 1,1-dimethylethyl [R(R*,S*)]-[2-[4-[4-4-(4-hydroxyphenyl)-1-piperazinyl]phenyl]4,5-dihydro-5-oxo-1H-1,2,4-triazol-1-yl]-1-methylpropyl]carbamate (interm. 6; mp. 218.3° C.; $[\alpha]_{20}^{D}$=+19.63° @ 20.27 mg/2 ml in DMF).

EXAMPLE A3 a) Intermediate (1) (0.53 mol) was separated by HPLC over silica gel (eluent: $CH_2Cl_2/CH_3OH$ 2-propanol 99/1 to 97/3). Five fractions were collected and their solvents were evaporated. A first fraction was triturated in DIPE, filtered off and dried, yielding 78.5 g (29%) of [R(R*,R*)(R*)]-2,4-dihydro-4-[4-[4-(4-hydroxyphenyl)-1-piperazinyl]phenyl]-2-[2-[(1-phenylethyl)amino]-1-methylpropyl]-3H-1,2,4-triazol-3-one (interm. 7; $[\alpha]_{20}^{D}$=+93.07° @ 24.98 mg/5 ml in DMF).

A second fraction was boiled in $CH_3CN$. The mixture was stirred and then cooled. The precipitate was filtered off and dried, yielding 97 g (35%) of [S(R*,S*)(S*)]-2,4-dihydro-4-[4-[4-(4-hydroxyphenyl)-1-piperazinyl]phenyl]-2-[2-[(1-phenylethyl)amino]-1-methylpropyl]-3H-1,2,4-triazol-3-one (interm. 7a).

b) A mixture of intermediate (7) (0.00976 mol) in methanol (200 ml) and acetic acid (50 ml) was hydrogenated at 50° C. with Pd/C 10% (2 g) as a catalyst in the presence of $(CH_2O)n$ (2 g) and thiophene 4% in methanol (1 ml). After uptake of $H_2$, the catalyst was filtered off and the filtrate was evaporated. The residue was dissolved in $CH_2Cl_2$.

The organic solution was washed with a $NaHCO_3$ solution, dried, filtered and the solvent was evaporated. The residue was purified by column chromatography over silica gel (eluent: $CH_2Cl_2/CH_3OH$ 98/2). The pure fractions were collected and the solvent was evaporated. The residue was triturated in 2-propanol, filtered off and dried, yielding 3.8 g (74%) of [R(R*,R*)(R*)]-2,4-dihydro-4-[4-[4-(4-hydroxyphenyl)-1-piperazinyl]phenyl]-2-[2-[methyl(1-phenylethyl)amino]-1-methylpropyl]-3H-1,2,4-triazol-3one (interm. 8; $[\alpha]_{20}^{D}$=+17.69° @ 24.31 mg/5 ml in DMF).

EXAMPLE A4 a) A mixture of 2,4-dihydro-4-[4-[4-(4-methoxyphenyl)-1-piperazinyl]phenyl]-3H-1,2,4-triazol-3-one (0.05 mol), ethyl 2-bromobutanoate (0.055 mol) and $Na_2CO_3$ (0.15 mol) in 1-methyl-2-pyrrolidinone (250 ml) was stirred at 75° C. overnight. Ethyl 2-bromobutanoate (0.015 mol) was added again. The mixture was stirred at 75° C. for 6 hours, at room temperature for 48 hours, poured out into $H_2O$ and stirred for 30 minutes. The precipitate was filtered off and dissolved in $CH_2Cl_2$. The solution was filtered. The filtrate was dried, filtered and the solvent was evaporated. The residue was triturated in DIPE and ethyl acetate, filtered off and dried, yielding 10 g (43%) of (±)-ethyl α-ethyl-4,5-dihydro-4-[4-[4-(4-methoxyphenyl)-1-piperazinyl]phenyl]-5-oxo-1H-1,2,4-triazol-1-acetate (interm. 9).

b) A mixture of $NaHSO_3$ (1 g) in HBr 48% (250 ml) and $CH_3COOH$/HBr (250 ml) was stirred for 15 minutes. Intermediate (9) (0.022 mol) was added. The mixture was stirred and refluxed for 90 minutes. The solvent was evaporated. Toluene was added and the solvent was evaporated. The residue was dissolved in $CH_3OH$. The mixture was stirred on an ice bath. $SOCl_2$ (24 g) was added dropwise and the mixture was stirred overnight. The solvent was evaporated and the residue was dissolved in $CH_2Cl_2$. The organic solution was washed with a $NaHCO_3$ solution, dried, filtered and the solvent was evaporated. The residue was triturated in DIPE, filtered off and dried, yielding 6.6 g of (±)-methyl α-ethyl-4,5-dihydro-4-[4-[4-(4-hydroxyphenyl)-1-piperazinyl]phenyl]-5-oxo-1H-1,2,4-triazol-1-acetate (interm. 10).

c) A mixture of (−)-(2S-cis)-2-(2,4-difluorophenyl)-2-(1H-1,2,4-triazol-1-ylmethyl)-1,3-dioxolane-4-methanol methanesulfonate(ester) (0.007 mol), intermediate (10) (0.0068 mol) and NaOH (0.008 mol) in DMF (100 ml) was stirred at 50° C. under $N_2$ flow overnight, then poured out into $H_2O$ and stirred for 1 hour. The precipitate was filtered off and dissolved in $CH_2Cl_2$. The organic layer was separated, dried, filtered and the solvent was evaporated. The residue was purified by column chromatography over silica gel (eluent: $CH_2Cl_2/CH_3OH$/hexane/ethyl acetate 48/2/20/30). The pure fractions were collected and the solvent was evaporated. The residue was triturated in ethyl acetate, filtered off and dried, yielding 1.4 g (29%) of methyl (2S-cis)-4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-α-ethyl4,5-dihydro-5-oxo-1H-1,2,4-triazol-1-acetate (interm. 11).

d) A mixture of intermediate (11) (0.009 mol) and $NaBH_4$ (0.045 mol) in dioxane (300 ml) and $H_2O$ (100 ml) was stirred at room temperature overnight. A saturated $NH_4Cl$ solution (100 ml) was added. The mixture was stirred for 3 hours. HCl (10 ml) was added. The mixture was stirred for 48 hours, then neutralized with a $Na_2CO_3$ solution and extracted with $CH_2Cl_2$. The organic layer was separated, washed, dried, filtered and the solvent was evaporated. The residue was purified by column chromatography over silica gel (eluent: $CH_2Cl_2/CH_3OH$ 96/4). The pure fractions were collected and the solvent was evaporated. The residue was triturated in DIPE, filtered off and dried, yielding 4.2 g (68%) (2S-cis)-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[1-(hydroxymethyl)propyl]-3H-1,2,4-triazol-3-one (interm. 12).

e) A mixture of intermediate (12)(0.01 mol) and methanesulfonyl chloride (0.0131 mol) in $CH_2Cl_2$ (100 ml) was stirred. NN-bis(1-methylethyl)ethanamine (3 ml) was added and the mixture was stirred overnight and then poured out into $H_2O$. The organic layer was separated, washed, dried, filtered and the solvent was evaporated. The residue was dissolved in ethyl acetate. The mixture was filtered over dicalite and the filtrate was evaporated. The residue was purified by column chromatography over silica gel (eluent: $CH_2Cl_2/CH_3OH$ 98/2). The pure fractions were collected and the solvent was evaporated, yielding 8.2 g (2S-cis)-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-2,4-dihydro-2-[1-[[(methylsulfonyl)oxy]methyl]propyl]-3H-1,2,4-triazol-3-one (interm. 13).

EXAMPLE A5 a) A mixture of (±)-2,4-dihydro-4-[4-[4-(4-hydroxyphenyl)-1-piperazinyl]phenyl]-2-(1-methyl-2-oxopropyl)-3H-1,2,4-triazol-3-one (0.120 mol) in DMF (700 ml) was cooled on ice. Potassium tri-sec-butylborohydride, 1M solution in THF (300 ml) was added dropwise. The mixture was allowed to warm to room temperature, then poured out into an aqueous $NH_4Cl$ solution. The precipitate was filtered off, dried and crystallized from 2-propanol. This fraction was separated into its enantiomers over CHIRALPAC AD [(amylose 3,5 dimethylphenyl carbamate) purchased from Daicel Chemical Industries, Ltd, in Japan] (eluent: 100% ethanol). Two pure fraction groups were collected and their solvent was evaporated. The desired fraction was recrystallized from methanol. The precipitate was filtered off and dried, yielding 0.9 g of [R-(R*,R*)]-2,4-dihydro-2-(2-hydroxy-1methylpropyl)-4-[4-[4-(4-hydroxyphenyl)-1-piperazinyl]phenyl]-3H-1,2,4-triazol-3-one (interm. 14a; $[\alpha]_{20}^D$=+10.35° @ 48.61 mg/5 ml in DMF) and 0.8 g [S-(R*,R*)]-2,4-dihydro-2-(2-hydroxy-1-methylpropyl)-4-[4-[4-(4-hydroxyphenyl)-1-piperazinyl] phenyl]-3H-1,2,4-triazol-3-one (interm. 14b).

b) Reaction under $N_2$ flow. A mixture of (−)-(2S,cis)-2-(2,4-difluorophenyl)-2-(1H -1,2,4-triazol-1-ylmethyl)-1,3-dioxolane-4-methanol 4-methylbenzenesulfonate(ester) (0.012 mol), intermediate (14a) (0.0109 mol) and NaOH (0.011 mol) in DMF (150 ml) was stirred overnight at 70° C. The reaction mixture was cooled and poured out into water. The precipitate was filtered off and dried. This fraction was purified by HPLC over Silica Motrex Amicon (20–45 μm; eluent: $Cl_3CCH_3/C_2H_5OH$ 90/10). The pure fractions were collected and the solvent was evaporated. The residue was triturated in methanol, filtered off and dried, yielding 5.3 g of [2S-[2α,4α(S*,S*)]]-4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]phenyl]-2,4-dihydro-2-(2-hydroxy-1-methylpropyl)-3H-1,2,4-triazol-3-one (interm. 15; $[\alpha]_{20}^D$=−7.71° @ 48.61 mg/5 ml in DMF).

c) A mixture of intermediate (15) (0.0465 mol) in $CH_2Cl_2$ (250 ml) and pyridine (200 ml) was stirred on ice. Methanesulfonyl chloride (0.065 mol) was added. The mixture was allowed to warm to room temperature and then stirred overnight. Methanesulfonyl chloride (0.026 mol) was added again. The mixture was stirred overnight. The solvent was evaporated and the residue was dissolved in $CH_2Cl_2$. The organic solution was washed, dried, filtered and the solvent was evaporated. The residue was triturated in DIPE, filtered off and dried, yielding 34 g (95.5%) of [2S-[2α,4α(S*,S*)]]-4-[4-[4-[4-[[2-(2,4 difluorophenyl)-2-(1H-1,2,4-triazol-1-ylmethyl) -1,3-dioxolan-4-yl]methoxy]phenyl]-1-piperazinyl]phenyl]-2,4-dihydro-2-[1-methyl-2-[(methylsulfonyl)oxy]propyl]-3H-1,2,4-triazol-3-one (interm. 16; mp. 172.0° C.; $[\alpha]_{20}^D$=−6.96° @ 23.69 mg/5 ml in DMF).

EXAMPLE A6 a) A mixture of (±)-2,4-dihydro-4-[4-[4-(4-methoxyphenyl)-1-piperazinyl]phenyl]-2-(1-methyl-2-oxopropyl)-3H-1,2,4-triazol-3-one (0.05 mol) and 1-(phenylmethyl)4-piperidinamine (0.13 mol) in THF (350 ml) was stirred at 140° C. in an autoclave for 16 hours under pressure of $H_2$ (50 atm) and $CO_2$ (10 atm) with Pd/C 10% (3 g) as a catalyst in the presence of thiophene solution 4% (3 ml) and $CaH_2$ (0.125 mol). The mixture was cooled. The catalyst was filtered off and the filtrate was evaporated. The residue was triturated in 2-propanol, filtered off and dried. The residue was boiled in $CH_3CN$ (400 ml). The mixture was cooled for 15 minutes. The precipitate was filtered off and dried. The residue was crystallized from $CH_3CN$/dioxane 50/50. The precipitate was filtered off and dried, yielding 14.8 g (50%) of (±)-(R*S*)-2,4-dihydro-4-[4-[4-(4-methoxyphenyl)-1-piperazinyl]phenyl]-2-[2-[[1-(phenylmethyl)-4-piperazinyl]amino]-1-methylpropyl]-3H-1,2,4-triazol-3-one (interm. 17a).

The combined filtrates were evaporated. The residue was triturated in DIPE, filtered off and dried. This fraction was purified by HPLC (eluent: $CH_2Cl_2/CH_3OH$ 100/0 to 95/5; column: AMICON 20 μm). The desired fractions were collected and the solvent was evaporated. The residue was boiled in 2-propanol. After cooling, the precipitate was filtered off and dried, yielding 7.2 g (24%) of (±)-(R*R*)-2,4-dihydro-4-[4-[4-(4-methoxyphenyl)-1-piperazinyl]phenyl]-2-[2-[[1-(phenylmethyl)4-piperazinyl]amino]-1-methylpropyl]-3H-1,2,4-triazol-3-one (interm. 17).

b) A mixture of intermediate (17) (0.0119 mol) and $Na_2SO_3$ (1 g) in HBr 48% (100 ml) was stirred and refluxed for 5 hours. The solvent was evaporated and the residue was neutralized with a $NaHCO_3$ solution. The mixture was extracted with $CH_2Cl_2/CH_3OH$. The organic layer was separated, dried, filtered and the solvent was evaporated. The residue was triturated in 2-propanol, filtered off and dried, yielding 6.1 g (88%) of (±)-(R*,R*)-2,4-dihydro-4-[4-[4-(4-hydroxyphenyl)-1-piperazinyl]phenyl]-2-[2-[[1-(phenylmethyl)4-piperazinyl]amino]-1-methylpropyl]-3H-1,2,4-triazol-3-one (interm. 18).

EXAMPLE A7 a) Reaction under $N_2$ atmosphere. $Na_2CO_3$ (0.01 mol) was added to a mixture of 2-(2-bromoethyl)-2,4-dihydro-4-[4-[4-(4-hydroxyphenyl)-1-piperazinyl]phenyl]-3H -1,2,4-triazol-3-one (0.0054 mol) in 1-methyl-2-pyrrolidinone (25 ml). This mixture was stirred at 60° C. A solution of (+)-(R)-α-methylbenzenemethanamine (0.0065 mol) in 1-methyl-2-pyrrolidinone (25 ml) was added dropwise and the resulting reaction mixture was stirred overnight at 60° C. The reaction mixture was cooled, poured out into ice-water and the resulting precipitate was filtered off, washed with water, then dried. This fraction was recrystallized from 2-propanol, filtered off and dried, yielding 1.98 g (77%)of (R)-2,4-dihydro4-[4-[4-(4-hydroxyphenyl)-1-piperazinyl] phenyl]-2-[2-[(1-phenylethyl)amino]ethyl]-3H-1,2,4-Triazol-3-one (interm. 19).

b) Reaction under $N_2$ atmosphere. NaH 60% (0.12 mol) was added to 2,4-dihydro-4-[4-[4-(4-methoxyphenyl)-1-piperazinyl]phenyl]-3H-1,2,4-triazol-3-one (0.1 mol) in DMF, and stirred for 30 minutes at 50° C. A solution of 1-chloro-2-propanone (0.1 mol) in DMF was added dropwise and the resulting reaction mixture was stirred overnight at 50° C. The reaction mixture was cooled, poured out into ice-water and the resulting precipitate was filtered off, washed with water, and dried. This fraction was recrystallized from $CH_2Cl_2/CH_3OH$. The precipitate was filtered off and the filtrate was evaporated. The residue was crystallized from methanol, filtered off and dried. The residue was combined with the crystallized compound, recrystallized from $CH_2Cl_2/CH_3OH$, filtered off and dried, yielding 0.65 g of 2,4dihydro-4-[4-[4-(4-methoxy-phenyl)-1-piperazinyl] phenyl]-2-(2-oxopropyl)-3H-1,2,4-triazol-3-one (interm. 20).

EXAMPLE A8

A mixture of phenyl cis-[4-[4-[4-[[2-(2,4-difluorophenyl)-2-(1H-1,2,4-triazol-1-ylmethyl)-1,3-dioxolan-4-yl)methoxy]phenyl]-1-piperazinyl]phenyl] carbamate (0.005 mol), prepared according to the procedure described in EP-A-0,228,125 and 1,1-dimethylethyl [1-methyl-2-(methylamino)propyl](phenylmethyl) carbamate (0.005 mol) in dioxane (50 ml) was stirred and refluxed overnight. The solvent was evaporated. The residue was purified by column chromatography over silica gel (eluent: $CH_2Cl_2/CH_3OH$/ethylacetate/hexane 48/2/30/20). The pure fractions were collected and the solvent was evaporated, yielding 2.7 g (62.3%) of 1,1-dimethylethyl (2S-cis)-[2-[[[[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]amino]carbonyl]methylamino]-1-methylpropyl](phenylmethyl)carbamate (interm. 133).

EXAMPLE A9

Reaction under $N_2$ atmosphere. A mixture of intermediate 110 (0.745 mol) in THF (3000 ml) was stirred for 1 hour at 40° C. The mixture was allowed to cool to 30° C. 2 M $LiBH_4$ in TBF (0.800 mol) was added dropwise at 30° C. After addition of 100 ml, the reaction mixture was gradually warmed to 60° C. while the rest of LiBH4 was added dropwise. Then, the reaction mixture was stirred and refluxed (65° C.) for ± 60 hours. The reaction mixture was cooled. 2-Propanone (500 ml) was added dropwise. Water (800 ml) was added over 1.5 hours. More water (2 L) was added. A solution of $NH_4Cl$ (350 g) in water (1.5 L) was added and the mixture was stirred for 2 hours. The layers were separated. The organic layer was dried, filtered and the solvent was evaporated.

The residue was stirred in DIPE (2 L), filtered off and dried. This fraction was purified by column chromatography over silica gel (eluent: $CH_2Cl_2/CH_3OH$ 95/5). The desired fractions were collected and the solvent was evaporated, yielding 120 g (32.6%) of [B(S)]-2,4-dihydro-2-[2-[[1-(hydroxymethyl)-2-methylpropyl]amino]-1-methylpropyl]-4-[4-[4-(4-hydroxyphenyl)-1-piperazinyl]phenyl]-3H-1,2,4-triazol-3-one (interm. 104).

EXAMPLE A10 a) A mixture of [S-(R*,S*)]-2,4-dihydro-2-(2-hydroxy-1-methylpropyl)4-[4-[4-(4-methoxyphenyl)-1-piperazinyl]phenyl]-3H-1,2,4-triazol-3-one (0.01 mol), p-toluenesulfonyl chloride (0.012 mol), triethylamine (2 g) and dimethylaminopyridine (0.5 g) in $CH_2Cl_2$ (100 ml) was stirred at room temperature for 4 days. The mixture was taken up in $CH_2Cl_2$ and purified by column chromatography over silica gel (eluent: $CH_2Cl_2$ 100%). The pure fractions were collected and the solvent was evaporated. The residue was triturated in methylisobutyl keton, filtered off and dried, yielding 4.6 g (79%) [S-(R*,S*)]-2,4-dihydro-4-[4-[4-(4-methoxyphenyl)-1-piperazinyl]phenyl]-2-[1-methyl-2-[[(4-methylphenyl)sulfonyl]oxy]propyl]-3H-1,2,4-triazol-3-one (interm. 134).

b) A mixture of intermediate 134 (0.0071 mol) and sodium azide (0.009 mol) in DMF (50 ml) was stirred at 80° C. for 1 hour, at 100° C. for 4 hours and cooled. $H_2O$ was added and the mixture was allowed to crystallize out. The precipitate was filtered off, washed with $H_2O$ and dissolved in $CH_2Cl_2$. The organic solution was dried, filtered and the solvent was evaporated, yielding 2.8 g (88%) of [S(R*,R*)]-2-(2-azido-1-methyl-propyl)-2,4-dihydro-4-[4-[4-(4-methoxyphenyl)-1-piperazinyl]phenyl]-3H-1,2,4-triazol-3-one (interm. 87).

c) A mixture of intermediate 87 (0.0062 mol) and triphenylphosphine (0.008 mol) in THF (100 ml) was stirred at 50° C./60° C. for 24 hours. Water (1 ml) was added. The mixture was stirred at 50° C./60° C. for 8 hours. The solvent was evaporated. The residue was stirred in $H_2O$ (100 ml) and a concentrated HCl solution (5 ml). The mixture was filtered. The filtrate was washed 3 times with $CH_2Cl_2$, neutralized with a $NaHCO_3$ solution and extracted with $CH_2Cl_2/CH_3OH$ 90/10. The organic layer was separated, dried, filtered and the solvent was evaporated. The residue was crystallized from ethanol. The precipitate was filtered off and dried, yielding 1.36 g (52%) of [S-(R*,R*)]-2-(2-aminomethylpropyl)-2,4-dihydro-4-[4-[4-(4-methoxyphenyl)-1-piperazinyl]phenyl]-3H-1,2,4-triazol-3-one (interm. 88).

d) A mixture of intermediate 105 (0.049 mol) in THF (300 ml) and water (200 ml) was hydrogenated at room temperature with palladium on activated carbon 10% (4 g) as a catalyst in the presence of a 4% thiophene solution (4 ml). After uptake of hydrogen, the catalyst was filtered off and the filtrate was evaporated. The residue was purified over silica gel on a glass filter (eluent 1: $CH_2Cl_2/CH_3OH$ 99/1 and eluent 2: $CH_2Cl_2/(CH_3OH/NH_3)$ 95/5). The pure fractions were collected and the solvent was evaporated, yielding 18.6 g (90%) [R-(R*,S*)]-2-(2-amino-1-methylpropyl)-2,4-dihydro-4-[4-[4-(4-methoxyphenyl)-1-piperazinyl] phenyl]-3H-1,2,4-triazol-3-one (interm. 106).

EXAMPLE A11 a) A mixture of 2,4-dihydro-4-[4-[4-(4-methoxyphenyl)-1-piperazinyl]phenyl]-3H-1,2,4-triazol-3-one (0.1 mol) and KOH powder (0.1 mol) in 1,3-dimethyl-2-imidazolidinone (250 ml) and methylbenzene (100 ml) was stirred at 140° C. under $N_2$ flow for 15 min and then cooled to 80° C. 1-[(4-methylphenyl)sulfonyl]-4-piperidinol methanesulfonate(ester) (0.12 mol) was added. The mixture was stirred at 140° C. for 24 hours and cooled. The precipitate was filtered off (*). The filtrate was poured out on ice and extracted three times with toluene. The combined organic layer was washed twice with $H_2O$, dried ($MgSO_4$), filtered and the solvent was evaporated. (*) The precipitate was refluxed in $CH_2Cl_2$ (1000 ml) and $CH_3OH$ (500 ml). The precipitate was filtered off warm, allowed to crystallize out, filtered off and dried in vacuo at 60° C. (yielding 8.6 g). Part (1 g) of this fraction was dried in vacuo at 60° C. for 28 hours. Yielding: 4-[4,5-dihydro-4-[4-[4-(4-methoxyphenyl)-1-piperazinyl]phenyl]-5-oxo-1H-1,2,4-triazol-1-yl]-1-[(4-methylphenyl)sulfonyl]piperidine (interm. 135).

b) Intermediate 135 (0.027 mol) was added to a mixture of $NaHSO_3$ (2 g) in HBr 48% (300 ml) and $HBr/CH_3OH$ (150 ml). The mixture was stirred and refluxed for 4 hours and cooled. The solvent was evaporated. The residue was dissolved in water (300 ml). $NH_3$ aq. 28% (50 ml) was added. The precipitate was filtered off and dried in vacuo at 75° C. (yielding 7.5 g, (66%). Part of this fraction (1 g) was recrystallized from diethyl ether. The precipitate was filtered off and dried. Yielding: 2,4-dihydro-4-[4-[4-(4-hydroxyphenyl)-1-piperazinyl]phenyl]-2-(4-piperidinyl)-3H-1,2,4-triazol-3-one (interm. 136).

EXAMPLE A12 a) A mixture of 1,4-dioxaspiro[4.5]decan-8-one (0.115 mol) and hydrazinecarboxal-dehyde (0.23 mol) in methanol (300 ml) was hydrogenated at 50° C. under 100 atm for 16 hours with Pd/C 10% (3 g) as a catalyst. After uptake of hydrogen (1 equiv), the catalyst was filtered off and the filtrate was evaporated. The residue was dissolved in $CH_2Cl_2$ (750 ml). The organic solution was washed with $H_2O$ (100 ml), dried ($MgSO_4$), filtered and the solvent was evaporated. Yielding: 19.9 g of 2-(},4-dioxaspiro[4.5]-decan-8-yl)hydrazinecarboxaldehyde (86%) (interm. 137).

b) A mixture of intermediate 137 (0.0995 mol), phenyl [4-[4-(4-methoxyphenyl)-1 -piperazinyl]phenyl]carbamate (0.09 mol) and N,N-dimethyl-4-pyridinamine (0.0995 mol) in methylbenzene (300 ml) was stirred at 80° C. for 16 hours using a Dean Stark apparatus, then stirred and refluxed for 3 hours and cooled. $H_2O$ (200 ml) was added and the mixture was extracted with $CH_2Cl_2$. The organic layer was separated, washed once with H₂O and once with a saturated NaCl solution, then dried (MgSO₄), filtered and the solvent was evaporated. The residue was crystallized from 2-propanol. The precipitate was filtered off and dried. Yielding: 32.3 g (73%). Part of this fraction (3 g) was recrystallized from 2-propanol. The precipitate was filtered off and dried. This fraction was purified by flash chromatography over silica gel (eluent: CH₂Cl₂/CH₃OH 98.5/1.5). The pure fractions were collected and the solvent was evaporated. The residue was crystallized from 2-propanol. The precipitate was filtered off and dried. Yielding: 2-(1,4-dioxaspiro[4.5]decan-8-yl)-2,4-dihydro-4-[4-[4-(4-methoxyphenyl)-1-piperazinyl]phenyl]-3H-1,2,4-triazol-3-one (interm. 138).

c) A mixture of intermediate 138 (0.059 mol) in H₂SO₄ 10% (500 ml) was stirred at 60° C. for 3 hours and cooled to room temperature. The precipitate was filtered off and suspended in H₂O (300 ml). The mixture was neutralized with a saturated K₂CO₃ solution. The precipitate was filtered off, washed twice with H₂O and dried. This fraction was triturated in ethano/CH₂Cl₂ 1:1, filtered off and dried. This fraction was purified by flash column chromatography over silica gel (eluent: CH₂Cl₂/CH₃OH 97/3). The pure fractions were collected and the solvent was evaporated. The residue was dried in vacuo. Yielding: 2,4dihydro-4-[4-[4-(4-methoxyphenyl)-1-piperazinyl]-phenyl]-2-(4-oxocyclohexyl)-3H-1,2,4-triazol-3-one (interm. 139).

d) A mixture of intermediate 139 (0.031 mol) and benzenemethanamine (0.018 mol) in methanol (150 ml) and THF (150 ml) was hydrogenated at 50° C. with Pd/C 10% (2 g) as a catalyst in the presence of thiophene solution 4% in DIPE (2 ml). After uptake of H₂ (1 equiv), the catalyst was filtered off and the filtrate was evaporated. The residue was purified by flash column chromatography over silica gel (eluent: CH₂Cl₂/CH₃OH 100/0 to 98/2). Two pure fractions were collected and their solvents were evaporated. The residue was dried in vacuo at 60° C. Yielding: 3.4 g of (±)-cis-2,4-dihydro-4-[4-[4-(4-methoxyphenyl)-1-piperazinyl]phenyl]-2-[4-[(phenylmethyl)amino]cyclohexyl]-3H-1,2,4-triazol-3-one (interm. 140) and 1.4 g of (±)-trans-2,4-dihydro-4-[4-[4-(4-methoxyphenyl)-1-piperazinyl]phenyl]-2-[4-[(phenylmethyl)amino]cyclohexyl]-3H-1,2,4-triazol-3-one (interm. 144).

EXAMPLE A13

A mixture of intermediate 76 (0.0228 mol) in THF (200 ml) was hydrogenated at 125° C. for 64 hours with Pt/C 5% (2 g) as a catalyst. After uptake of H₂ (1 equiv), the catalyst was filtered off and the filtrate was evaporated. Yielding: 10 g of (R)-1-[4-[4(4 -methoxyphenyl)-1-piperazinyl]phenyl]-3-[2-[(1-phenylethyl)amino]-1,2-dimethylethyl]-2-imidazolidinone (interm. 141).

Table 1b lists intermediates which were made analogous to one of the above examples.

TABLE 1b

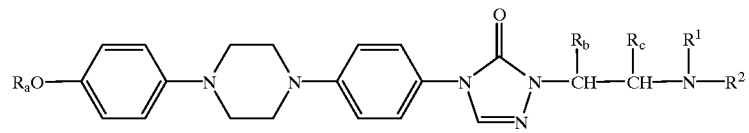

| Int. No. | Ex. No. | —NR¹R² | $R_a$ | $R_b$ | $R_c$ | stereochemistry if not racemic; optical rotation as $[\alpha]_{20}^D$ @ concentration (in mg/5 ml DMF); salts and melting point (in ° C.) |
|---|---|---|---|---|---|---|
| 85 | A2c | —NH₂ | H | CH₃ | CH₃ | [R(R*,S*)]; +1.01° @ 19.79 mg/2 ml; mp. 237.2 |
| 86 | A2c | —NH₂ | H | CH₃ | CH₃ | [S(R*,R*)]; +7.35° @ 19.86 mg/2 ml; mp. 250.8 |
| 87 | A10b | —N=N⁺—N⁻ | CH₃ | CH₃ | CH₃ | [S(R*,R*)] |
| 88 | A10c | —NH₂ | CH₃ | CH₃ | CH₃ | [S(R*,S*)]; +6.12° @ 11.77 mg/2 ml; mp. 206.4 |
| 89 | A2d | —NH—CO—O—C(CH₃)₃ | H | CH₃ | CH₃ | [S(R*,R*)]; −26.78° @ 20.24; mp. 207.2 |
| 90 | A2c | —NH₂ | H | CH₃ | CH₃ | [R(R*,R*)]; −7.38° @ 20.33; mp. 250.2 |
| 91 | A2d | —NH—CO—O—C(CH₃)₃ | H | CH₃ | CH₃ | [R(R*,R*)]; +28.62° @ 25.68; mp. 211.6 |
| 92 | A2c | —NH₂ | H | CH₃ | CH₃ | [S(R*,S*)]; −0.99° @ 20.24; mp. 240.9 |
| 93 | A2d | —NH—CO—O—C(CH₃)₃ | H | CH₃ | CH₃ | [S(R*,S*)]; −20.84° @ 26.15; mp. 184 |
| 94 | A3a | —NH—CH(CH₃)-phenyl | H | CH₃ | CH₃ | [R(R*,S*)(S*)]; +9.71° @ 25.22 |
| 95 | A3a | —NH—CH(CH₃)-phenyl | H | CH₃ | CH₃ | [S(R*,R*)(R*)]; −93.99° @ 24.79 |
| 96 | A1c | —NH—CH(CH₃)-phenyl | H | CH₃ | CH₃ | [R(R*,S*)(S*)] |
| 97 | A3b | —N(CH₃)—CH(CH₃)-phenyl | H | CH₃ | CH₃ | [R(R*,S*)(S*)]; +15.53° @ 25.11 |
| 98 | A3b | —N(CH₃)—CH(CH₃)-phenyl | H | CH₃ | CH₃ | [S(R*,S*)(S*)]; −15.27° @ 25.54; mp. 227.0 |
| 99 | A3b | —N(CH₃)—CH(CH₃)-phenyl | H | CH₃ | CH₃ | [S(R*,R*)(R*)]; −17.72° @ 24.27; mp. 201.6 |

TABLE 1b-continued

| Int. No. | Ex. No. | —NR¹R² | $R_a$ | $R_b$ | $R_c$ | stereochemistry if not racemic; optical rotation as $[\alpha]_{20}^D$ @ concentration (in mg/5 ml DMF); salts and melting point (in ° C.) |
|---|---|---|---|---|---|---|
| 100 | A6b | —HN—(1-benzyl-piperidin-4-yl) | H | $CH_3$ | $CH_3$ | — |
| 101 | A6b | —NH—CH($CH_3$)-phenyl | H | H | $CH_3$ | [2B(R)] |
| 102 | A3b | —N($CH_3$)—($CH_2$)$_2$—O-phenyl | H | $CH_3$ | $CH_3$ | — |
| 103 | A6b | —HN—(1-benzyl-piperidin-4-yl) | H | $CH_3$ | $CH_3$ | (R*,R*) |
| 104 | A9 | —NH—CH[CH($CH_3$)$_2$]—$CH_2$OH | H | $CH_3$ | $CH_3$ | — |
| 105 | A10b | —N=N$^+$=N$^-$ | $CH_3$ | $CH_3$ | $CH_3$ | [R(S*,R*)]; +40.44 @ 25.72; mp. 178 |
| 106 | A10d | —$NH_2$ | $CH_3$ | $CH_3$ | $CH_3$ | [R(R*,S*)]; 0.00° @ 24.70; mp. 192 |
| 107 | A1e | —NH—$CH_2$-phenyl | H | $CH_3$ | $CH_3$ | [R-(R*,S*)]; +45.57° @ 23.48; mp. 194 |
| 108 | A1c | —NH—CH($CH_3$)-1-naphthyl | H | $CH_3$ | $CH_3$ | [R(R*,S*)(S*)]; −61.61° @ 23.94; mp. 174 |
| 109 | A6b | —NH—(2,3-dihydro-1-indenyl) | H | $CH_3$ | $CH_3$ | — |
| 110 | A1c | —NH—CH[CH($CH_3$)$_2$]—CO—O$C_2H_5$ | H | $CH_3$ | $CH_3$ | [A(S)]; −43.89° @ 25.29; mp. 182 |
| 112 | A1c | —NH-[3,4-dihydro-2H-1-benzo-pyran-4-yl] | H | $CH_3$ | $CH_3$ | — |
| 114 | A6b | —HN—(2-hydroxy-indan-1-yl) | H | $CH_3$ | $CH_3$ | [A[1S-(1R*,2S*)]] |
| 115 | A6b | —HN—(2-hydroxy-indan-1-yl) | H | $CH_3$ | $CH_3$ | [B[1S-(1R*,2S*)]] |
| 116 | A7a | —NH—$CH_2$-phenyl | $CH_3$ | $CH_3$ | H | — |
| 117 | A6b | —NH—$CH_2$-phenyl | H | $CH_3$ | H | — |
| 118 | A1c | —NH—CH($CH_3$)-1-naphthyl | H | $CH_3$ | $CH_3$ | [S(R*,R*)(R*)]; −86.75° @ 24.15; mp. 200 |
| 119 | A1d | —NH—$CH_2$-phenyl | H | $CH_3$ | $CH_3$ | [R(R*,R*)]; +44.14° @ 26.60; mp. 200 |
| 120 | A1e | —NH—$CH_2$-(2-thienyl) | H | $CH_3$ | $CH_3$ | [R(R*,S*)] |
| 121 | A1e | —NH—$CH_2$-(3-thienyl) | H | $CH_3$ | $CH_3$ | [R(R*,S*)] |
| 122 | A1d | —NH—$CH_2$-phenyl | H | $CH_3$ | $CH_3$ | [S(R*,R*)]; −45.82° @ 23.90; mp. 199 |
| 123 | A1d | —NH—$CH_2$-(3-pyridinyl) | H | $CH_3$ | $CH_3$ | [R(R*,S*)]; +44.85° @ 22.74; mp. 200 |
| 124 | A1d | —NH—$CH_2$-(2-pyridinyl) | H | $CH_3$ | $CH_3$ | [R(R*,S*)] |
| 125 | A1d | —NH—$CH_2$-phenyl | H | $CH_3$ | $CH_3$ | [S(R*,S*)]; −44.69° @ 25.40; mp. 195 |
| 126 | A1c | —NH-[3,4-dihydro-2H-1-benzo-pyran-4-yl] | H | $CH_3$ | $CH_3$ | (A) |
| 127 | A1e | —NH—$CH_2$-(4-pyridinyl) | H | $CH_3$ | $CH_3$ | [R(R*,S*)] |
| 129 | A1c | —NH—CH($CH_3$)-phenyl | H | $C_2H_5$ | $CH_3$ | (S) |
| 130 | A1e | —NH—$CH_2$-(1H-imidazol-2-yl) | H | $CH_3$ | $CH_3$ | [R(R*,S*)] |

TABLE 1b-continued

[Structure: R_a-O-phenyl-N-piperazine-N-phenyl-N-triazolone-N-CH(R_b)-CH(R_c)-N(R^1)-R^2]

| Int. No. | Ex. No. | —NR¹R² | R_a | R_b | R_c | stereochemistry if not racemic; optical rotation as $[\alpha]_{20}^D$ @ concentration (in mg/5 ml DMF); salts and melting point (in °C.) |
|---|---|---|---|---|---|---|
| 131 | A6b | —HN-(2-hydroxyindanyl) | H | CH₃ | CH₃ | [B[1R-(1R*,2S*)]] |

TABLE 1c

[Structure: R_a-O-phenyl-N-piperazine-N-phenyl-N-(R⁶=R⁷ triazolone ring)-N-L with C=O]

| Int. No. | Ex. No. | —R⁶—R⁷— | R_a | L | stereochemistry if not racemic |
|---|---|---|---|---|---|
| 68 | A1a | —N=CH— | H | —CH(CH₃)—CH(CH₃)—N(H)—CH₂—phenyl | (R*,R*) |
| 69 | A1a | —N=CH— | H | —CH(CH₃)—CH(CH₃)—N(H)—CH₂—phenyl | (R*,S*) |
| 76 | A1a | —CH=CH— | CH₃ | —CH(CH₃)—CH(CH₃)—N(H)—CH(CH₃)—phenyl | (R) |
| 128 | A1c | —CH=CH— | H | —CH(CH₃)—CH(CH₃)—N(H)—CH(CH₃)—phenyl | (S) |
| 132 | A7a | —CH=CH— | CH₃ | —CH(CH₃)—CH₂—N(H)—CH₂—phenyl | — |
| 136 | A11 | —CH=N— | H | 4-piperidinyl (NH) | |
| 140 | A12 | —CH=N— | CH₃ | 4-(benzylamino)cyclohexyl | cis |

TABLE 1c-continued

| Int. No. | Ex. No. | —R⁶—R⁷— | Rₐ | L | stereochemistry if not racemic |
|---|---|---|---|---|---|
| 141 | A13 | —CH₂—CH₂— | CH₃ | —CH(CH₃)—CH(CH₃)—N(H)—CH(CH₃)—CH₂—phenyl | (R) |
| 142 | A6b | —CH₂—CH₂— | H | —CH(CH₃)—CH(CH₃)—N(H)—CH(CH₃)—CH₂—phenyl | [A(R)] |
| 143 | A6b | —CH₂—CH₂— | H | —CH(CH₃)—CH(CH₃)—N(H)—CH(CH₃)—CH₂—phenyl | [B(R)] |
| 144 | A12 | —CH=N— | CH₃ | cyclohexyl-NH-CH₂-phenyl | trans |
| 145 | A6b | —CH=N— | H | cyclohexyl-NH-CH₂-phenyl | cis |
| 146 | A6b | —CH=N— | H | cyclohexyl-NH-CH₂-phenyl | trans |
| 147 | A12 | —CH=N— | CH₃ | cyclohexyl-NH-CH(CH₃)-phenyl | [4(S)-cis] |
| 148 | A12 | —CH=N— | CH₃ | cyclohexyl-NH-CH(CH₃)-phenyl | [4(S)-trans] |
| 149 | A12 | —CH=N— | H | cyclohexyl-NH-CH(CH₃)-phenyl | [4(S)-cis]; H₂O (1:1) NaCl (1:1) |
| 150 | A12 | —CH=N— | H | cyclohexyl-NH-CH(CH₃)-phenyl | [4(S)-trans] |

TABLE 1c-continued

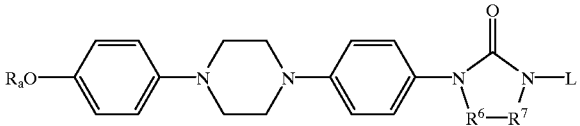

| Int. No. | Ex. No. | —R⁶—R⁷— | Rₐ | L | stereochemistry if not racemic |
|---|---|---|---|---|---|
| 151 | | —CH=CH— | H | 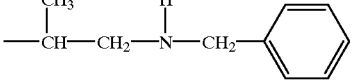 | |

B. PREPARATION OF THE FINAL COMPOUNDS

EXAMPLE B1 a) A mixture of (−)-(2S-cis)-2-(2,4-difluorophenyl)-2-(1H-1,2,4-triazol-1-ylmethyl)-1,3-dioxolane-4-methanol methanesulfonate(ester) (0.0071 mol), 1,1-dimethylethyl ]R(R*,S*)]-[2-[4-[4-[4-(4-hydroxyphenyl)-1-piperazinyl] phenyl]-4,5-dihydro-5-oxo-1H1,2,4-triazol-1-yl]-1-methylpropyl]carbamate (0.0059 mol) and NaOH pellets (0.012 mol) in DMF (100 ml) was stirred at 70° C. under N₂ flow for 2 hours and then cooled. DIPE (100 ml) and H₂O (400 ml) were added. The mixture was stirred and then allowed to crystallize out. The precipitate was filtered off, washed with H₂O and DIPE and purified over silica gel on a glass filter (eluent: CH₂Cl₂/CH₃OH 98/2). The pure fractions were collected and the solvent was evaporated. The residue was triturated in DIPE, filtered off and dried, yielding 3.24 g (69%) of 1,1-dimethylethyl [2S-[2α,4α(S*,R*)]]-[2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl]carbamate (compound 28; mp. 158.3° C.).

b) A mixture of compound (28)(0.0038 mol) in CF₃COOH (10 ml) and CH₂Cl₂ (50 ml) was stirred at room temperature for 4 hours and neutralized with a NaHCO₃ solution. The organic layer was separated, dried, filtered and the solvent was evaporated. The residue was triturated in 2-propanol, filtered off and dried, yielding 2.4 g (92%) of [2S-[2α,4α(S*,R*)]]-2-(2-amino-1-methylpropyl)-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-2,4-dihydro-3H-1,2,4-triazol-3-one (compound 37; mp. 168.5° C.).

EXAMPLE B2

A mixture of compound (37)(0.0034 mol), N-[(1,1-dimethylethoxy)carbonyl] phenylalanine, (0.005 mol) and N'-(ethylcarbonimidoyl)-N,N-dimethyl 1,3-propanediamine, (0.005 mol) in CH₂Cl₂ (100 ml) was stirred at room temperature for 2 hours. The mixture was washed twice with H₂O dried, filtered and the solvent was evaporated. The residue was triturated in 2-propanol, filtered off and dried, yielding 2.78 g (87%) of 1,1-dimethylethyl [2S-[2α,4α[(S*R*)(R*)]]]-[2-[[2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl] amino]-2-oxo-1-(phenylmethyl)ethyl]carbamate (compound 124; mp. 181.7° C.).

EXAMPLE B3

Chloro acetylchloride (0.005 mol) was added to a stirring mixture of [2S-[2α,4α(R*,R*)]]-2-(2-amino-1-methylpropyl)-4-[4-[4-[4-[[2-(2,4-difluorophephenyl)-2-(1H-1,2,4-triazol-1-ylmethyl)-1,3-dioxolan-4yl]methoxy] phenyl]-1-piperazinyl]-phenyl]-2,4-dihydro-3H-1,2,4-triazol-3-one (0.00436 mol) in CH₂Cl₂ (100 ml). A mixture of NaHCO₃ (1 g) in water (50 ml) was added. The mixture was stirred at room temperature for 4 hours. The organic layer was separated, dried, filtered and the solvent was evaporated. The residue was crystallized from 2-propanol. The precipitate was filtered off and dried, yielding 2.8 g (84%) of [2S-[2α,4α(R*,R*)]]-2-chloro-N-[2-[4-[4-[4-[[2-(2,4difluorophenyl)-2-(1H-1,2,4-triazol-1-ylmethyl)-1,3-dioxolan-4-yl]-methoxy]phenyl]-1-piperazinyl]phenyl]-4,5-dihydro-5-oxo-1H-1,2,4-triazol-1-yl]-1-methylpropyl] acetamide (compound 33; mp. 126.8° C.).

EXAMPLE B4 a) A mixture of compound (37) (0.0043 mol) and (S)-phenyl oxirane (0.005 mol) in 2-propanol (50 ml) was stirred and refluxed overnight. (S)-phenyl oxirane (0.005 mol) was added again. The mixture was stirred and refluxed for 3 hours. The solvent was evaporated. The residue was purified by column chromatography over silica gel (eluent: CH₂Cl₂/CH₃OH 99/1). The pure fractions were collected and the solvent was evaporated. The residue was triturated in DIPE, filtered off and dried, yielding 1.6 g (47%) of [2S-[2α,4α [(S*,R*)(R*)]]]4-[4-[4-[4-[[2-(2,4-difluorophenyl)-2-(1H-1,2,4-triazol-1-ylmethyl)-1,3-dioxolan-4-yl]methoxy] phenyl]-1-piperazinyl]phenyl]-2,4-dihydro-2-[2[(2-hydroxy-2-phenylethyl)amino]-1-methylpropyl]-3H-1,2,4-triazol-3-one (compound 81).

b) A mixture of (R)-phenyl oxirane (0.016 mol) in ethanol (50 ml) was stirred. Diethylamine was bubbled through the mixture for 2 hours. The solvent was evaporated. The residue was dissolved in a mixture of triethylamine (0.08 mol) in diethyl ether (30 ml). The mixture was stirred on ice. Methanesulfonyl chloride (0.015 mol) was added dropwise. The mixture was stirred at room temperature for 30 min. Compound 37 (0.0027 mol) was dissolved in DMF (20 ml) and H₂O (4 ml) and then added to the reaction mixture. The mixture was stirred overnight, poured out into H₂O and extracted with CH₂Cl₂. The organic layer was separated, dried, filtered and the solvent was evaporated. The residue was purified by column chromatography over silica gel (eluent: $CH_2Cl_2/(CH_3OH/NH_3)$ 98/2). The pure fractions were collected and the solvent was evaporated. The residue was triturated in DIPE and ethylacetate, filtered off and dried, yielding 1.1 g (45.8%) of [2S-[2alpha,4alpha[(S*,R*)(S*)]]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4-[2-[[2-(dimethylamino)-1-phenylethyl]amino]-1-methylpropyl]-2,4-dihydro-3H-1,2,4-triazol-3-one (compound 172).

EXAMPLE B5 a) A mixture of [2S-[2α,4α(S*,S*)]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[1-methyl-2-[(methylsulfonyl)oxy]propyl]-3H-1,2,4-triazol-3-one (0.0039 mol) and $NaN_3$ (0.005 mol) in DMF (50 ml) was stirred at 85° C. for 48 hours, poured out into $H_2O$ and stirred for 30 minutes. The precipitate was filtered off and dissolved in $CH_2Cl_2$. The organic solution was washed, dried, filtered and the solvent was evaporated. The residue was purified by column chromatography over silica gel (eluent: $CH_2Cl_2/CH_3OH$ 98/2). The pure fractions were collected and the solvent was evaporated. The residue was triturated in DIPE and 2-propanol, filtered off and dried, yielding 1.1 g (41%) of [2S-[2α,4α(R*,S*)]]-2-(2-azido-1-methylpropyl)-4-[4-[4-[4-[[2-(2,4difluorophenyl)-2-(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one; (compound 19).

b) A mixture of (2S-cis)-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[2-[(methylsulfonyl)oxy]ethyl-3H-1,2,4-triazol-3-one (0.0093 mol), (−)-(S)-α-methyl-benzenemethanamine (0.015 mol) and $Na_2CO_3$ (0.02 mol) in 1-methyl-2-pyrrolidinone (50 ml) was stirred for 5 hours at 100° C. and then cooled. Water was added. 2-Propanol was added. The mixture was allowed to crystallize out. The precipitate was filtered off, washed with water and dried. The residue was purified over silica gel on a glass filter (eluent: $CH_2Cl_2/CH_3OH$ (1) 99/1, (2) 98/2). The pure fractions were collected and the solvent was evaporated. The residue was crystallized from 2-propanol. The precipitate was filtered off and dried, yielding 4.6 g (64%) of [2S-[2α,4α(R*)]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(1-phenylethyl)amino]ethyl]-3H-1,2,4-triazol-3-one (compound 115; mp. 110.2° C.).

c) A mixture of (2S-cis)-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[1-methyl-2-[(methylsulfonyl)oxy]ethyl]-3H-1,2,4-triazol-3-one (0.0016 mol) in (+)-(R)-α-methylbenzenemethanamine (20 ml) was stirred at 140° C. for 4 hours in an autoclave, then cooled and purified over silica gel on a glass filter (eluent: $CH_2Cl_2$ 100%). The pure fractions were collected and the solvent was evaporated. The residue was crystallized from DIPE and 2-propanol. The precipitate was filtered off and dried, yielding 0.52 g (42%) of [2S-[2α,4α[R*(S*)]]]+[2S-[2α, 4α]S*(S*)]]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(1-phenylethyl)amino]-1-methylethyl]-3H-1,2,4-triazol-3-one (compound 118; mp. 114.9° C.).

d) A mixture of (2S-cis)-4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[1-methyl-2-[(methylsulfonyl)oxy]ethyl]-3H-1,2,4-triazol-3-one (0.00093 mol) and (−)-(s)-methylbenzenemethanamine (0.0099 mol) in 1,3-dimethyl-2-imidazolidinone (20 ml) was stirred at 140° C. under $N_2$ flow for 6 hours, then cooled and poured out into ice water. The precipitate was filtered off and recrystallized from DIPE and 2-propanol. The precipitate was filtered off and dried, yielding 0.31 g (43%) of [2S-[2α,4α[R*(R*)]]]-[2S-[2α,4α[S*(R*)]]]-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[2-[(1-phenylethyl)amino]-1-methylethyl]-3H-1,2,4-triazol-3-one (compound 119).

EXAMPLE B6 a) A mixture of [2S-[2α,4α(R*,S*)]]+[2S-[2α,4α(S*,R*)]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[[1-(phenylmethyl)-4-piperidinyl]amino]-1-methylpropyl]-3H-1,2,4-triazol-3-one (0.0046 mol) in methanol (100 ml) was hydrogenated at room temperature for 72 hours with Pd on activated carbon 10% (2 g) as a catalyst. After uptake of $H_2$, the catalyst was filtered off and the filtrate was evaporated. The residue was purified over silica gel on a glass filter (eluent: $CH_2Cl_2/(CH_3OH/NH_3)$ 95/5 to 90/10). The pure fractions were collected and the solvent was evaporated. The residue was triturated in DIPE, filtered off and dried, yielding 3 g (84%) of [2S-[2α,4α(R*,S*)]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-(4-piperidinylamino)-1-methylpropyl]-3H-1,2,4-triazol-3-one diisopropylether(1:1) (compound 63).

b) A mixture of [2S-[2α,4α(R*,S*)]]+[2S-[2α,4α(S*,R*)]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[[1-(phenylmethyl)-4-piperidinyl]amino]-1-methylpropyl]-3H-1,2,4-triazol-3-one (0.006 mol) in THF (250 ml) was hydrogenated for 3 days with Pd on activated carbon 10% (2 g) as a catalyst. Then paraformaldehyde (0.006 mol) and thiophene solution 4% (2 ml) were added. Hydrogenation was continued at 50° C. After uptake of $H_2$, the mixture was cooled. The catalyst was filtered off and the filtrate was evaporated. The residue was purified by column chromatography over silica gel (eluent: $CH_2Cl_2/(CH_3OH/NH_3)$ 95/5). The pure fractions were collected and the solvent was evaporated. The residue was crystallized from 2-propanol. The precipitate was filtered off and dried, yielding 3.2 g (68%) of [2S-[2α,4α(R*,S*)]]+[2S-[2α,4α(S*,R*)]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(1-methyl-4-piperidinyl)amino]-1-methylpropyl]-3H-1,2,4-triazol-3-one (compound 64).

EXAMPLE B7

A mixture of 1,1-dimethylethyl [2S-[2α,4α[(R*,R*)(R*)]]]-[2-[[2-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl]amino]-2-oxo-1-(phenylmethyl)ethyl]carbamate (0.0058 mol) in HCl/2-propanol 6N (20 ml) and methanol (80 ml) was stirred at room temperature overnight. After evaporation, the residue was triturated in CH$_3$CN, filtered off and dried. The residue was taken up in toluene (200 ml). The mixture was stirred and refluxed for 8 hours using a water separator and then cooled. The precipitate was filtered off, washed with toluene, ground in a mortar and dried. This fraction was taken up in toluene (200 ml). The mixture was stirred and refluxed using a water separator. H$_2$O (20 ml) was added slowly dropwise. When all H$_2$O was removed, the mixture was cooled and stirred. The precipitate was filtered off, ground in a mortar and dried. This fraction was converted into the free base with a NaHCO$_3$ solution and CH$_2$Cl$_2$ and then purified over silica gel on a glass filter (eluent: CH$_2$Cl$_2$/CH$_3$OH 96/4). The pure fractions were collected and the solvent was evaporated. The residue was dried, dissolved in CH$_2$Cl$_2$ and converted into the hydrochloric acid salt (1:1) with HCl/2-propanol. The solvent was evaporated. The residue was recrystallized from 2-propanol. The precipitate was filtered off and dried. This fraction was dissolved in CH$_2$Cl$_2$ and converted into the hydrochloric acid salt (1:1) with HCl/2-propanol. The solvent was evaporated. The residue was boiled in 2-propanol. The mixture was cooled. The precipitate was filtered off and dried, yielding 2.44 g (48%) of [2S-[2α,4α[(R*,R*,)(R*)]]]-α-amino-N-[2-[4-[4-[4-[[2-(2,4-difluorophenyl)-2-(1H-1,2,4-triazol-1-ylmethyl)-1,3-dioxolan-4-yl]methoxy]phenyl]-1-pierazinyl]phenyl]-4,5-dihydro-5-oxo-1H-1,2,4-triazol-1-yl]-1-methylpropyl]benzenepropanamide monohydrochloride (compound 134).

EXAMPLE B8

A mixture of [2S-[2α,4α[A(R*)]]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(2-hydroxy-1-phenylethyl)amino]-1-methylpropyl]-3H-1,2,4-triazol-3-one (0.0052 mol) in THF (100 ml) was stirred. NaH 60% (0.01 mol) was added. The mixture was stirred for 15 minutes. Iodomethane (0.01 mol) was added. The mixture was stirred for 1 hour. NaH 60% (0.01 mol) was added again. The mixture was stirred at room temperature overnight, then poured out into H$_2$O and extracted with CH$_2$Cl$_2$. The organic layer was separated, dried, filtered and the solvent was evaporated. The residue was purified over silica gel on a glass filter (eluent: CH$_2$Cl$_2$/CH$_3$OH 98/2). The pure fractions were collected and the solvent was evaporated. The residue was crystallized from 2-propanol. The precipitate was filtered off and dried, yielding 3.4 g (79%) of [2S-[2α,4α[A(R*)]]]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(2-methoxy-1-phenylethyl)amino]-1-methylpropyl]-3α-1,2,4-triazol-3-one (compound 113).

EXAMPLE B9

A mixture of [2S-[2α,4α(R*,R*)]]-2-chloro-N-[2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl]acetamide (0.004 mol) in N-ethylethanamine (4 ml) and DMF (50 ml) was stirred at room temperature for 2 hours. H$_2$O and NaHCO$_3$ were added. The precipitate was filtered off, washed with H$_2$O and dried. The residue was purified over silica gel on a glass filter (eluent: CH$_2$Cl$_2$/CH$_3$OH 98/2). The pure fractions were collected and the solvent was evaporated. The residue was crystallized from 2-propanol. The precipitate was filtered off and dried, yielding 2.56 g (80%) of [2S-[2α,4α(R*,R*)]]-2-diethylamino-N-2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl]acetamide (compound 36; mp. 169.6° C.).

EXAMPLE B10

A mixture of compound 37 (0.0029 mol) and benzaldehyde (0.0029 mol) in methanol (250 ml) was hydrogenated at 50° C. overnight with Pd on activated carbon 10% (2 g) as a catalyst in the presence of thiophene solution (2 ml). After uptake of hydrogen, the catalyst was filtered off and the filtrate was evaporated. The residue was purified by column chromatography over silica gel (eluent: CH$_2$Cl$_2$/CH$_3$OH 98/2). The pure fractions were collected and the solvent was evaporated. The residue was triturated in DIPE and 2-propanol, filtered off and dried, yielding 1.1 g (48%) of [2S-[2α,4α(S*,R*)]]-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-[2-[(phenylmethyl)amino]-1-methylpropyl]-3H-1,2,4-triazol-3-one (compound 106; mp. 154.3° C.).

EXAMPLE B11 a) A mixture of benzaldehyde (0.0094 mol) and trimethylsilanecarbonitrile (0.01 mol) in CH$_2$Cl$_2$ (50 ml) was stirred for 20 minutes. Compound 37 (0.0022 mol) was added. The mixture was stirred overnight. The solvent was evaporated, yielding 2 g of [2S-[2α,4α(S*,R*)]]-α-[[2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl]amino]benzeneacetonitrile (compound 122).

b) Methanol (100 ml) was saturated with HCl. Compound 122 (0.0025 mol) was added. The mixture was stirred for 2 hours while HCl was bubbled through, then poured out into a Na$_2$CO$_3$ solution and extracted with CH$_2$Cl$_2$. The organic layer was separated, washed, dried, filtered and the solvent was evaporated. The residue was purified by column chromatography over silica gel (eluent: CH$_2$Cl$_2$/CH$_3$OH 98/2). The pure fractions were collected and the solvent was evaporated. The residue was triturated in DIPE, filtered off and dried, yielding 0.5 g [2S-[2α,4α(S*,R*)]]-α-[[2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxy-1H-1,2,4-triazol-1-yl]-1-methyl-propyl]amino]benzeneacetamide (compound 123).

c) A mixture of compound 122 (0.003 mol) in CH$_3$OH NH$_3$ (200 ml) was hydrogenated overnight with Raney Nickel (1 g) as a catalyst. After uptake of hydrogen (2 equivalents), the catalyst was filtered off and the filtrate was evaporated. The residue was triturated in DIPE and 2-propanol, filtered off and dried. The residue was purified by HPLC (eluent: (ammonium acetate 0.5% in H$_2$O/CH$_3$CN 90/10)/CH$_3$CN 90/10 to 0/100; column: HYPERPREP C18 BDS 8 µm). Two pure fractions were collected and their solvents were evaporated. The residue was triturated in DIPE, filtered off and dried, yielding 0.45 g [2S-[2α,4α[(S*,R*)(A)]]]-2-[2-[(2-amino-1-phenylethyl)amino]-1-methylpropyl]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihyro-3H-1,2,4-triazol-3-one (18.7%) (compound 174) and 0.37 g [2S-[2α,4α[(S*,R*)(B)]]]-2-[2[(2-amino-1-phenylethyl)amino]-1- methylpropyl]-4-[4-[4-[4-[[2-(2,4-difluorophenyl)-2-(1H-1, 2,4-triazol-1-ylmethyl)-1,3-dioxolan-4-yl]methoxy] phenyl]-1-piperazinyl]-phenyl]-2,4-dihydro-3H-1,2,4-triazol-3-one (15.4%) (compound 178).

d) Methanol (150 ml) was saturated with HCl on ice. Compound 122 (0.0025 mol) was added. The mixture was stirred and refluxed for 6 hours while HCl was bubbled through, then cooled and stirred at room temperature for the weekend. The solvent was evaporated partially. The concentrate was poured out into a $Na_2CO_3$ solution and extracted with $CH_2Cl_2$. The organic layer was separated, washed, dried, filtered and the solvent was evaporated. The residue was purified by column chromatography over silica gel (eluent: $CH_2Cl_2/CH_3OH$ 98/2). The pure fractions were collected and the solvent was evaporated, yielding 1g (60%) of methyl 2S-[2α,4α(S*,R*)]]-N-[2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]4,5-dihydro-5-oxo-1H-1,2,4-triazol-1-yl]-1-methylpropyl]-2-phenylglycine (compound 170).

EXAMPLE B12

A mixture of 4-(2-chloroethyl)morpholine hydrochloride (1.9 g), cis-4-[4-[4-[4-[2-(2,4-dichlorophenyl)-2-(1H-imidazolyl-1-ylmethyl)-1,3dioxolan-4-yl-methoxy]phenyl]-1-piperazinyl]phenyl]-2,4dihydro-5-methyl-3H-1,2,4-triazol-3-one (5 g), potassium hydroxide (2 g)in dimethyl sulfoxide (100 ml) was stirred for 24 hours at room temperature. The reaction mixture was poured onto water and then extracted with dichloromethane. The organic layer was washed with water, dried, filtered and the solvent was evaporated. The residue was purified by column chromatography over silica gel (eluent: $CHCl_3$/methanol 99/1). The pure fractions were collected and the eluent evaporated. The residue was crystallized from 4-methyl-2-pentanone, yielding 1.4 g (24%) of cis-4-[4-[4-[4-[[2-(2,4-dichlorophenyl)-2-(1H-imidazolyl-1-ylmethyl)-1,3-dioxolan-4-yl]methoxy] phenyl]-1-piperazinyl]phenyl]-2,4-dihydro-5-methyl-[2-(4-morpholinyl)ethyl]-3H-1,2,4-triazol-3-one (comp. 1; mp. 157.6° C.).

EXAMPLE B13

Intermediate 110 (0.0037 mol) was stirred in DMF (50 ml) under $N_2$ flow. NaH 60% (0.004 mol) was added. The mixture was stirred at 50° C. for 1 hour. (−)-(2S-cis)-2-(2, 4-difluorophenyl)-2-(1H-1,2,4-triazol-1-ylmethyl)-1,3-dioxolane-4-methanol methane-sulfonate(ester) (0.0045 mol) was added. The mixture was stirred at 80° C. for 5 hours and then cooled. $H_2O$ was added. The mixture was allowed to crystallize out. The precipitate was filtered off and dried. The residue was purified over silica gel on a glass filter (eluent 1: $CH_2Cl_2/CH_3OH$/ethylacetate/n-hexane 49/1/30/20 and eluent 2: $CH_2Cl_2/CH_3OH$ 97/3). The pure fractions were collected and the solvent was evaporated. The residue was crystallized from ethanol. The precipitate was filtered off and dried, yielding 1.73 g (57%) of ethyl [2S-[2α4α[A(R*)]]]-N-[2-[4-[4-[4-[4-[2-(2,4-difluorophenyl)-2-(1H-1,2,4-triazol-1-ylmethyl)-1,3-dioxolan-4-yl] methoxy]-phenyl]-1-piperazinyl]phenyl]-4,5-dihydro-5-oxo-1H-1,2,4-triazol-1-yl]-1-methyl-propyl]valine (compound 154).

EXAMPLE B14

A mixture of compound 37 (0.0044 mol) and [(1S)-1-formyl-2-phenylethyl]-carbamic acid 1,1-dimethylethyl ester (0.0044 mol) in $CH_2Cl_2$ (50 ml) was stirred at room temperature. Sodium tris(acetato-O)hydro-borate (I-) (0.007 mol) was added. The mixture was stirred for 2 hours. The residue was purified by column chromatography over silica gel (eluent: $CH_2Cl_2/CH_3OH$ 99/1 and 98/2). The pure fractions were collected and the solvent was evaporated. The residue was triturated in DIPE, filtered off and dried, yielding 3.2 g (79%) of 1,1-dimethylethyl [2S-[2α,4α[(S*, R*)]]]-[[[2-[4-[4-[4-[4-[[2-(2,4-difluorophenyl)-2-(1H-1,2, 4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl]amino]methyl](phenylmethyl) carbamate (compound 141).

EXAMPLE B15 a) A mixture of phenyl cis-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl] carbamate (0.005 mol), prepared according to the procedure described in EP-A-0,228,125 and (S)-1,2-dimethyl-N-(1-phenylethyl)ethanedianiine (0.005 mol) in dioxane (50 ml) was stirred for 3 hours. The solvent was evaporated. The residue was purified by column chromatography over silica gel (eluent: $CH_2Cl_2/CH_3OH$ 96/4) The pure fractions were collected and the solvent was evaporated. The residue was crystallized from diethyl ether. The precipitate was filtered off and dried, yielding 1.8 g (41%) of [2S-[2α,4α[2(1R*)]]]-N-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-N'-[1-methyl-2-[(1-phenylethyl)amino] propyl]urea trihydrochloride monohydrate (compound 197).

b) Trifluoroacetic acid (15 ml) was added dropwise to a stirring mixture of intermediate intermediate 133 (0.0025 mol) in $CH_2Cl_2$ (150 ml). The mixture was stirred for 4 hours, poured out into $H_2O$ and neutralized with $Na_2CO_3$. The organic layer was separated, washed, dried, filtered and the solvent was evaporated. The residue was purified by column chromatography over silica gel (eluent: $CH_2Cl_2/CH_3OH$ 96/4). The pure fractions were collected and the solvent was evaporated. The residue was triturated in DIPE and 2-propanol, filtered off and dried, yielding 1.42 g (74.7%) of (2S-cis)-N-[4-[4-4-[[2-(2,4-difluorophenyl)-2-(1H-1,2,4-triazol-1-ylmethyl)-1,3-dioxolane-4-yl]methoxy] phenyl]-1-piperazinyl]phenyl]-N'-methyl-N'-[1-methyl-2-[(phenylmethyl)amino]propyl]urea (compound 198).

EXAMPLE B16

A mixture of compound 204 (0.0014 mol) and acetophenone (0.042 mol) in toluene (100 ml) was hydrogenated at 150° C. for 16 hours with Pd/C 10% (1 g) as a catalyst in the presence of 1-butanethiol (1 ml; 4% solution in DIPE). After uptake of $H_2$ (1 equiv), the catalyst was filtered off and the filtrate was evaporated. The residue was triturated in DIPE, filtered off and recrystallized from 2-propanol. The precipitate was filtered off and dried, yielding 0.51 g (46%) of (2S-cis)-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[1-(1-phenylethyl)-4-piperidinyl]-3H-1,2,4-triazol-3-one (compound 199).

EXAMPLE B17

A mixture of compound 195 (0.0013 mol) in THF (100 ml) was hydrogenated at 125° C. (100 atm) for 16 hours with Pt/C 5% (0.5 g) as a catalyst. After uptake of $H_2$ (1 equiv), the catalyst was filtered off and the filtrate was evaporated. The residue was purified by column chromatography over silica gel (eluent: $CH_2Cl_2/CH_3OH$ 98/2). The pure fractions were collected and the solvent was evaporated. The residue was triturated in DIPE, filtered off and dried, yielding 0.28 g (28%) of (2S-cis)-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4-[2-[(phenylmethyl)amino]-1-methylethyl]-2-imidazolidinone (compound 196).

Tables 2 through 8 list compounds of formula (I) which illustrate the present invention and are made according to one of the above examples.

TABLE 2

[Structural formula shown]

| Co. No. | Ex. No. | X | $R_a$ | $R_b$ | $R_c$ | —NR$^1$R$^2$ | stereochemistry; $[\alpha]_{20}^D$ @ concentration (in mg/5 ml DMF); salts; melting point (in °C.) |
|---|---|---|---|---|---|---|---|
| 1 | B12 | CH | Cl | CH$_3$ | H | 4-morpholinyl | cis; mp. 157.6 |
| 2 | B12 | CH | Cl | H | H | 4-morpholinyl | cis; mp. 193.3 |
| 3 | B12 | N | Cl | CH$_3$ | H | 4-morpholinyl | cis; mp. 159.9 |
| 4 | B12 | N | Cl | H | H | 4-morpholinyl | cis; mp. 195.5 |
| 5 | B1a | N | F | H | CH$_3$ | 4-morpholinyl | (2S-cis) |
| 6 | B12 | CH | Cl | CH$_3$ | H | 1-pyrrolidinyl | cis; mp. 148.1 |
| 7 | B12 | CH | Cl | H | H | 1-pyrrolidinyl | cis; mp. 204 |
| 8 | B1a | N | F | H | CH$_3$ | 1-pyrrolidinyl | [2S-[2α,4α(A)]] |
| 9 | B1a | N | F | H | CH$_3$ | 2-(HO—CH$_2$)-1-pyrrolidinyl | [2S-[2α,4α[(A + B)(R*)]]] |
| 10 | B1a | N | F | H | CH$_3$ | 2-(HO—CH$_2$)-1-pyrrolidinyl | [2S-[2α,4α[(A + B)(S*)]]] |
| 11 | B12 | CH | Cl | CH$_3$ | H | 1-piperidinyl | cis; mp. 146.8 |
| 12 | B12 | CH | Cl | H | H | 1-piperidinyl | cis; mp. 188.1 |
| 13 | B12 | N | Cl | H | H | 1-piperidinyl | cis; mp. 183.5; H$_2$O (1:1) |
| 14 | B1a | N | F | H | CH$_3$ | [piperidinyl-NH-C(=O)-O-C(CH$_3$)$_3$] | (2S-cis) |
| 15 | B1a | N | F | H | CH$_3$ | [piperidinyl-CH$_2$-N(CH$_3$)$_2$] | (2S-cis) |
| 16 | B1a | N | F | H | CH$_3$ | [piperidinyl-CH$_2$-CH$_2$-N(CH$_3$)$_2$] | (2S-cis) |
| 17 | B1b | N | F | H | CH$_3$ | 4-amino-1-piperidinyl | (2S-cis) |
| 18 | B1a | N | F | H | CH$_3$ | [piperidinyl-N(CH$_3$)$_2$] | [2S-[2α,4α(A)]] |
| 19 | B5a | N | F | H | CH$_3$ | —N=N$^+$=N$^−$ | [2S-[2α,4α(R*,S*)]] +10.71° @ 24.74 |
| 20 | B1a | N | F | H | CH$_3$ | 4-phenyl-1-piperazinyl | (2S-cis) |
| 21 | B1a | N | F | H | CH$_3$ | 4-methyl-1-piperazinyl | [2S-[2α,4α(A)]] |
| 22 | B1a | N | F | H | CH$_3$ | 4-(2-hydroxyethyl)-1-piperazinyl | (2S-cis) |

TABLE 3

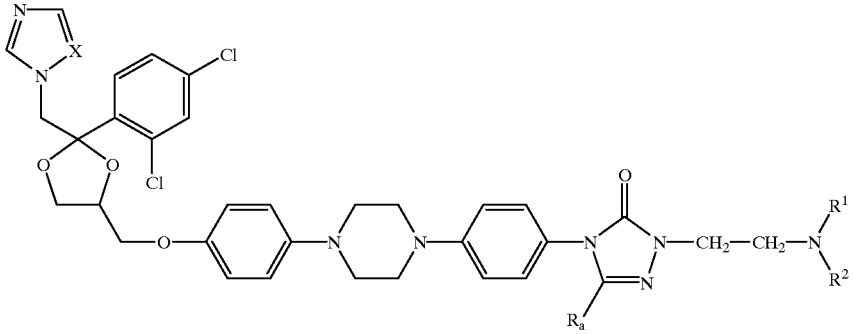

| Co. No. | Ex. No. | X | $R_a$ | $R^1$ | $R^2$ | stereochemistry and melting point in °C. |
|---|---|---|---|---|---|---|
| 23 | B12 | CH | $CH_3$ | $CH_3$ | $CH_3$ | cis; mp. 184.3 |
| 24 | B12 | CH | $CH_3$ | $CH_2$—$CH_3$ | $CH_2$—$CH_3$ | cis; mp. 110 |
| 25 | B12 | CH | H | $CH_3$ | $CH_3$ | cis; mp. 203.6 |
| 26 | B12 | CH | H | $CH_2$—$CH_3$ | $CH_2$—$CH_3$ | cis; mp. 140.3 |
| 27 | B12 | N | H | $CH_2$—$CH_3$ | $CH_2$—$CH_3$ | cis; mp. 177.8 |

TABLE 4

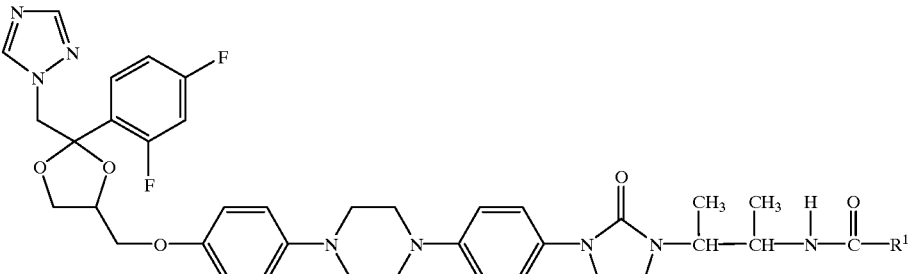

| Co. No. | Ex. No. | $R^1$ | stereochemistry; optical rotation as $[\alpha]^D_{20}$ @ concentration (in mg/5 ml DMF); salts; melting point (in °C.) |
|---|---|---|---|
| 28 | B1a | O—$C(CH_3)_3$ | [2S-[2α,4α(S*,R*)]]; +3.03° @ 19.80 mg/2 ml; mp 158.3 |
| 29 | B1a | O—$C(CH_3)_3$ | [2S-[2α,4α(R*,R*)]]; −27.68° @ 21.39 mg/2 ml; mp 147.4 |
| 30 | B1a | O—$C(CH_3)_3$ | [2S-[2α,4α(S*,S*)]]; +5.64° @ 24.82; mp. 194.6 |
| 31 | B1a | O—$C(CH_3)_3$ | [2S-[2α,4a(R*,S*)]]; −25.56° @ 25.43; mp. 190.2 |
| 32 | B3 | $CH_2$—Cl | [2S-[2α,4α(R*,S*)]] |
| 33 | B3 | $CH_2$—Cl | [2S-[2α,4α(R*,R*)]]; −38.55° @ 25.16; mp. 126.8 |
| 34 | B9 | $CF_3$ | [2S-[2α,4α(R*,S*)]]; −11.24° @ 25.36; mp. 192.4 |
| 35 | B9 | $CH_2$—$N(CH_2CH_3)_2$ | [2S-[2α,4α(R*,S*)]]; −24.98° @ 26.22; mp. 140.5 |
| 36 | B9 | $CH_2$—$N(CH_2CH_3)_2$ | [2S-[2α,4α(R*,R*)]]; −43.57° @ 24.9; mp. 169.6 |

TABLE 5

| Co. No. | Ex. No. | R¹ | R² | $R_a$ | stereochemistry; optical rotation as $[\alpha]^D_{20}$ @ concentration (in mg/5 ml DMF); salts and melting point (in °C.) |
|---|---|---|---|---|---|
| 37 | B1b | H | H | F | [2S-[2α,4α(S*,R*)]]; −11.68 @ 19.87 mg/2 ml; mp 168.5 |
| 38 | B1b | H | H | F | [2S-[2α,4α(S*,S*)]]; −17.92° @ 25.39; mp 176.8 |
| 39 | B1b | H | H | F | [2S-[2α,4α(R*,R*)]]; −9.23° @ 24.92; mp 167.9 |
| 40 | B1b | H | H | F | [2S-[2α,4α(R*,S*)]]; −13.43 @ 25.31; mp 169.3 |
| 41 | B1a | $CH_3$ | $CH_3$ | F | [2S-[2α4α[(B1 + B2)(R*,S*)]]]; −10.92° @ 24.72; mp 180.1 |
| 42 | B1a | $CH_3$ | H | F | (2S-cis); −13.68° @ 24.85; mp 119.2 |
| 43 | B1a | $(CH_2)_3$-phenyl | H | F | (2S,cis) |
| 44 | B10 | $(CH_2)_3$-phenyl | H | F | [2S-[2α,4α(S*,S*)]]; +3.50° @ 24.32; mp 122.3 |
| 45 | B10 | $(CH_2)_3$-phenyl | H | F | [2S-[2α,4α(R*,R*)]]; −27.420 @ 23.89; mp 127.5 |
| 46 | B10 | $(CH_2)_3$-phenyl | H | F | [2S-[2α,4α(R*,S*)]]; −30.72° @ 24.9; mp 146.8 |
| 47 | B10 | $(CH_2)_3$-phenyl | H | F | [2S-[2α4,α(S*,R*)]]; +5.45° @ 26.6; mp. 138.0 |
| 48 | B1a | $CH(CH_3)_2$ | H | F | (2S-cis) |
| 49 | B1a | $CH_2$-(tetrahydrofuran-2-yl) | H | F | (2S-cis) |
| 50 | B1a | $(CH_2)_2$-OH | $CH_3$ | F | (2S-cis) |
| 51 | B1a | $(CH_2)_2$-OH | H | F | (2S-cis) |
| 52 | B1a | $(CH_2)_2$-O-phenyl | H | F | (2S-cis) |
| 53 | B1a | $(CH_2)_2$-O-phenyl | $CH_3$ | F | (2S-cis) |
| 54 | B1a | $(CH_2)_2$-O—$CH_2$-phenyl | H | F | (2S-cis) |
| 55 | B1a | indan-2-yl | H | F | (2S-cis) |
| 56 | B10 | indan-2-yl | H | F | [2S-[2α,4α(S*,S)]] |
| 57 | B10 | indan-2-yl | H | F | [2S-[2α,4α(R*,S*)]]; −43.63° @ 24.18; mp 161.9 |
| 58 | B10 | indan-2-yl | H | F | [2S-[2α,4α(S*,R*)]]; +19.31 @ 25.89; mp 174 |
| 59 | B10 | indan-2-yl | H | F | [2S-[2α,4α(R*,R*)]]; −25.64° @ 24.96; mp 178.1 |
| 60 | B1a | $CH_2$-(pyridin-2-yl) | H | F | (2S-cis); HCl (1:3); $H_2O$ (1:1) |
| 61 | B1a | 1-benzyl-piperidin-4-yl | H | F | [2S-[2α,4α(R*,S*)]] + [2S-[2α,4α(S*,R*)]] |
| 62 | B1a | 1-benzyl-piperidin-4-yl | H | F | [2S-[2α,4α(R*,R*)]] + [2S-[2α,4α(S*,S*)]]; −9.91° @ 24.73; mp 92.8 |
| 63 | B6a | piperidin-4-yl | H | F | [2S-[2α,4α(R*,S*)]]; diisopropyletherate(1:1) |
| 64 | B6b | 1-methyl-piperidin-4-yl | H | F | [2S-[2α,4α(R*,S*)]] + [2S-[2α,4α(S*,R*)]] |
| 65 | B1a | $CH_2$—$CH_2$—$N(CH_3)_2$ | H | F | (2S-cis) |
| 66 | B1a | $(CH_2)_3$—$N(CH_3)_2$ | $CH_3$ | F | [2S-[2α,4α(A)]] |
| 67 | B1a | $(CH_2)_3$—$N(CH_3)_2$ | H | F | (2S-cis) |
| 68 | B1a | $(CH_2)_3$—NH—$CH_2$-phenyl | H | F | (2S-cis) |
| 69 | B6a | $(CH_2)_3$—$NH_2$ | H | F | (2S-cis) |
| 70 | B1a | $CH(CH_2OH)_2$ | H | F | (2S-cis) |
| 71 | B1a | —CH($CH_2OH$)—CH($CH_3$)$CH_3$ | H | F | [2S-[2α,4α[[(R*,R*) (R*)] + [(R*,S*)(R*)]]]] |
| 72 | B1a | —CH($CH_2OH$)—CH($CH_3$)$CH_3$ | H | F | [2S-[2α,4α[(S*,S*)(R*)]]]; −6.97° @ 24.38; mp. 154 |
| 73 | B1a | —CH($CH_2OH$)—CH($CH_3$)$CH_3$ | H | F | [2S-8 2α,4α[(R*,S*)(R*)]]]; −40.33° @ 25.79; mp. 151.1 |
| 74 | B1a | $(CH_2)_2$-phenyl | H | F | (2S-cis) |
| 75 | B10 | $(CH_2)_2$-phenyl | H | F | [2S-[2α,4α(R*,R*)]]; −22.71° @ 23.56; mp 129.2 |
| 76 | B10 | $(CH_2)_2$-phenyl | H | F | [2S-[2α,4α(S*,S*)]]; +9.47° @ 23.77; mp 157.3 |
| 77 | B10 | $(CH_2)_2$-phenyl | H | F | [2S-[2α,4α(R*,S*)]]; −30.12° @ 24.4; mp 122.2 |
| 78 | B10 | $(CH_2)_2$-phenyl | H | F | [2S-[2α,4α(S*,R*)]]; +4.17° @ 23.99; mp 148.5 |

TABLE 5-continued

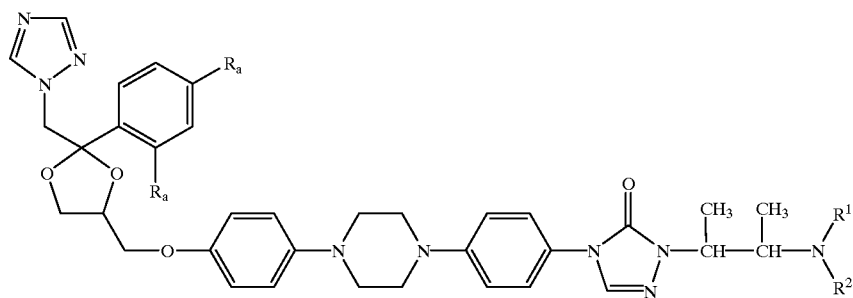

| Co. No. | Ex. No. | R¹ | R² | Rₐ | stereochemistry; optical rotation as $[\alpha]^D_{20}$ @ concentration (in mg/5 ml DMF); salts and melting point (in ° C.) |
|---|---|---|---|---|---|
| 79 | B1a | —CH(CH₂OH)—CH₂—C₆H₅ | H | F | [2S-[2α,4α[A(S*)]]]; +23.38° @ 25.88; mp. 154.1 |
| 80 | B1a | —CH(CH₂OH)—CH₂—C₆H₅ | H | F | [2S-[2α,4α[A(R*)]]]; −44.24° @ 24.3 |
| 81 | B4a | —CH₂—CH(OH)—CH₂—C₆H₅ | H | F | [2S-[2α,4α[(S*,R*)(R*)]]] |
| 82 | B4a | —CH₂—CH(OH)—CH₂—C₆H₅ | H | F | [2S-[2α,4α[(S*,R*)(S*)]]]; diisopropyletherate(1:1) |
| 138 | B1a | —CH(CH₂OH)—CH(CH₃)₂ | H | Cl | [2S-[2α,4α[B(R*)]]]; −44.17° @ 24.79; mp 110 |
| 139 | B1a | —CH(CH₂OH)—CH(CH₃)₂ | H | F | [2S-[2α,4α[(S*,R*)(R*)]]]; +17.36° @ 24.77; mp 126 |
| 140 | B1a | —CH(CH₂OH)—CH(CH₃)₂ | H | F | [2S-[2α,4α[(R*,R*)(R*)]]]; −20.29° @ 24.64; mp 130 |
| 141 | B14 | —CH₂—CH(NHC(O)OC(CH₃)₃)—CH₂—C₆H₅ | H | F | [2S-[2α,4α[(S*,R*)(R*)]]]; mp 121 |
| 142 | B1b | —CH₂—CH(NH₂)—CH₂—C₆H₅ | H | F | [2S-[2α,4α[(S*,R*)(R*)]]]; +9.60° @ 25; mp 125 |

TABLE 5-continued

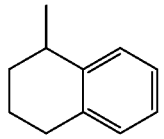

| Co. No. | Ex. No. | R¹ | R² | R_a | stereochemistry; optical rotation as $[\alpha]^D_{20}$ @ concentration (in mg/5 ml DMF); salts and melting point (in ° C.) |
|---|---|---|---|---|---|
| 143 | B1a | 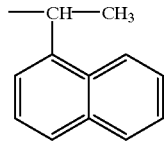 | H | F | [2S-[2α,4α(B)]]; −8.46° @ 24.82; mp 120 |
| 144 | B1a | —CH—CH₃ (1-naphthyl) | H | F | [2S-[2α,4α[(S*,R*) (R*)]]] |
| 145 | B1a | 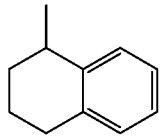 | H | F | [2S-[2α,4α(A)]] |
| 146 | B1a | —CH₂-(2-thienyl) | H | F | [2S-[2α,4α(S*,R*)]]; +16.63° @ 25.25; mp 146 |
| 147 | B1a | 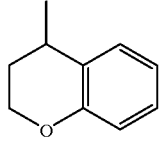 | H | F | [2S-[2α,4α(B)]] |
| 148 | B1a | 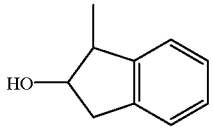 | H | F | [2S-[2α,4α[B-(R*,S*)]]] |
| 149 | B1a | —CH₂-(3-thienyl) | H | F | [2S-[2α,4α(S*,R*)]]; +14.71° @ 25.5; mp 112 |
| 150 | B1a | —CH₂-(2-pyridinyl) | H | F | [2S-[2α,4α(S*,R*)]]; +10.78° @ 10.2 |
| 151 | B1a | —CH₂-(3-pyridinyl) | H | F | [2S-[2α,4α(S*,R*)]]; +32.79° @ 9.15; mp. 161 |
| 152 | B1a | —CH₂-phenyl | H | F | [2R-[2α,4α(S*,S*)]]; −17.60° @ 25.85; mp 162 |
| 153 | B1a | 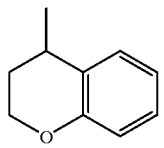 | H | F | [2S-[2α,4α(A)]] |

TABLE 5-continued

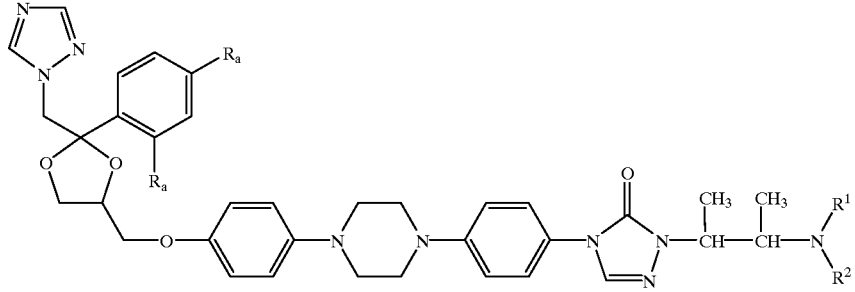

| Co. No. | Ex. No. | R¹ | R² | Rₐ | stereochemistry; optical rotation as [α]$^D_{20}$ @ concentration (in mg/5 ml DMF); salts and melting point (in ° C.) |
|---|---|---|---|---|---|
| 154 | B13 | 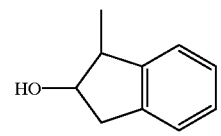 | H | F | [2S-[2α,4α[A(R*)]]]; −39.57° @ 27.8; mp 131 |
| 155 | B1a | —CH₂-(4-pyridinyl) | H | F | [2S-[2α,4α(S*,R*)]]; +10.57° @ 25.06; mp 109 |
| 156 | B1a | 2,3-dihydro-1H-inden-1-yl | H | F | (2S-cis) |
| 157 | B1a | 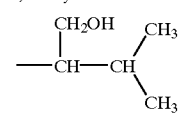 | H | F | [2S-[2α,4β[B(R*)]]] + [2R-[2α,4β[B(S*)]]] |
| 158 | B1a | 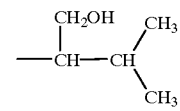 | H | Cl | [2R-[2α,4α[B(S*)]]] |
| 159 | B1a | CH₂—1H-imidazol-2-yl | H | F | [2S-[2α,4α(S*,R*)]]; +11.38° @ 23.72 |
| 160 | B1a | 2,3-dihydro-1H-inden-1-yl | H | F | [2S-[2α,4α(B)]] |
| 161 | B1a | 2,3-dihydro-2-hydroxy-1H-inden-1-yl | H | F | [2S-[2α,4α[B-(S*,R*)]]] |
| 162 | B1a | 2,3-dibydro-2-hydroxy-1H-inden-1-yl | H | F | [2S-[2α,4α[A-(R*,S*)]]] |
| 205 | B1a | 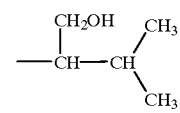 | H | F | [2S-[2α,4α[(S*,S*)(S*)]]]; −4.18° @ 24.64; mp 95 |
| 206 | B1a | 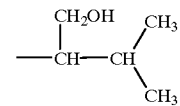 | H | F | [2S-[2α,4α[(R*,S*)(S*)]]]; −43.59° @; mp 146 |
| 207 | B1a | 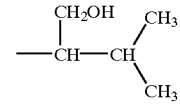 | H | F | [2S-[2α,4α[(S*,R*)(S*)]]]; +16.12° @; mp 130 |
| 208 | B1a | 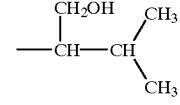 | H | F | [2S-[2α,4α[(R*,R*)(S*)]]]; −17.71° @; mp 154 |

TABLE 6

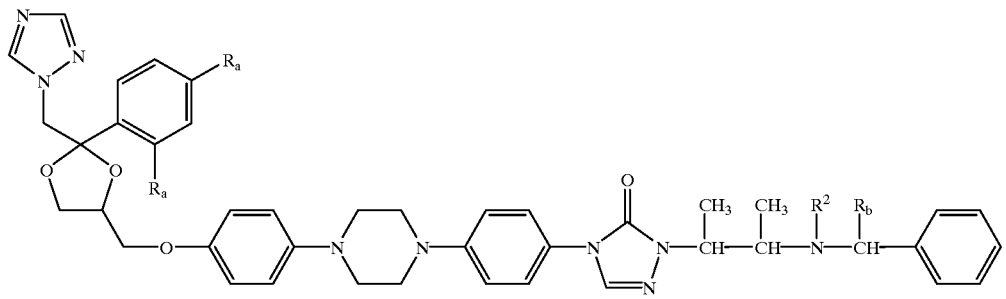

| Co. No. | Ex. No. | $R_a$ | $R^2$ | $R_b$ | stereochemistry | optical rotation as $[\alpha]^D_{20}$ @ concentration (in mg/5 ml DMF); salts and melting point (in ° C.) |
|---|---|---|---|---|---|---|
| 89 | B1a | F | CH₃ | CH₃ | [2S-[2α,4α[(R*,S*)(S*)]]] | −20.40° @ 24.26; mp 205.3 |
| 90 | B1a | F | CH₃ | CH₃ | [2S-[2α,4α[(S*,R*)(R*)]]] | −1.17° @ 25.75; mp 200.7 |
| 91 | B1a | F | CH₃ | CH₃ | [2S-[2α,4α[(R*,R*)(R*)]]] | −23.07° @ 27.09; mp 148.4 |
| 92 | B1a | F | CH₃ | CH₃ | [2S-[2α,4α[(S*,S*)(S*)]]] | +1.80° @ 24.97 |
| 163 | B1a | Cl | H | CH₃ | [2S-[2α,4α[(R*,S*)(S*)]]] | −11.64° @ 25.34; mp 131 |
| 164 | B1a | Cl | H | CH₃ | [2R-[2α,4α[(S*,R*)(R*)]]] | +18.57° @ 23.96; mp 129 |
| 165 | B1a | Cl | H | H | [2S-[2α,4α(S*,R*)]] | +12.03° @ 23.69; mp 124 |
| 166 | B1a | Cl | H | H | [2R-[2α,4α(R*,S*)]] | +43.88° @ 25.41 |

TABLE 7

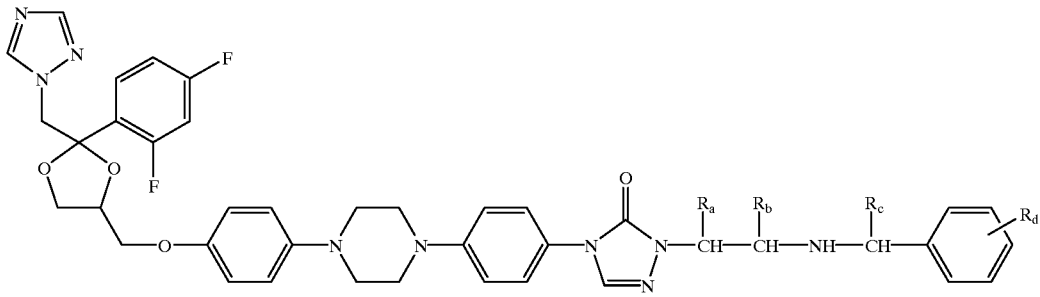

| Co. No. | Ex. No. | $R_a$ | $R_b$ | $R_c$ | $R_d$ | stereochemistry | optical rotation as $[\alpha]^D_{20}$ @ concentration (in mg/5 ml DMF); salts and melting point (in ° C.) |
|---|---|---|---|---|---|---|---|
| 83 | B1a | CH₃ | CH₃ | CH₃ | H | [2S-[2α,4α[(S*,R*)(R*)]]] | −15.78 @ 25.35; mp 129 |
| 84 | B1a | CH₃ | CH₃ | CH₃ | H | [2S-[2α,4α[(R*,R*)(R*)]]] | −73.48° @ 25.79; mp 139.8 |
| 85 | B1a | CH₃ | CH₃ | CH₃ | H | [2S-[2α,4α[(S*,S*)(S*)]]] | −11.10° @ 25.67; HCl (1:1) |
| 86 | B1a | CH₃ | CH₃ | CH₃ | H | [2S-[2α,4α[(R*,S*)(S*)]]] | −22.86° @ 25.37; HCl (1:1) 2-propanolate(1:1) |
| 87 | B1a | CH₃ | CH₃ | CH₃ | H | [2S-[2α,4α[(S*,S*)(S*)]]] | — |
| 88 | B1a | CH₃ | CH₃ | CH₃ | H | [2S-[2α,4α[(R*,S*)(S*)]]] | — |
| 93 | B1a | CH₃ | CH₃ | H | 2-F | (2S-cis) | — |
| 94 | B10 | CH₃ | CH₃ | H | 2-F | [2S-[2α,4α(S*,S*)]] | +17.14° @ 25.38; mp 144.1 |
| 95 | B10 | CH₃ | CH₃ | H | 2-F | [2S-[2α,4α(R*,R*)]] | −40.11° @ 24.31; mp 124.7 |
| 96 | B10 | CH₃ | CH₃ | H | 2-F | [2S-[2α,4α(R*,S*)]] | −36.21° @ 24.72; mp 155.3 |
| 97 | B10 | CH₃ | CH₃ | H | 2-F | [2S-[2α,4α(S*,R*)]] | +12.82° @ 23.8; mp 147.9 |
| 98 | B1a | CH₃ | CH₃ | CH₃ | 4-F | (2S-cis) | — |
| 99 | B1a | CH₃ | CH₃ | CH₃ | 4-F | [2S-[2α,4α[A(R*)]]] | −70.05° @ 25.41; mp 148.2 |
| 100 | B1a | CH₃ | CH₃ | CH₃ | 4-F | [2S-[2α,4α[B(R*)]]] | −15.79° @ 25.96; mp 131 |
| 101 | B1a | CH₃ | CH₃ | H | H | [2S-[2α,4α(R*,S*)]] + [2S-[2α,4α(S*,R*)]] | — |
| 102 | B1a | CH₃ | CH₃ | H | H | [2S-[2α,4α(R*,R*)]] + [2S-[2α,4α(S*,S*)]] | — |
| 103 | B10 | CH₃ | CH₃ | H | H | [2S-[2α,4α(S*,S*)]] | +16.49° @ 23.05; mp 159.9 |
| 104 | B10 | CH₃ | CH₃ | H | H | [2S-[2α,4α(R*,R*)]] | −41.23° @ 22.8; mp 128.5 |
| 105 | B10 | CH₃ | CH₃ | H | H | [2S-[2α,4α(R*,S*)]] | −41.04° @ 24.49; mp 152.1 |
| 106 | B10 | CH₃ | CH₃ | H | H | [2S-[2α,4α(S*,R*)]] | +16.88° @ 24.0; mp 154.3 |
| 107 | B1a | CH₃ | CH₃ | H | 2-OCH₃ | (2S-cis) | — |
| 108 | B1a | CH₃ | CH₃ | H | 2-CH₂OH | (2S-cis) | — |
| 109 | B1a | CH₃ | CH₃ | CH₂OH | H | [2S-[2α,4α[A(R*)]]] | −9.57° @ 25.08; mp 113.5 |
| 110 | B1a | CH₃ | CH₃ | CH₂OH | H | [2S-[2α,4α(R*)]] | +45.51° @ 25.27; mp 119.9 |
| 111 | B1a | CH₃ | CH₃ | CH₂OH | H | [2S-[2α,4α[A(S*)]]] | −68.16° @ 25.82; mp 125 |
| 112 | B1a | CH₃ | CH₃ | CH₂OH | H | [2S-[2α,4α[B(S*)]]] | −12.90° @ 25.19; mp 151.7 |

TABLE 7-continued

| Co. No. | Ex. No. | $R_a$ | $R_b$ | $R_c$ | $R_d$ | stereochemistry | optical rotation as $[\alpha]^D_{20}$ @ concentration (in mg/5 ml DMF); salts and melting point (in ° C.) |
|---|---|---|---|---|---|---|---|
| 113 | B8 | $CH_3$ | $CH_3$ | $CH_2OCH_3$ | H | [2S-[2α,4α[A(R*)]]] | 0.00° @ 24.3 |
| 114 | B1a | H | H | $CH_3$ | H | [2S-[2α,4α(S*)] | +4.35° @ 25.29; mp 130.6 |
| 115 | B5b | H | H | $CH_3$ | H | [2S-[2α,4α(R*)]] | −27.32° @ 24.16; mp 110.2 |
| 116 | B1a | H | $CH_3$ | $CH_3$ | H | [2S-[2α,4α[2A(R*)]]] | −45.70° @ 23.74; mp 111.6 |
| 117 | B1a | H | $CH_3$ | $CH_3$ | H | [2S-[2α,4α[2B(S*)]]] | +25.78° @ 25.02; mp 112 |
| 118 | B5c | $CH_3$ | H | $CH_3$ | H | [2S-[2α,4α[R*(S*)]]] + [2S-[2α,4α[S*(S*)]] | −2.74° @ 23.74; mp 114.9 |
| 119 | B5d | $CH_3$ | H | $CH_3$ | H | [2S-[2α,4α[R*(R*)]]] + [2S-[2α,4α[S*(R*)]] | — |
| 120 | B5b | $C_2H_5$ | H | $CH_3$ | H | [2S-[2α,4α[(A + B)(S*)]]] | — |
| 121 | B5b | $C_2H_5$ | H | $CH_3$ | H | [2S-[2α,4α(R*(R*))]]] + [2S-[2α,4α[S*(R*)]] | — |
| 122 | B11a | $CH_3$ | $CH_3$ | CN | H | [2S-[2α,4α(S*,R*)]] | — |
| 123 | B11a | $CH_3$ | $CH_3$ | C(=O)$NH_2$ | H | [2S-[2α,4α(S*,R*)]] | — |
| 167 | B1a | $CH_3$ | $CH_3$ | $CH_3$ | 4-F | [2S-[2α,4α[A(S*)]]] | +48.90° @ 24.03; mp 161.5 |
| 168 | B1a | $CH_3$ | $CH_3$ | $CH_3$ | 4-F | [2S-[2α,4α[B(S*)]]] | −6.58° @ 25.06; mp 132 |
| 169 | B8 | $CH_3$ | $CH_3$ | H | 2-$CH_2$—O—$CH_3$ | [2S-[2α,4α(A)]] | −10.55° @ 24.18; mp 152 |
| 170 | B11d | $CH_3$ | $CH_3$ | C(O)O$CH_3$ | H | [2S-[2α,4α(S*,R*)]] | — |
| 171 | B8 | $CH_3$ | $CH_3$ | H | 2-$CH_2$—O—$CH_3$ | [2S-[2α,4α(B)]] | — |
| 172 | B4b | $CH_3$ | $CH_3$ | $CH_2$—N($CH_3$)$_2$ | H | [2S-[2α,4α[(S*,R*)(S*)]]] | — |
| 173 | B11c | $CH_3$ | $CH_3$ | H | 2-$CH_2$—$NH_2$ | [2S-[2α,4α(R*,S*)]] | — |
| 174 | B11c | $CH_3$ | $CH_3$ | $CH_2$—$NH_2$ | H | [2S-[2α,4α[(S*,R*)(A)]]] | +43.20° @ 23.84; mp 158 |
| 175 | B1a | $CH_3$ | H | H | H | (2S-cis) | — |
| 176 | B1a | $CH_3$ | $CH_3$ | H | H | [2R-[2α,4α(R*,S*)]] | +41.75° @ 25.27; mp 152 |
| 177 | B1a | $CH_3$ | $CH_3$ | H | H | [2R-[2α,4α(R*,R*)]] | +40.97° @ 26.85; mp 128 |
| 178 | B11c | $CH_3$ | $CH_3$ | $CH_2$—$NH_2$ | H | [2S-[2α,4α[(S*,R*)(B)]]] | — |
| 179 | B1a | $CH_3$ | $CH_3$ | H | 2-$CH_2$—N($CH_3$)$_2$ | (2S-cis) | — |
| 180 | B1a | $CH_3$ | $CH_3$ | H | H | [2R-[2α,4α(S*,R*)]] | −17.47° @ 25.19; mp 158 |
| 181 | B1a | $C_2H_5$ | $CH_3$ | $CH_3$ | H | [2S-[2α,4α[A(R*)]]] | — |
| 182 | B1a | $CH_3$ | $CH_3$ | H | H | [2R-[2α,4β(R*,S*)]] + [2S-[2α,4β(S*,R*)]] | — |
| 183 | B1a | $CH_3$ | $CH_3$ | H | H | [2R-[2α,4β(S*,S*)]] + [2S-[2α,4β(R*,R*)]] | — |
| 184 | B1a | $C_2H_5$ | $CH_3$ | $CH_3$ | H | [2S-[2α,4α[B(R*)]]] | — |

TABLE 8

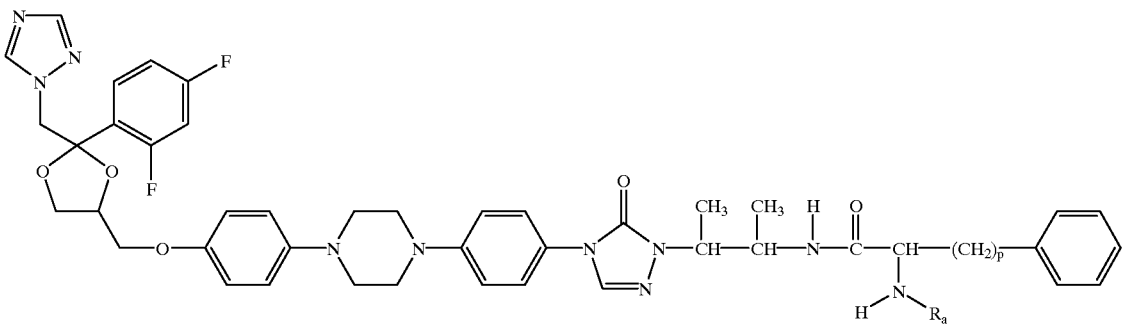

| Co. No. | Ex. No. | $R_a$ | p | stereochemistry | optical rotation as $[\alpha]^D{}_{20}$ @ concentration (in mg/5 ml DMF); salts and melting point (in °C.) |
|---|---|---|---|---|---|
| 124 | B2 | C(=O)—O—C(CH$_3$)$_3$ | 1 | [2S-[2α,4α[(S*,R*)(R*)]]] | +3.72° @ 19.89 mg/2 ml; mp. 181.7 |
| 125 | B2 | C(=O)—O—C(CH$_3$)$_3$ | 1 | [2S-[2α,4α[(S*,S*)(R*)]]] | mp. 273.5 |
| 126 | B2 | C(=O)—O—C(CH$_3$)$_3$ | 1 | [2S-[2α,4α[(R*,S*)(R*)]]] | −17.78° @ 24.19; mp 101.8 |
| 127 | B2 | C(=O)—O—C(CH$_3$)$_3$ | 1 | [2S-[2α,4α[(R*,R*)(R*)]]] | −39.88° @ 25.2; mp 126.3 |
| 128 | B2 | C(=O)—O—C(CH$_3$)$_3$ | 1 | [2S-[2α,4α[(R*,R*)(S*)]]] | −24.21° @ 25.82 mg/5 ml in methanol |
| 129 | B2 | C(=O)—O—C(CH$_3$)$_3$ | 0 | [2S-[2α,4α[(R*,S*)(R*)]]] | +5.02° @ 23.89; mp 158.4 |
| 130 | B1b | H | 1 | [2S-[2α,4α[(S*,R*)(R*)]]] | +1.65° @ 20.63 mg/2 ml; mp. 170.8 |
| 131 | B1b | H | 1 | [2S-[2α,4α[(S*,S*)(R*)]]] | +5.50° @ 25.46; mp 113.2 |
| 132 | B1b | H | 1 | [2S-[2α,4α[(R*,S*)(R*)]]] | 29.69° @ 26.1; mp 170.8 |
| 133 | B1b | H | 1 | [2S-[2α,4α[(R*,R*)(R*)]]] | 48.09° @ 24.85; mp 151.2 |
| 134 | B7 | H | 1 | [2S-[2α,4α[(R*,R*)(R*)]]]; | HCl (1:1) |
| 135 | B1b | H | 1 | [2S-[2α,4α(R*,R*)(S*)]]] | −33.12° @ 25.97; HCl (1:2) H$_2$O (1:2) |
| 136 | B1b | H | 1 | [2S-[2α,4α[(S*,R*)(R*)]]] | HCl (1:1) H$_2$O (1:1) |
| 137 | B1b | H | 0 | [2S-[2α,4α[(R*,S*)(R*)]]] | −11.33° @ 23.84; mp 184.6 |

TABLE 9

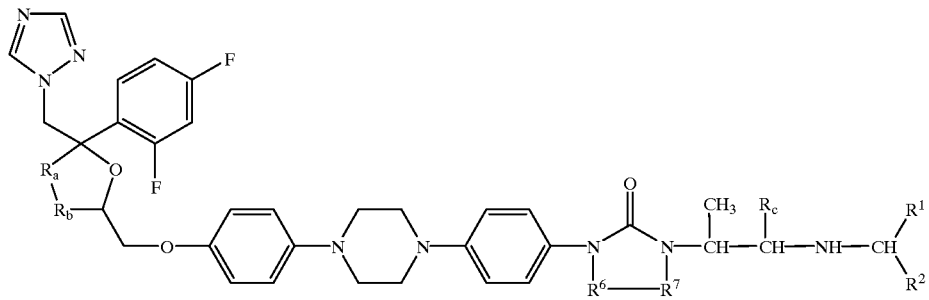

| Co. No. | Ex. No. | $R_a$ | $R_b$ | $R_c$ | $R^6$–$R^7$ | $R^1$ | $R^2$ | stereochemistry; $[\alpha]^D{}_{20}$ @ concentration (in mg/5ml DMF); salts; melting point (°C.) |
|---|---|---|---|---|---|---|---|---|
| 185 | B1a | CH$_2$ | O | CH$_3$ | CH=N | CH$_3$ | phenyl | [2S-[2α[(R*,S*)(S*)],4α]]; +18.35° @ 25.61; mp 154 |
| 186 | B1a | CH$_2$ | O | CH$_3$ | CH=N | H | phenyl | [2S-[2α,4α(S*,R*)]]; +43.37° @ 25.02; mp 138 |
| 187 | B1a | O | CH$_2$ | CH$_3$ | N=CH | H | phenyl | [2S-[2α,4α(R*,R*)]] + [2S-[2α,4α(S*,R*)]] |
| 188 | B1a | O | CH$_2$ | CH$_3$ | N=CH | H | phenyl | [2S-[2α,4α(R*,R*)]] + [2S-[2α,4α(S*,S*)]] |
| 189 | B1a | CH$_2$ | O | CH$_3$ | CH=N | CH$_2$—OH | CH(CH$_3$)$_2$ | [2S-[2α,4α[B(R*)]]] |
| 190 | B1a | O | CH$_2$ | CH$_3$ | CH=CH | CH$_3$ | phenyl | [2S-[2α[A(R*)]]] |
| 191 | B1a | CH$_2$ | O | CH$_3$ | CH$_2$—CH$_2$ | CH$_3$ | phenyl | [2S-[2α[B,(S*)],4α]] |
| 192 | B1a | CH$_2$ | O | CH$_3$ | CH=CH | CH$_3$ | phenyl | [2S-[2α, 4α[A(R*)]]] + [2S-[2α,4α[B(R*)]]] |
| 193 | B1a | O | CH$_2$ | CH$_3$ | CH$_2$—CH$_2$ | CH$_3$ | phenyl | [2S-[2α,4α[B,(S*)]]] |
| 194 | B1a | O | CH$_2$ | CH$_3$ | CH$_2$—CH$_2$ | CH$_3$ | phenyl | [2S-[2α,4α[A,(S*)]]] |
| 195 | B1a | O | CH$_2$ | H | CH=CH | H | phenyl | 2S-cis |
| 196 | B17 | O | CH$_2$ | H | CH$_2$—CH$_2$ | H | phenyl | 2S-cis |

TABLE 10
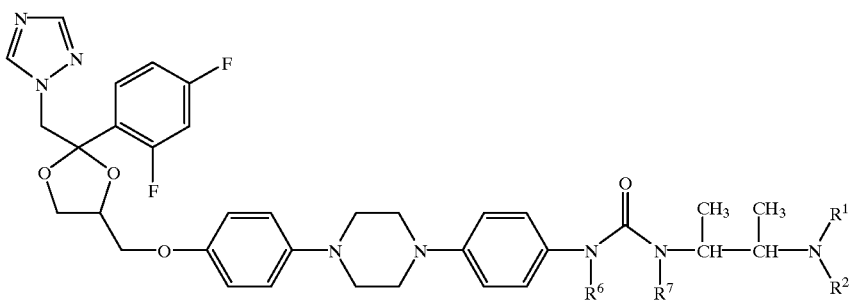
| Co. No. | Ex. No. | R¹ | R² | R⁶ | R⁷ | stereochemistry | salt form |
|---|---|---|---|---|---|---|---|
| 197 | | —CH(CH₃)phenyl | H | H | H | [2S-[2α,4α[2(1R*)]]] | HCl (1:3) H₂O(1:1) |
| 198 | | —CH₂-phenyl | H | H | CH₃ | 2S-cis | — |
TABLE 11
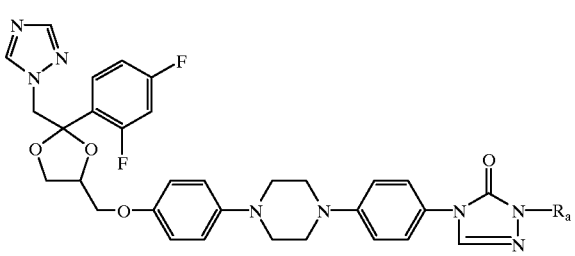
| Co. No. | Ex. No. | $R_a$ | stereochemistry; $[\alpha]^D_{20}$ @ concentration (in mg/5 ml DMF); salts; melting point (° C.) |
|---|---|---|---|
| 199 | B16 | 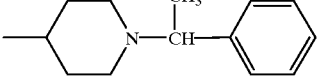 | 2S-cis |
| 200 | B1a | 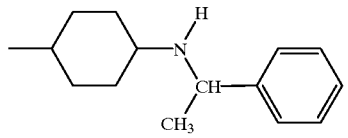 | [2S-[2α,4α[1α,4α(R*)]]] |
| 201 | B1a | 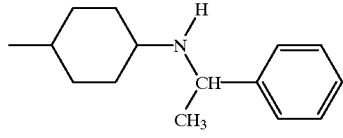 | [2S-[2α,4α[1α,4α(R*)]]] |
| 202 | B1a | 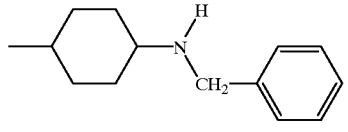 | [2S-[2α,4α[1α,4α(R*)]]] |
| 203 | B1a | 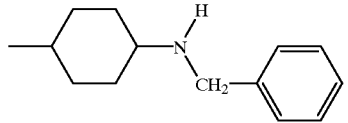 | [2S-[2α,4β[1α,4α(R*)]]] |

TABLE 11-continued

| Co. No. | Ex. No. | $R_a$ | stereochemistry; $[\alpha]^P{}_{20}$ @ concentration (in mg/5 ml DMF); salts; melting point (° C.) |
|---|---|---|---|
| 204 | B1b | (4-piperidinyl-methyl, N—H) | 2S-cis |

C. PHARMACOLOGICAL EXAMPLES

EXAMPLE C1

A panel of 8 isolates of Candida spp. (Panel 1) was tested. The panel included an azole-resistant *C. albicans strain*. A panel of 6 other fungi (Panel 2) comprised 3 dermatophyte isolates and single isolates of *Aspergillus migatus, Cryptococcus neoformans* and *Sporothrix schenckii*.

For screening of these two panels, a series of solutions of the test compounds in dimethyl sulfoxide (DMSO) was prepared. The DMSO solutions were then diluted 100-fold into CYG broth (Odds, F. C., Antimicrobial Agents and Chemotherapy, 1992, 36, 1727–1737) and inoculated with yeast cells to an initial concentration of $10^4$/ml and with other fungi to an equivalent concentration determined by turbidimetry. Cultures were incubated in the wells of microdilution plates at 37° C. for 48 hours for yeasts or at other times and temperatures for other fungi. Growth in wells containing test compounds was estimated turbidimetrically as a percentage of growth in test compound-free controls and the lowest concentration of test compound that inhibited the growth of an isolate below 35% of control growth was recorded as the lowest active dose (LAD).

Compound Nos. 1 to 4, 6 to 19, 21 to 29, 31, 34, 35, 40, 41, 43 to 47, 49, 50, 52 to 62, 64, 66, 68, 71 to 79, 81 to 86, 93 to 98, 100 to 109, 114 to 121, 130 to 132, 134 to 153, 155 to 190, 197 and 198 had a geometric mean minimum inhibitory concentration-value (MIC) ranging between 0.01 and 1.0 $\mu$M for the Candida spp. The other compounds were either not tested or had an MIC of more than 1 $\mu$M.

Compound Nos. 1 to 4, 6 to 31, 34, 35, 40, 41, 43 to 50, 52 to 62, 64 to 69, 71 to 86, 91 to 98, 100 to 123, 130, 132, 134 to 139, 142 to 156, 158, 160 to 178, 180 to 182, 184 to 190 and 198 had a MIC ranging between 0.01 and 1.0 $\mu$M for the other fungi. The other compounds were either not tested or had an MIC of more than 1 $\mu$M.

EXAMPLE C2

A panel of 24 Candida isolates, 8 isolates of Aspergillus spp., 8 dermatophytes, 10 Zygomycetes, 10 Fusarium spp., 2 *Cryptococcus neoformans* and 8 dematiaceous hyphomycetes was used.

Inocula were prepared as in example C1 but the culture medium used in this test was RPMI 1640 buffered with MOPS, with 2% glucose (Odds, F. C., Antimicrobial Agents and Chemotherapy, 1995, 39, 2051–2060). Test compounds were added to the medium from DMSO solutions to give final concentrations in the series 10, 3.2, 1.0, 0.32, 0.10, 0.032, 0.010, 0.0032 and 0.0010 $\mu$M. Incubation times and temperatures were as in example C1. Once the microdilution plates had been read for growth turbidity spectrophotometrically, samples of material were removed from the test cultures to inoculate 10 $\mu$l volumes on plates of Sabouraud glucose agar. The plates were incubated at 37° C. for 48 hours for yeasts or at other times and temperatures for other species. Geometric mean minimum fungicidal concentrations in $\mu$M which were determined as the lowest concentrations of the test compound that completely or substantially eliminated reappearance of fungal growth on the Sabouraud plates for Candida spp. ranged between 1 and 10 $\mu$M for compound Nos 5, 8 to 10, 14 to 18, 20 to 22, 38 to 52, 54, 55, 59 to 63, 65, 66, 68, 71 to 86, 91 to 120, 123, 138 to 143, 145 to 148, 150 to 154, 163 to 165, 167 to 178, 185 to 189, 191, 193, 194, 197, 199 and 203;

for Aspergillus spp. ranged between 0.1 and 10 $\mu$M for compound Nos 5, 8 to 10, 14 to 18, 20 to 22, 38 to 52, 54 to 56, 59 to 86, 91 to 120, 123, 138 to 143, 145 to 148, 150 to 153, 163 to 165, 167 to 178, 185 to 189, 191, 193, 194, 199 and 203;

for Dermatophytes ranged between 0.1 and 10 pAM for compound Nos 5, 8 to 10, 14 to 18, 20 to 22, 41, 43 to 47, 49, 50, 52, 54 to 56, 59 to 62, 66, 68, 71 to 83, 85, 86, 92 to 120, 123, 138 to 143, 145, 163 to 165, 167 to 174, 185 to 188, 193 and 199;

for Zygomycetes ranged between 1 and 10 $\mu$M for compound Nos 43, 51, 74, 77, 79, 83, 86, 93, 95, 96, 98, 100 to 102, 107, 108, 120, 138, 143, 146, 163 to 165, 170, 171, 175, 176, 185 to 187, 193, 194 and 203; for Fusarium spp. ranged between 1 and 10 $\mu$M for compound Nos 43 to 46, 54, 60, 61, 73, 74,77, 79, 83, 86, 100 to 107, 109, 116, 117, 120, 138, 143, 145, 146, 148, 151, 163, 165, 168, 175 to 177, 186 to 188, 193, 194, 199 and 203; and for other fungi ranged between 0.1 and 10 $\mu$M for compound Nos 5, 8 to 10, 14 to 18, 20 to 22, 38 to 52, 54 to 56, 59 to 86, 91 to 93, 95 to 120, 123, 138 to 143, 145 to 148, 150 to 153, 163 to 165, 167 to 178, 185 to 189, 191, 193, 194, 197, 199 and 203.

The compound numbers not mentioned were either not tested or had a geometric mean minimum fungicidal concentrations of more than 10 μM.

D. PHYSICOCHEMICAL EXAMPLE

EXAMPLE D1

Water Solubility

An excess of compound was added to water buffered with 0.1 M citric acid and 0.2 M Na$_2$HPO$_4$ in a ratio of 61.5/38.5 (pH =4). The mixture was shaken during 1 day at room temperature. The precipitate was filtered off. The concentration of the compound was measured via UV spectroscopy. Compound Nos 9, 10, 15 to 18, 21, 38, 39, 42, 49, 51, 52, 55, 61, 63, 65, 66, 68, 70, 71, 73, 74, 81 to 86, 93, 100 to 102, 106, 107, 109, 114, 115, 139, 140, 142, 143, 147, 149 to 152, 155 to 159, 172, 174 to 179, 181 to 184, 187, 189 to 191, 193, 194, 197, 198, 200, 201 and 203 showed a solubility of more than 0.1 mg/ml. The other compounds were either not tested or showed a solubility of less than 0.01 mg/ml.

E. COMPOSITION EXAMPLE

EXAMPLE E.1

Injectable Solution 1.8 Grams methyl 4-hydroxybenzoate and 0.2 grams sodium hydroxide were dissolved in about 0.5 l of boiling water for injection. After cooling to about 50° C. there were added while stirring 0.05 grams propylene glycol and 4 grams of the active ingredient. The solution was cooled to room temperature and supplemented with water for injection q.s. ad 1 l giving a solution comprising 4 mg/ml of active ingredient. The solution was sterilized by filtration and filled in sterile containers.

EXAMPLE E.2

Transungual Composition 0.144 g KH$_2$PO$_4$, 9 g NaCl, 0.528 g Na$_2$HPO$_4$.2H$_2$O was added to 800 ml H$_2$O and the mixture was stirred. The pH was adjusted to 7.4 with NaOH and 500 mg NaN$_3$ was added. Ethanol (42 v/v %) was added and the pH was adjusted to 2.3 with HCl. 15 mg active ingredient was added to 2.25 ml PBS/Ethanol (42%; pH 2.3) and the mixture was stirred and treated with ultrasound. 0.25 ml PBS/Ethanol (42%; pH 2.3) was added and the mixture was further stirred and treated with ultrasound until all active ingredient was dissolved, yielding the desired transungual composition.

What is claimed is:

1. A compound of formula

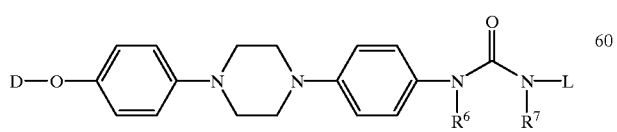

(I)

a N-oxide form, a pharmaceutically acceptable addition salt or a stereochemically isomeric form thereof, wherein L represents a radical of formula

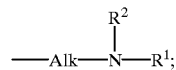 (a)

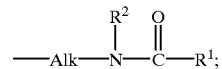 (b)

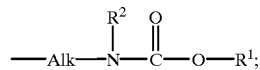 (c)

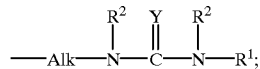 (d)

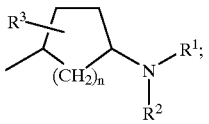 (e)

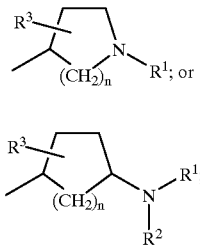 (f)

wherein each Alk independently represents C$_{1-6}$ alkanediyl optionally substituted with hydroxy or C$_{1-4}$alkyloxy;

each n independently is 1, 2 or 3;

Y represents O, S or NR2;

each R$^1$ independently represents hydrogen, aryl, Het$^1$, or C$_{1-6}$alkyl optionally substituted with one, two or three substituents each independently selected from halo, hydroxy, mercapto, C$_{1-4}$alkyloxy, C$_{1-4}$alkylthio, aryloxy, arylthio, arylC$_{1-4}$alkyloxy, arylC$_{1-4}$alkylthio, cyano, amino, mono- or di(C$_{1-4}$alkyl)amino, mono- or di(aryl)amino, mono- or di(arylC$_{1-4}$alkyl)amino, C$_{1-4}$alkyloxycarbonylamino, benzyloxycarbonylamino, aminocarbonyl, carboxyl, C$_{1-4}$alkyloxycarbonyl, guanidinyl, aryl or Het$^2$;

each R$^2$ independently represents hydrogen or C$_{1-6}$alkyl; or in case R$^1$ and R$^2$ are attached to the same nitrogen atom, they may be taken together to form a heterocyclic radical selected from morpholinyl, pyrrolidinyl, piperidinyl, homopiperidinyl or piperazinyl; said heterocyclic radical may optionally be substituted with C$_{1-4}$alkyl, aryl, Het$^2$, arylC$_{1-4}$alkyl, Het$^2$C$_{1-4}$alkyl, hydroxyC$_{1-4}$alkyl, amino, mono- or di(C$_{1-4}$alkyl)amino, aminoC$_{1-4}$alkyl, mono- or di(C$_{1-4}$alkyl)aminoC$_{1-4}$alkyl, carboxyl, aminocarbonyl, C$_{1-4}$alkyloxycarbonyl, C$_{1-4}$alkyloxycarbonylamino or mono- or di(C$_{1-4}$alkyl)aminocarbonyl; or they may be taken together to form an azido radical;

each R$^3$ independently represents hydrogen, hydroxy or C$_{1-4}$alkyloxy;

aryl represents phenyl, naphthalenyl, 1,2,3,4-tetrahydro-naphthalenyl, indenyl or indanyl; each of said aryl groups may optionally be substituted with one or more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy$C_{1-4}$alkyl, amino$C_{1-4}$alkyl, mono- or di($C_{1-4}$alkyl)amino$C_{1-4}$alkyl;

$Het^1$ represents a monocyclic or bicyclic heterocyclic radical; said monocyclic heterocyclic radical being selected from the group pyridinyl, piperidinyl, homopiperidinyl, pyrazinyl, pyrimidinyl, pyridazinyl, triazinyl, triazolyl, pyranyl, tetrahydropyranyl, imidazolyl, imidazolinyl, imidazolidinyl, pyrazolyl, pyrazolinyl, pyrazolidinyl, thiazolyl, thiazolidinyl, isothiazolyl, oxazolyl, oxazolidinyl, isoxazolyl, pyrrolyl, pyrrolinyl, pyrrolidinyl, furanyl, tetrahydrofuranyl, thienyl, thiolanyl, dioxolanyl; said bicyclic heterocyclic radical being selected from the group quinolinyl, 1,2,3,4-tetrahydro-quinolinyl, isoquinolinyl, quinoxalinyl, quinazolinyl, phtalazinyl, cinnolinyl, chromanyl, thiochromanyl, 2H-chromenyl, 1,4-benzodioxanyl, indolyl, isoindolyl, indolinyl, indazolyl, purinyl, pyrrolopyridinyl, furanopyridinyl, thienopyridinyl, benzothiazolyl, benzoxazolyl, benzisothiazolyl, benzisoxazolyl, benzimidazolyl, benzofuranyl, benzothienyl; whereby each of said mono- or bicyclic heterocycle may optionally be substituted with one or where possible more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy-$C_{1-4}$alkyl, amino$C_{1-4}$alkyl, mono- or di($C_{1-4}$alkyl)amino$C_{1-4}$alkyl, aryl or aryl$C_{1-4}$alkyl; $Het^2$ is the same as $Het^1$ and may also be a monocyclic heterocycle selected from piperazinyl, homopiperazinyl, 1,4-dioxanyl, morpholinyl, thiomorpholinyl; whereby each of said monocyclic heterocycle may optionally be substituted with one or where possible more substituents selected from halo, $C_{1-4}$alkyl, hydroxy, $C_{1-4}$alkyloxy, nitro, amino, trifluoromethyl, hydroxy$C_{1-4}$alkyl, $C_{1-4}$alkyloxy$C_{1-4}$alkyl, amino$C_{1-4}$alkyl, mono- or di-($C_{1-4}$alkyl)amino$C_{1-4}$alkyl, aryl or aryl$C_{1-4}$alkyl;

$R^6$ represents hydrogen or $C_{1-4}$alkyl;

$R^7$ represents hydrogen or $C_{1-4}$alkyl; or $R^6$ and $R^7$ taken together form a bivalent radical of formula —$R^6$—$R^7$—wherein —$R^6$—$R^7$—is:

| | |
|---|---|
| —N=CH— | (i), |
| —CH=N— | (ii), |
| —CH=CH— | (iii), |
| —CH$_2$—CH$_2$ | (iv), | wherein one hydrogen atom in the radicals (i) and (ii) may be replaced with a $C_{1-4}$alkyl radical and one or more hydrogen atoms in radicals (iii) and (iv) may be replaced by a $C_{1-4}$alkyl radical;

D represents a radical of formula

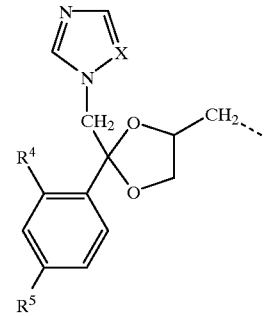

(D$_1$)

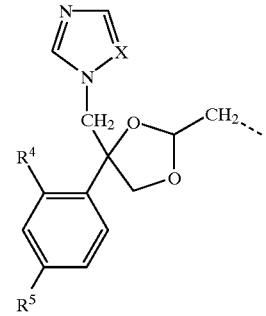

(D$_2$)

wherein

X is N or CH;

$R^4$ is hydrogen or halo;

$R^5$ is halo.

2. A compound as claimed in claim 1 wherein D is a radical of formula D$_1$.

3. A compound as claimed in claim 2 wherein L is a radical of formula (a), (b) or (c).

4. A compound as claimed in claim 3 wherein Alk is 1,2-ethanediyl, 1,2-propanediyl, 2,3-propanediyl, 1,2-butanediyl, 3,4-butanediyl, 2,3-butanediyl, 2,3-pentanediyl or 3,4-pentanediyl.

5. A compound as claimed in claim 4 wherein $R^1$ represents hydrogen, aryl, $Het^1$, or $C_{1-6}$alkyl optionally substituted with one, two or three substituents each independently selected from halo, hydroxy, $C_{1-4}$alkyloxy, aryloxy, aryl$C_{1-4}$alkyloxy, cyano, amino, mono- or di($C_{1-4}$alkyl)amino, mono- or di(aryl$C_{1-4}$alkyl)amino, $C_{1-4}$alkyloxycarbonylamino, aminocarbonyl, aryl or $Het^2$; $R^2$ represents hydrogen or $C_{1-6}$alkyl; or in case $R^1$ and $R^2$ are attached to the same nitrogen atom, they may also be taken together to form a heterocyclic radical selected from morpholinyl, pyrrolidinyl, piperidinyl or piperazinyl; said heterocyclic radical may optionally be substituted with $C_{1-4}$alkyl, aryl, aryl$C_{1-4}$alkyl, hydroxy$C_{1-4}$alkyl, amino, mono- or di($C_{1-4}$alkyl)amino, mono- or di($C_{1-4}$alkyl)amino$C_{1-4}$alkyl or $C_{1-4}$alkyloxycarbonylamino; or $R^1$ and $R^2$ may also be taken together to form an azido radical.

6. A compound as claimed in claim 1 wherein L is a radical of formula

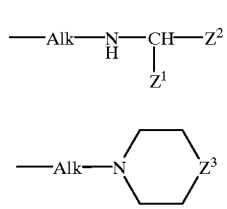

(a-1)

(a-2)

wherein $Z^1$ is aryl, arylmethyl, arylethyl, $Het^1$ or $C_{1-4}$alkyl;

$Z^2$ is hydrogen, carboxyl, $C_{1-4}$alkyloxycarbonyl, aminocarbonyl or methyl optionally substituted with hydroxy, methoxy, amino or mono- or di(methyl)amino;

or $Z^1$ and $Z^2$ taken together with the carbon atom to which they are attached form a piperidinyl ring substituted with arylmethyl, arylethyl or $C_{1-4}$alkyl;

$Z^3$ is O, N—$C_{1-4}$alkyl or N-aryl.

7. A compound as claimed in claim 1 wherein the compound is

4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4dihydro-2-[2-[(1-phenylethyl)amino]-1-methylpropyl]-3H-1,2,4triazol-3-one;

4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(2-phenylethyl)amino]-1-methylpropyl]-3H-1,2,4-triazol-3-one;

4-[4-[4-[4-[[2(2,4difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-(4-phenyl-1-piperazinyl)-1-methylpropyl]-3H-1,2,4-triazol-3-one;

4-[4-[4-[4-[[2-(2,4difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[(3-phenylpropyl)amino]-1-methylpropyl]-3H-1,2,4-triazol-3-one;

4-[4-[4-[4-[[2-(2,4difluorophenyl)2-(1H-1,2,4-triazol-1-ylmethyl)-1,3-dioxolan-4-yl]methoxy]phenyl]-1-piperazinyl]phenyl]-2-[2-[[(2-fluorophenyl)methyl]amino]1-methylpropyl]-2,4-dihydro-3H-1,2,4-triazol-3-one;

4-[4-[4-[4-[[2-(2,4difluorophenyl)-2-(1H-1,2,4-triazol-1-ylmethyl)-1,3-dioxolan-4-yl]methoxy]phenyl]-1-piperazinyl]phenyl]-2,4dihydro-2-[2-[(phenylmethyl)amino]-1-methylpropyl]-3H-1,2,4,-triazol-3one;

4-[4-[4-[4-[[2-(2,4difluorophenyl)-2-(1H-1,2,4-triazol-1-ylmethyl)-1,3-dioxolan4-yl]methoxy]phenyl]-1-piperazinyl]phenyl]-2,4dihydro 2-[2-[[(2-methoxyphenyl)-methyl]amino)-1-methylpropyl]-3H-1,2,4triazol-3-one;

4-[4-[4-[4-[[2-(2,4-difluorophenyl)-2-(1H-1,2,4triazol-1-ylmethyl)-1,3-dioxolan-4yl]methoxy]phenyl]-1-piperazinyl]phenyl]-2,4-dihydro-2-[2-[(2-phenoxyethyl)amino]-1-methylpropyl]-3H-1,2,4-triazol-3-one;

4-[4-[4-[4-[[2-(2,4difluorophenyl)-2-(1H-1,2,4-triazol-1-ylmethyl)1,3-dioxolan 4-yl]methoxy]phenyl]-1-piperazinyl]phenyl]-2,4-dihydro-2-[2-[(2,3-dihydro-1 H-inden-2-yl)amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3dioxolan-4-yl]methoxy]phenyl]-1-piperazinyl]phenyl]-2-[2-[[1-(4-fluorophenyl)ethyl]amino]-1-methylpropyl]-2,4-dihydro-3H-1,2,4-triazol-3-one;

4-[4-[4-[4-[[2-(2,4difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[[1-(phenylmethyl)-4-piperidinyl]amino]-1-methylpropyl]-3H-1,2,4-triazol-3-one;

4-[4-[4-[4-[[2-(2,4-difluorophenyl)2-(1H-1,2,4-triazol-1-ylmethyl)-1,3-dioxolan-4-yl]methoxy]phenyl]-1-piperazinyl]phenyl]-2,4-dihydro-2-[2-(4-morpholinyl)-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2-[[1-(hydroxymethyl)-2-phenylethyl]amino)]1-methylpropyl]-3H-1,2,4-triazol-3-one;

4-[4-[4-[4-[[2-(2,4difluorophenyl)-2-(1H-1,2,4-triazol-1-ylmethyl)-1,3-dioxolan-4-yl]methoxy]phenyl]1-piperazinyl]phenyl]-2,4-dihydro-2-[2-[(2-hydroxy-2-phenylethyl)amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2[(2hydroxy-2-phenylethyl)amino]-1-methylpropyl]-3H-1,2,4-triazol-3-one;

4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-[2([[1-(hydroxymethyl)-2-methylpropyl]amino]-1methylpropyl]-3H-1,2,4-triazol-3-one;

4-[4-[4-[4-[[2-(2,4-diclorophenyl)-2-(1H-1,2,4-triazol-1-ylmethyl)-1,3-dioxolan-4-yl]methoxy]phenyl]-1-piperazinyl]phenyl]-2,4-dihydro-2-[2-(1-phenylethyl)amino]1-methylpropyl]-3H-1,2,4-triazol-3-one;

4-[4-[4-[4-[[2-(2,4-difluorophenyl)2-(1H-1,2,4-triazol-1-ylmethyl)-1,3-dioxolan-4-yl]methoxy]phenyl]-1-piperazinyl]phenyl]-2,4-dihydro-2-[1-(1-phenylethyl)4-piperidinyl]-3H-1,2,4-triazol-3-one ;

4-[4-[4-[4-[[2-(2,4-dichlorophenyl)-2(1H-1,2,4-triazol-1-ylmethyl)-1,3-dioxolan-4-yl]methoxy]phenyl]-1-piperazinyl]phenyl]-2,4-dihydro-2-[2-[[1-(hydroxymethyl)-2-methylpropyl]amino]-1-methylpropyl]-3H-1,2,4-triazol-3-one;

2-[4-[4-[4-[[2-(2,4difluorophenyl)-2-(1H-1,2,4-triazol-1-ylmethyl)-1,3-dioxolan-4-yl]methoxy]phenyl]-1-piperazinyl]phenyl]-2,4-dihydro([2-[(phenylmethyl)amino]-1-methylpropyl]-3H-1,2,4,-triazol-3-one;

4-[4-[4-[4-[[2-(2,4-difluorophenyl)-2-(1H-1,2,4-triazol-1-ylmethyl)-1,3-dioxolan4-yl]methoxy]phenyl]-1-piperazinyl]phenyl]-2,4-dihydro-2-[4-[(phenylmethyl)amino]-cyclohexyl]-3H-1,2,4triazol-3-one;

a N-oxide form, a pharmaceutically acceptable addition salt or a stereochemically isomeric form thereof.

8. A compound as claimed in claim 1 which is stereoisometrically pure.

9. A pharmaceutical composition comprising a pharmaceutically acceptable carrier, and as active ingredient a therapeutically effective amount of a compound as defined in claim 1.

10. An intermediate of formula

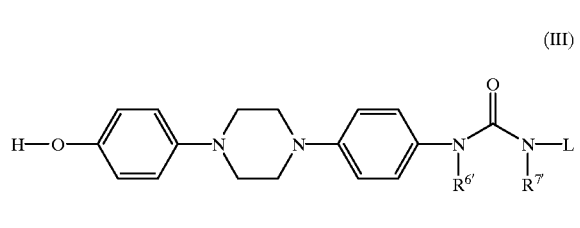

wherein L is as defined in claim 1 and $R^{6'}$ and $R^{7'}$ are the same as $R^6$ and $R^7$ as defined in claim 1 but other than hydrogen.

11. A process of preparing a compound of formula (I) wherein D and L are as defined in claim 1 and $R^6$ and $R^7$ are as defined as in claim 1 but other than hydrogen, said $R^6$ and $R^7$ being represented by $R^{6'}$ and $R^{7'}$ and said compound being represented by formula (I'), comprising, a) reacting an intermediate of formula (II) wherein $W^1$ is a suitable leaving group, with an intermediate of formula (III) in a reaction-inert solvent and in the presence of a suitable base;

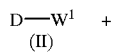

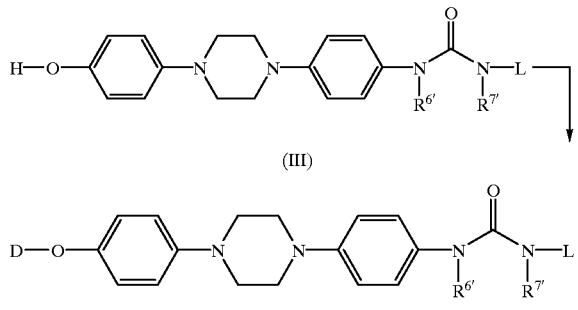

b) N-alkylating an intermediate of formula (IV) with an intermediate of formula (V) wherein $W^2$ is a suitable leaving group and wherein primary and secondary amines in L, in case they are present, are protected with a protective group P being a $C_{1-4}$alkyloxycarbonyl group, in a reaction-inert solvent and in the presence of a base; and in case L was protected, subsequently deprotecting L using art-known deprotection techniques;

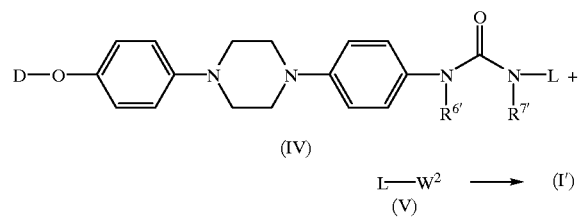

c) reacting an intermediate of formula (VI) wherein $W^3$ is a suitable leaving group, with an intermediate of formula (VII) or $NaN_3$ optionally in the presence of a suitable base and optionally in a reaction-inert solvent; thus obtaining a compound of formula (I') wherein L is a radical of formula (a);

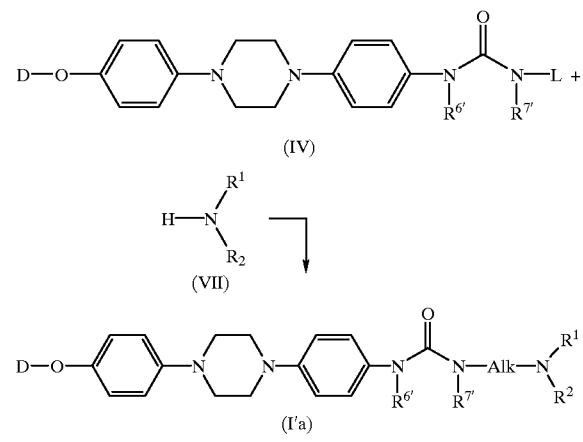

and, if desired, converting compounds of formula (I') into each other following art-known transformations; and further, if desired, converting the compounds of formula (I'), into a therapeutically active non-toxic acid addition salt by treatment with an acid, or conversely, converting the acid addition salt form into the free base by treatment with alkali; and, if desired, preparing stereochemically isomeric forms or N-oxide forms thereof.

12. A method of treating warm-blooded animals suffering from fungal infections comprising administering to the warm-blooded animal an effective amount of a compound of claim 1.

* * * * *